United States Patent
Cole et al.

(12) 
(10) Patent No.: US 11,707,310 B1
(45) Date of Patent: Jul. 25, 2023

(54) ANCHOR APPARATUS

(71) Applicant: Little Engine, LLC, Belmont, NC (US)

(72) Inventors: J. Dean Cole, Orlando, FL (US); Franz W. Kellar, Gastonia, NC (US); Michael D. Bissette, Belmont, NC (US); Harold L. Crowder, Concord, NC (US)

(73) Assignee: Little Engine, LLC, Belmont, NC (US)

(*) Notice: Subject to any disclaimer, the term of this patent is extended or adjusted under 35 U.S.C. 154(b) by 202 days.

(21) Appl. No.: 17/181,547

(22) Filed: Feb. 22, 2021

Related U.S. Application Data

(63) Continuation of application No. 16/986,882, filed on Aug. 6, 2020, now Pat. No. 10,925,656, which is a continuation-in-part of application No. 16/786,544, filed on Feb. 10, 2020, now Pat. No. 10,743,858, which is a continuation-in-part of application No. 16/523,747, filed on Jul. 26, 2019, now Pat. No. 10,561,411.

(60) Provisional application No. 62/964,927, filed on Jan. 23, 2020.

(51) Int. Cl.
| | | |
|---|---|---|
| *A61B 17/88* | (2006.01) | |
| *A61B 17/68* | (2006.01) | |
| *A61B 17/82* | (2006.01) | |
| *A61B 17/04* | (2006.01) | |
| A61B 17/00 | (2006.01) | |

(52) U.S. Cl.
CPC ...... *A61B 17/8869* (2013.01); *A61B 17/0401* (2013.01); *A61B 17/683* (2013.01); *A61B 17/82* (2013.01); *A61B 17/8861* (2013.01); *A61B 2017/00862* (2013.01); *A61B 2017/0404* (2013.01); *A61B 2017/0496* (2013.01); *A61B 2017/681* (2013.01)

(58) Field of Classification Search
CPC combination set(s) only.
See application file for complete search history.

(56) References Cited

U.S. PATENT DOCUMENTS

| 5,935,129 | A | 8/1999 | McDevitt et al. |
|---|---|---|---|
| 6,162,234 | A | 12/2000 | Freedland et al. |
| 6,585,730 | B1* | 7/2003 | Foerster ............... A61F 2/0811 411/80 |
| 10,405,849 | B1 | 9/2019 | Cole et al. |

(Continued)

*Primary Examiner* — Sameh R Boles
(74) *Attorney, Agent, or Firm* — Trego, Hines & Ladenheim, PLLC

(57) ABSTRACT

An anchor for anchoring tensile members to bone includes: a housing extending along a central axis, with a hollow interior; a collet in the hollow interior having a central bore for accepting tensile members and an exterior surface, the collet being configured to swage around and against tensile members; a sleeve having a peripheral wall defining interior and exterior surfaces, the sleeve disposed in the housing's hollow interior axially adjacent to the collet, and movable parallel to the central axis between first and second positions; and wherein at least one of the collet exterior surface and the sleeve interior surface is tapered and the sleeve and the collet are arranged so movement of the sleeve from the first position to the second position causes the sleeve interior surface to bear against the collet exterior surface, causing the collet to swage radially inwards around and against one or more tensile members.

7 Claims, 83 Drawing Sheets

(56) References Cited

U.S. PATENT DOCUMENTS

| | | |
|---|---|---|
| 10,478,171 B1 | 11/2019 | Cole et al. |
| 10,555,729 B1 | 2/2020 | Cole et al. |
| 2001/0008971 A1 | 7/2001 | Schwartz et al. |
| 2003/0032983 A1 | 2/2003 | Bonutti et al. |
| 2005/0222488 A1 | 10/2005 | Chang et al. |
| 2008/0288060 A1 | 11/2008 | Kaye et al. |
| 2010/0007140 A1 | 1/2010 | Duquette et al. |
| 2010/0256612 A1 | 10/2010 | Dell'Oca |
| 2012/0095515 A1 | 4/2012 | Hamilton |
| 2013/0131737 A1 | 5/2013 | Cheng et al. |
| 2014/0194907 A1 | 7/2014 | Bonutti et al. |
| 2014/0296979 A1 | 10/2014 | Delfosse et al. |
| 2014/0257381 A1 | 11/2014 | Palese |
| 2017/0035409 A1 | 2/2017 | Fallin et al. |
| 2018/0153599 A1 | 6/2018 | Daly et al. |
| 2019/0282285 A1 | 9/2019 | Bonutti et al. |

\* cited by examiner

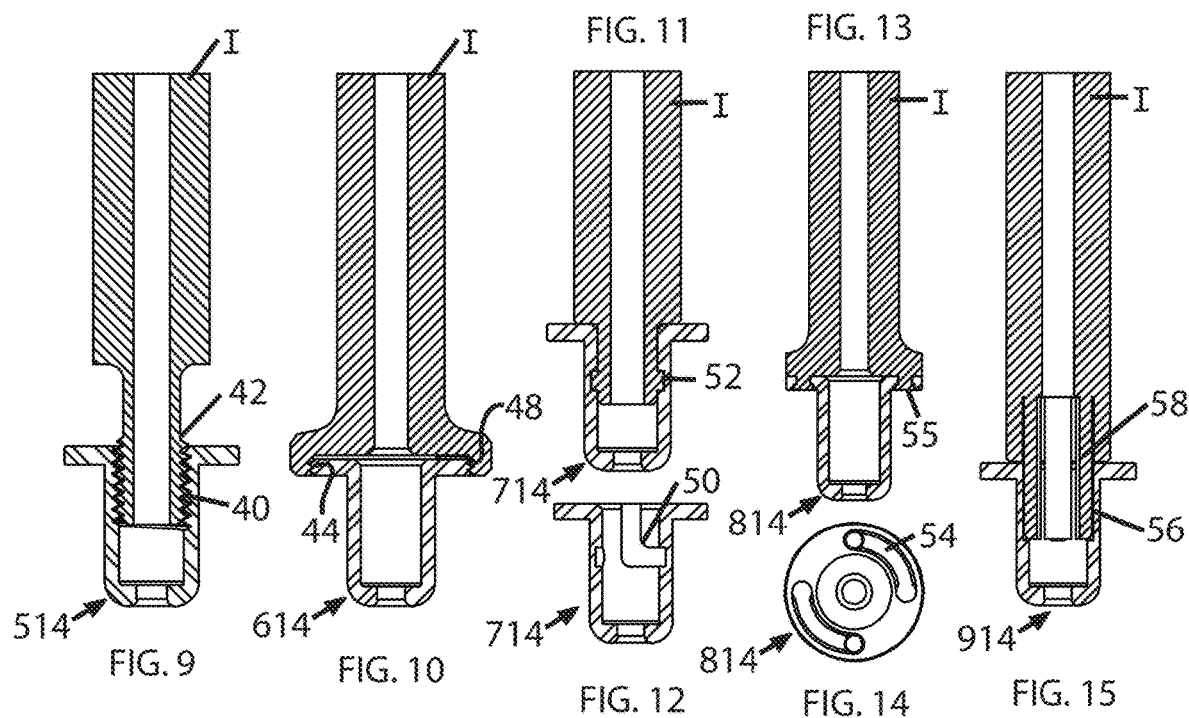

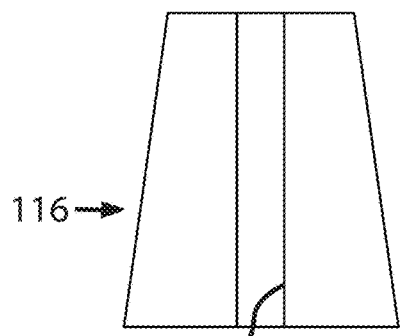
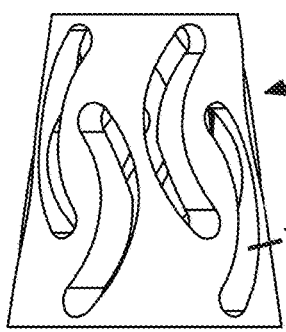
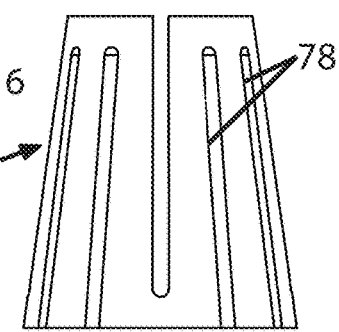
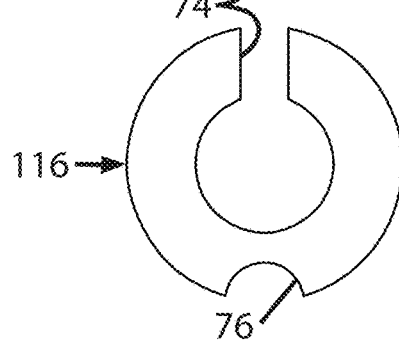
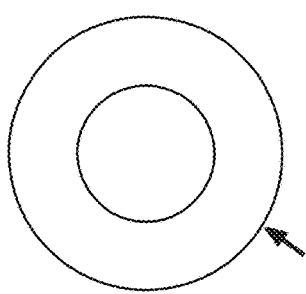
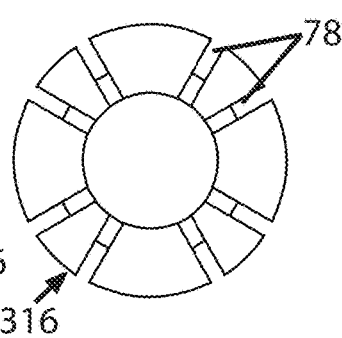

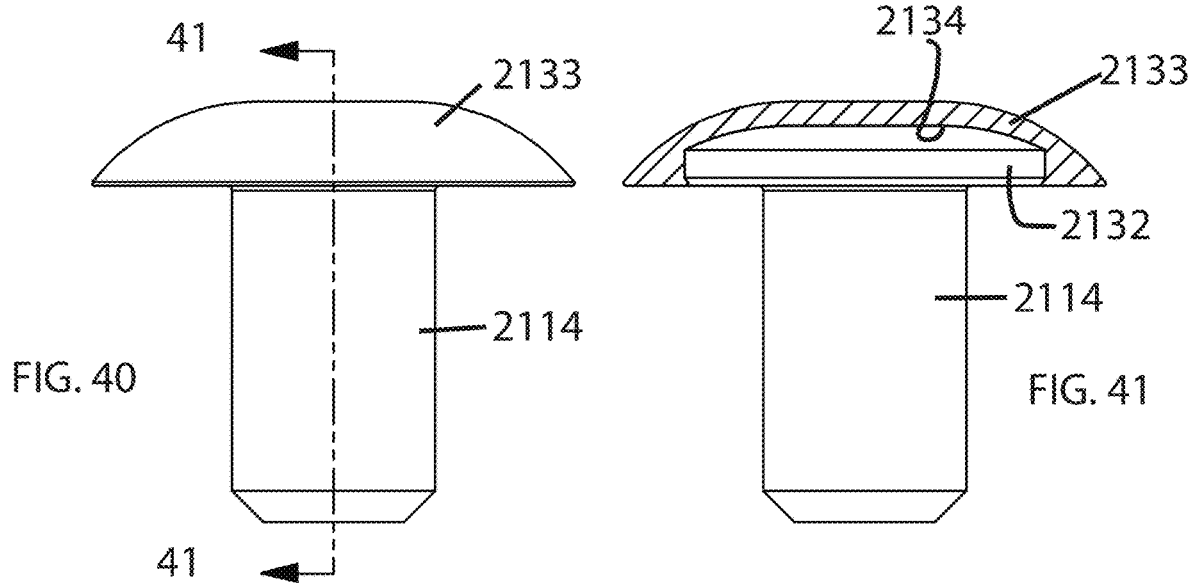
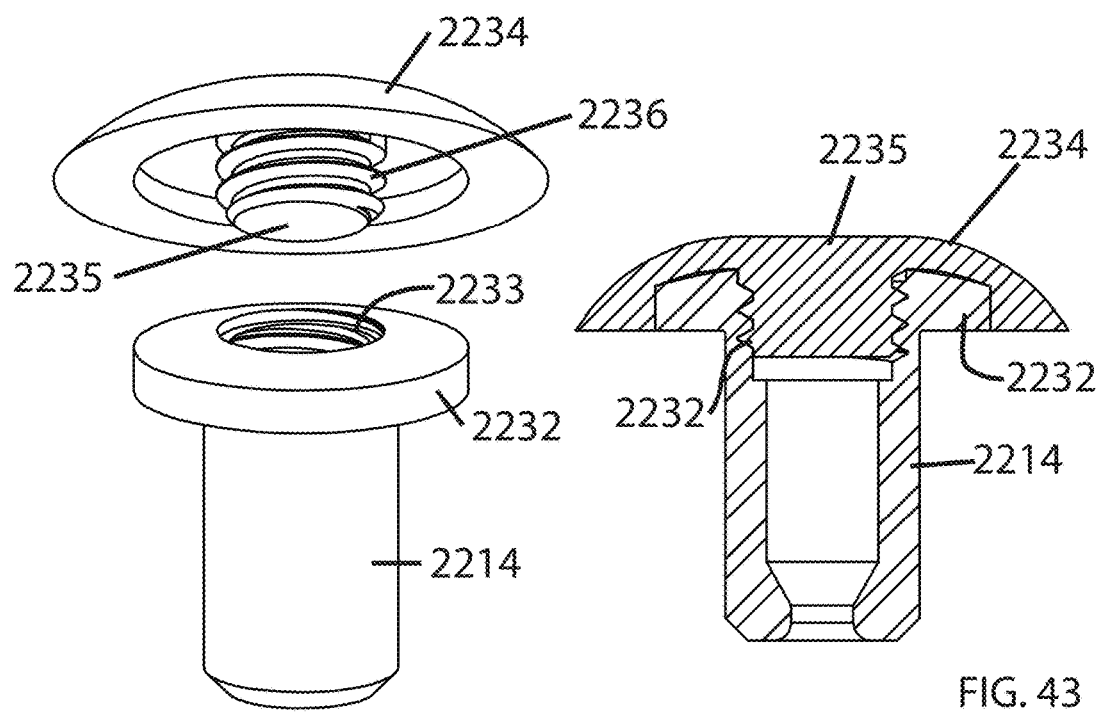

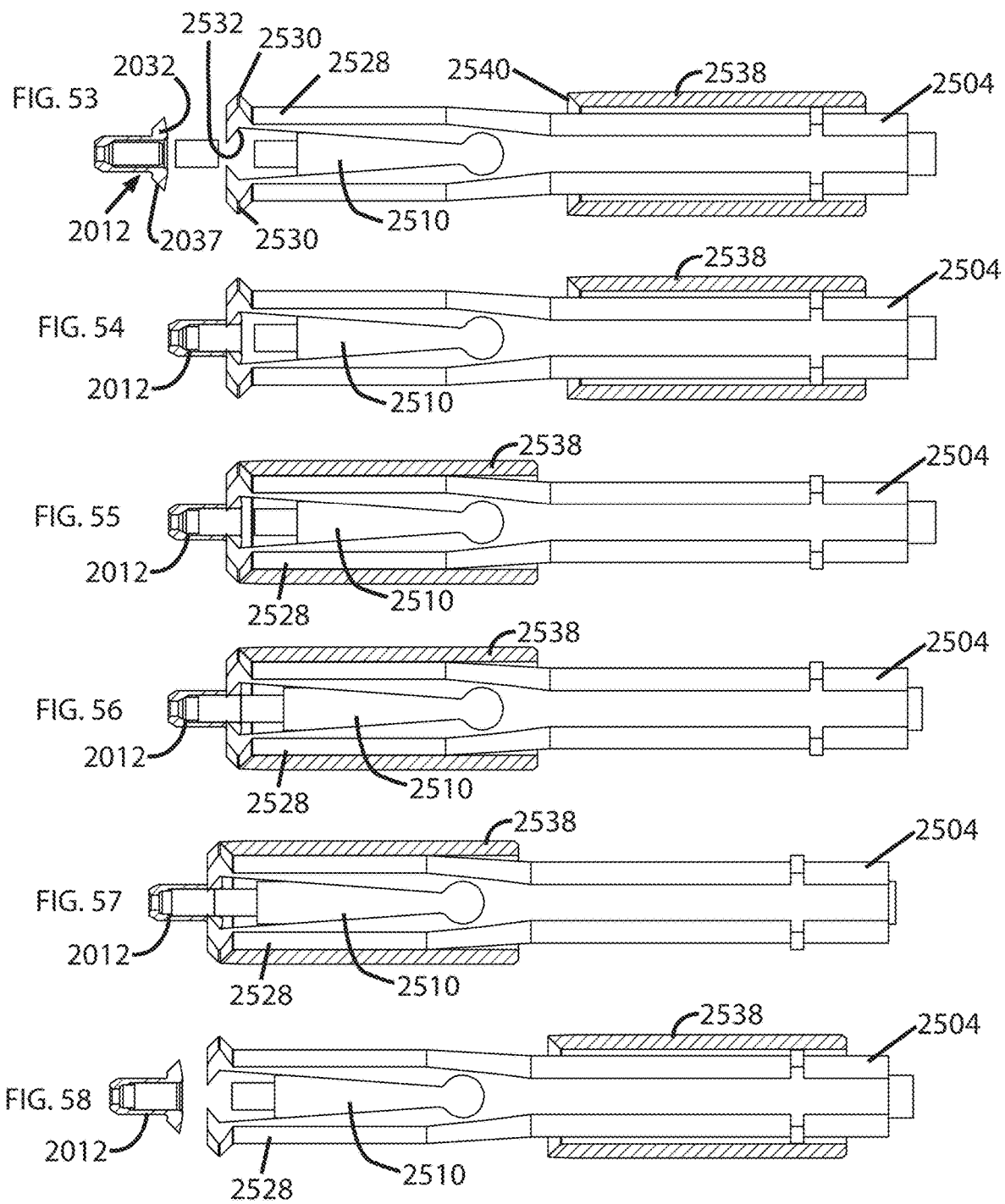

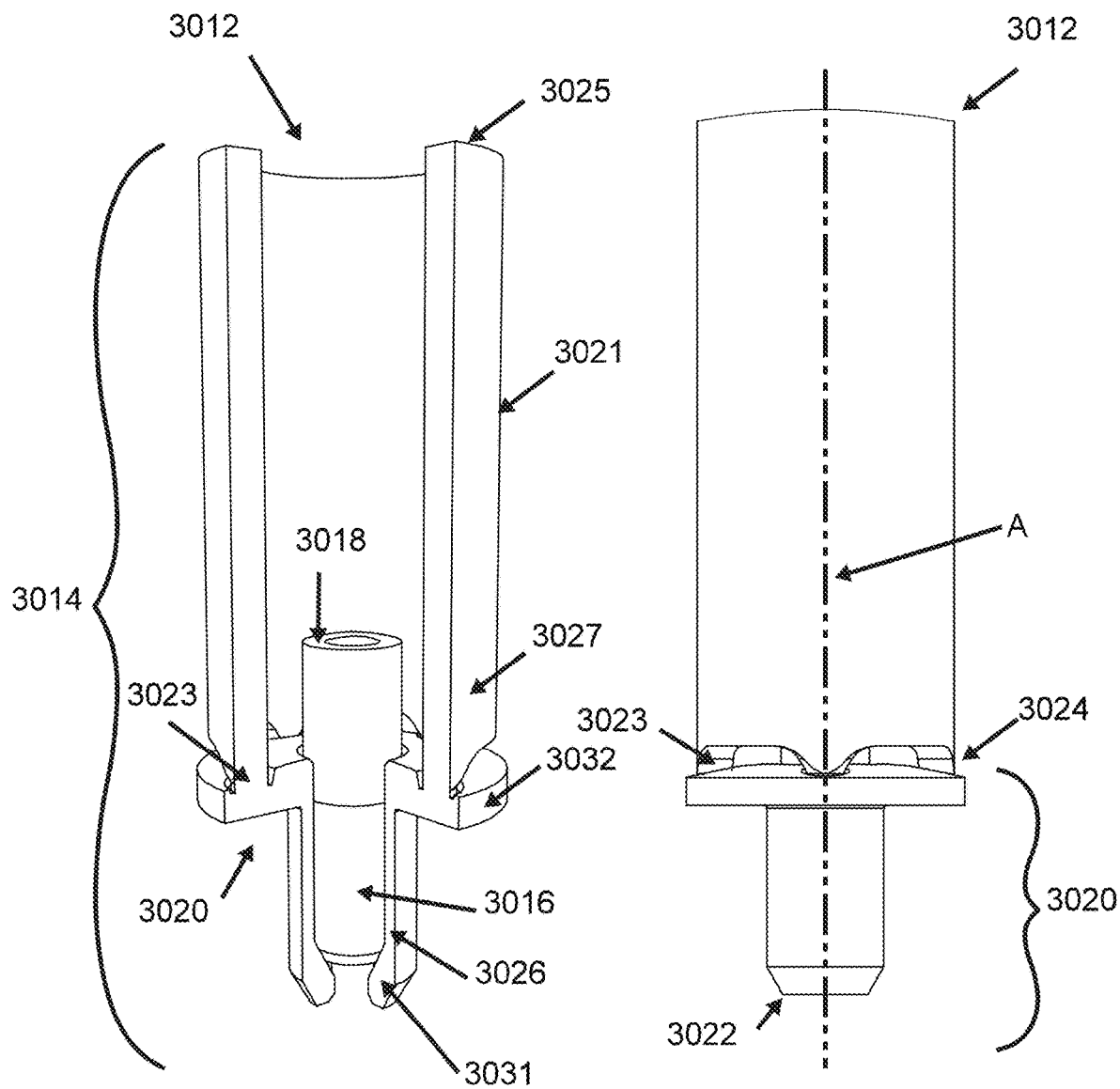

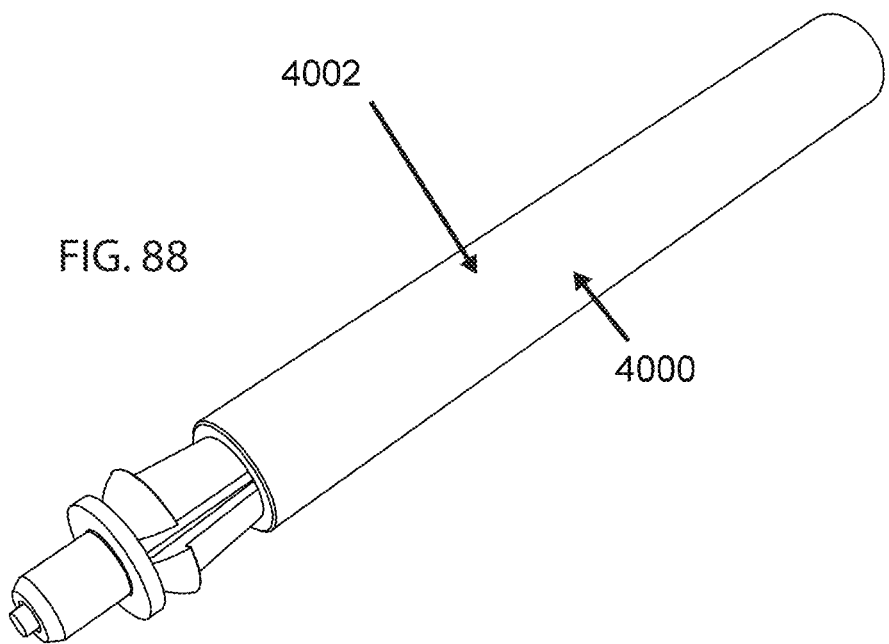
FIG. 88
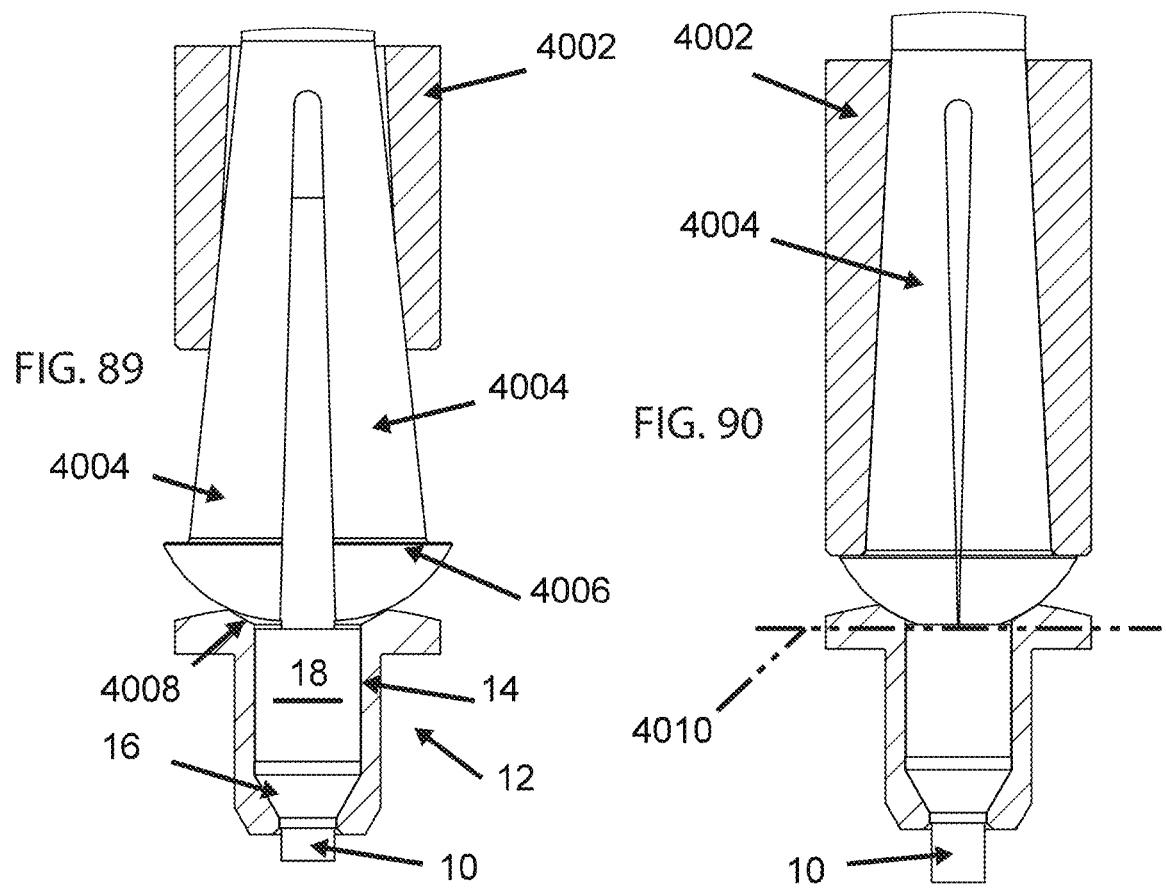
FIG. 89
FIG. 90

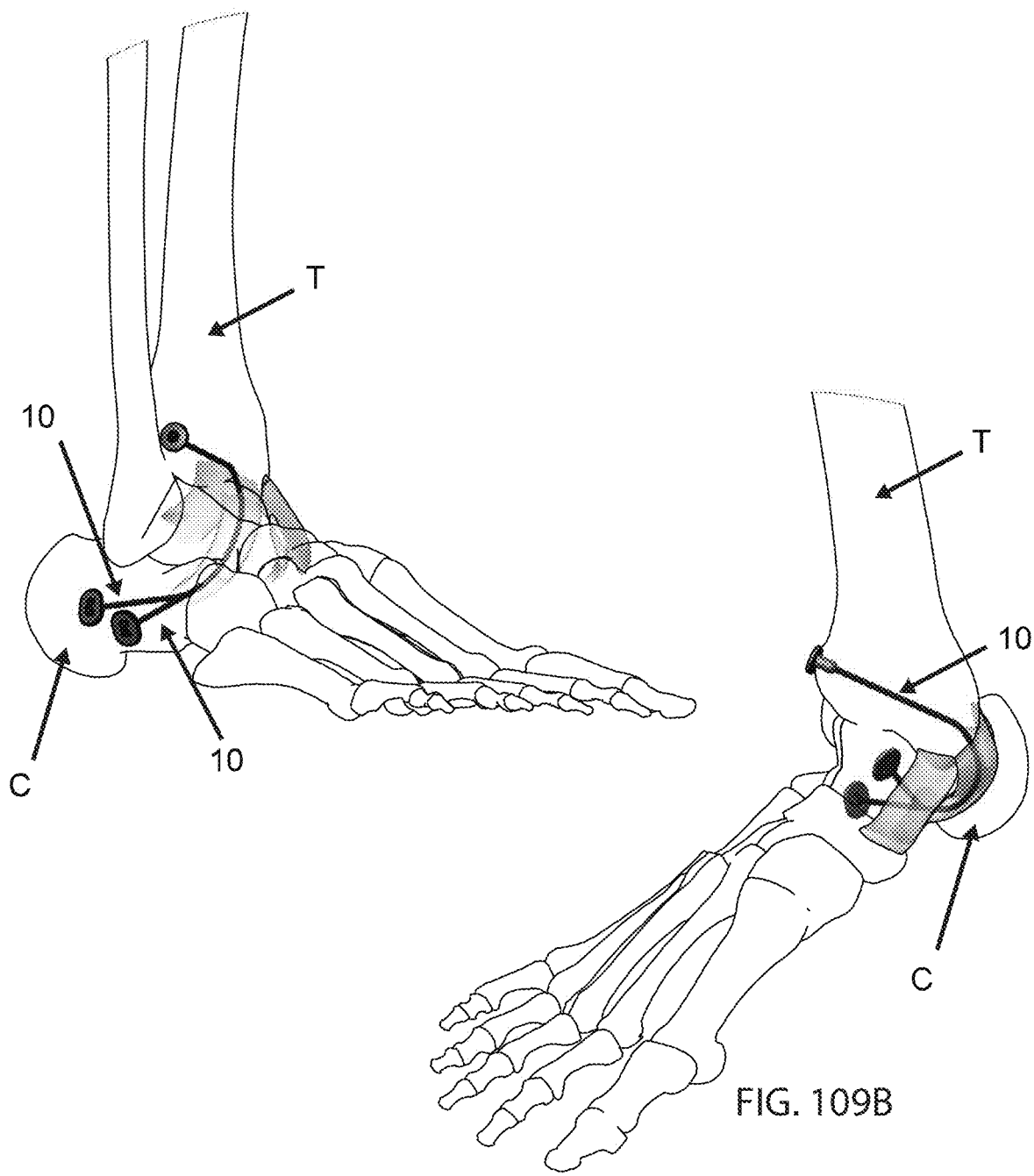

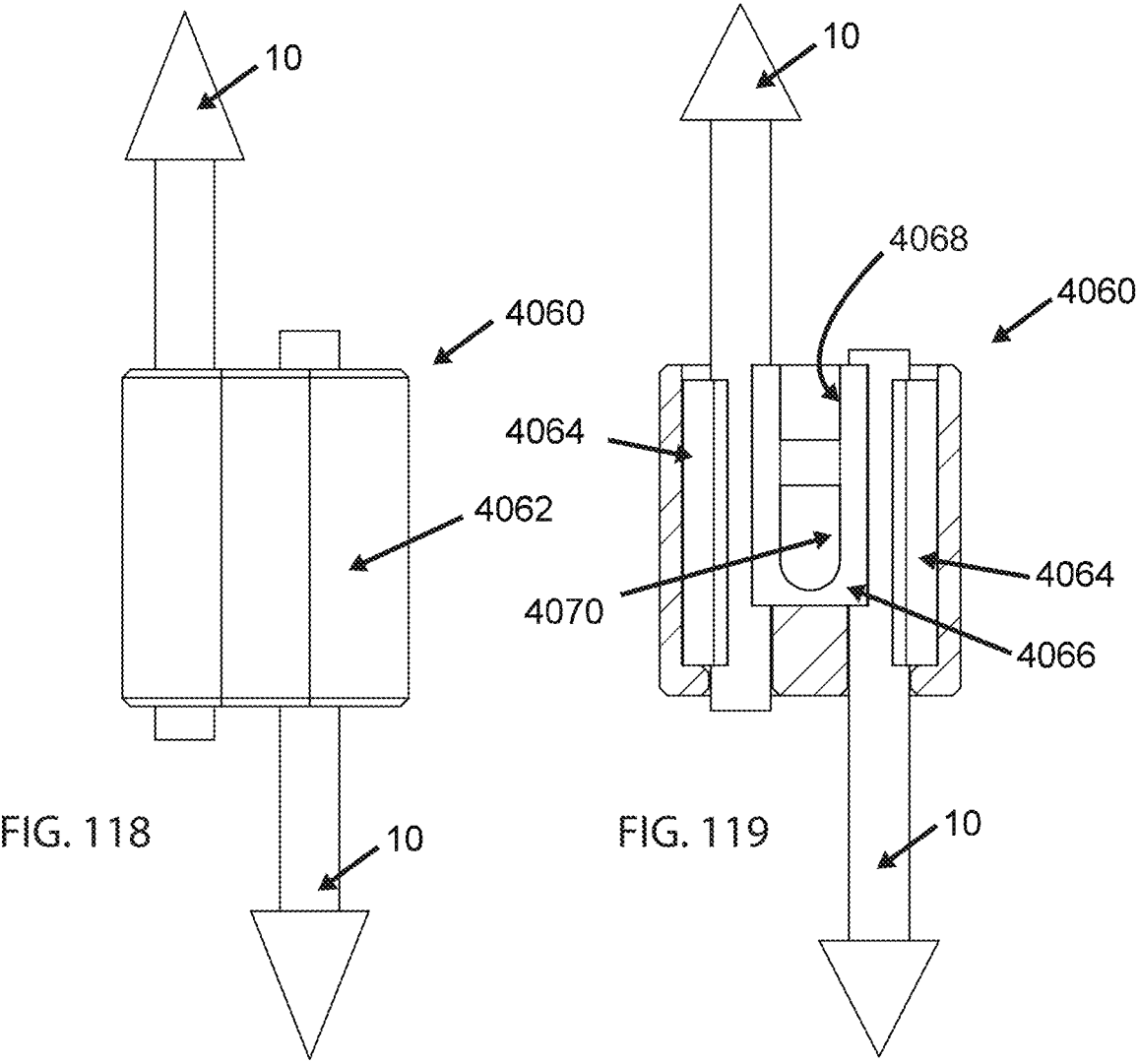

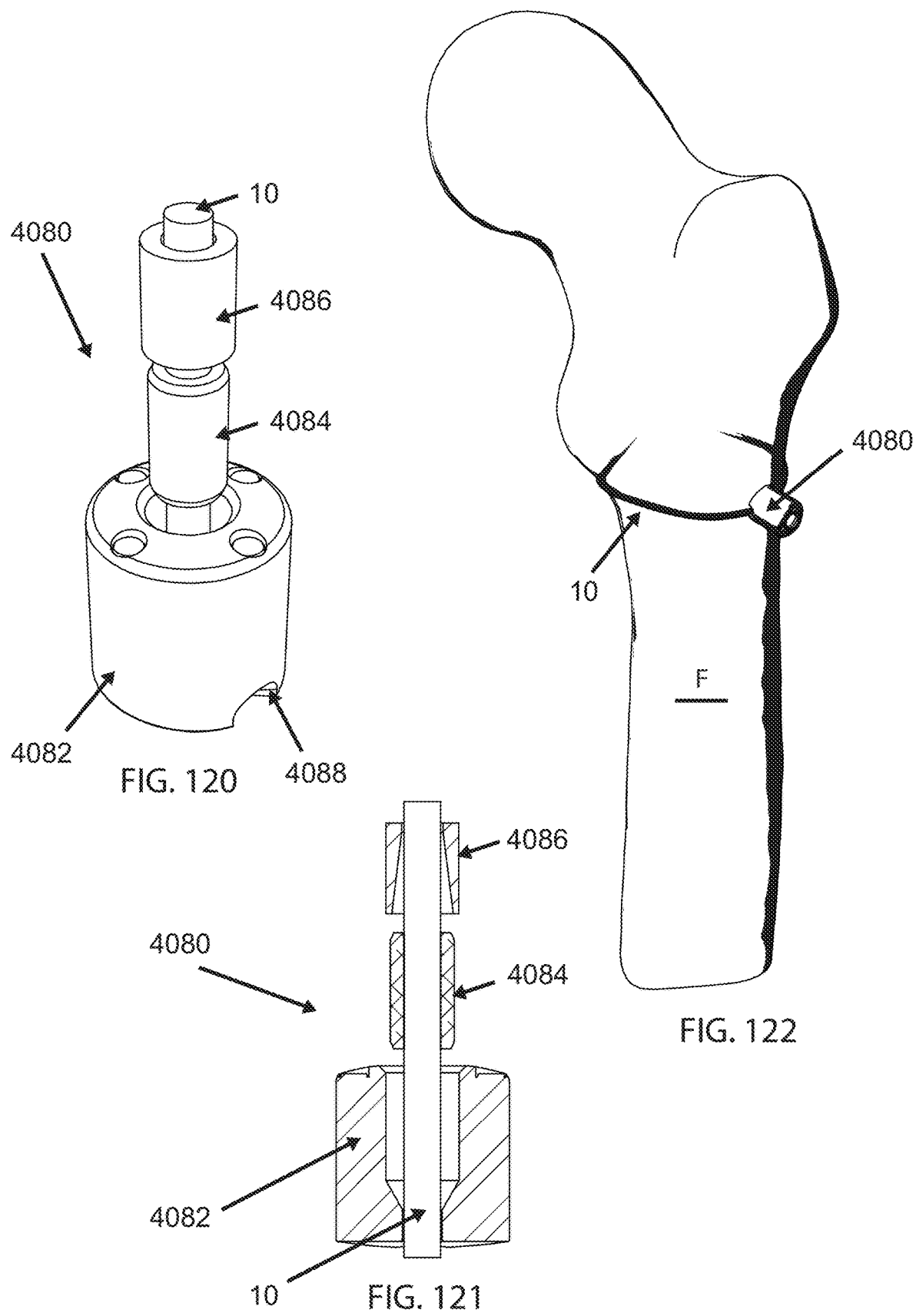

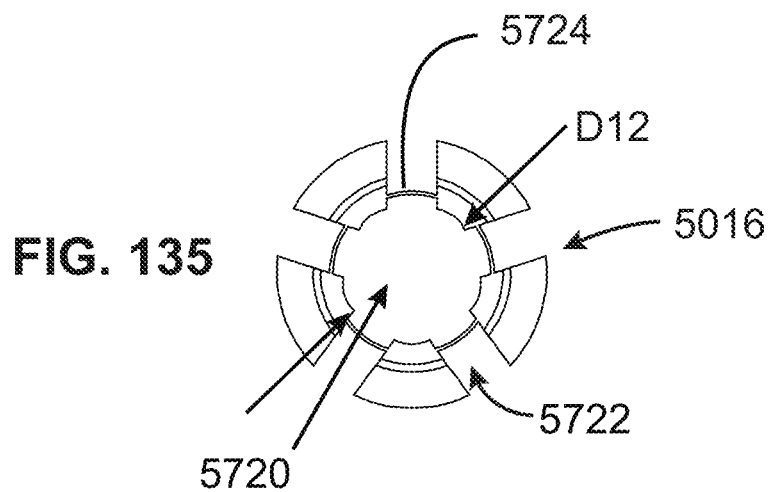
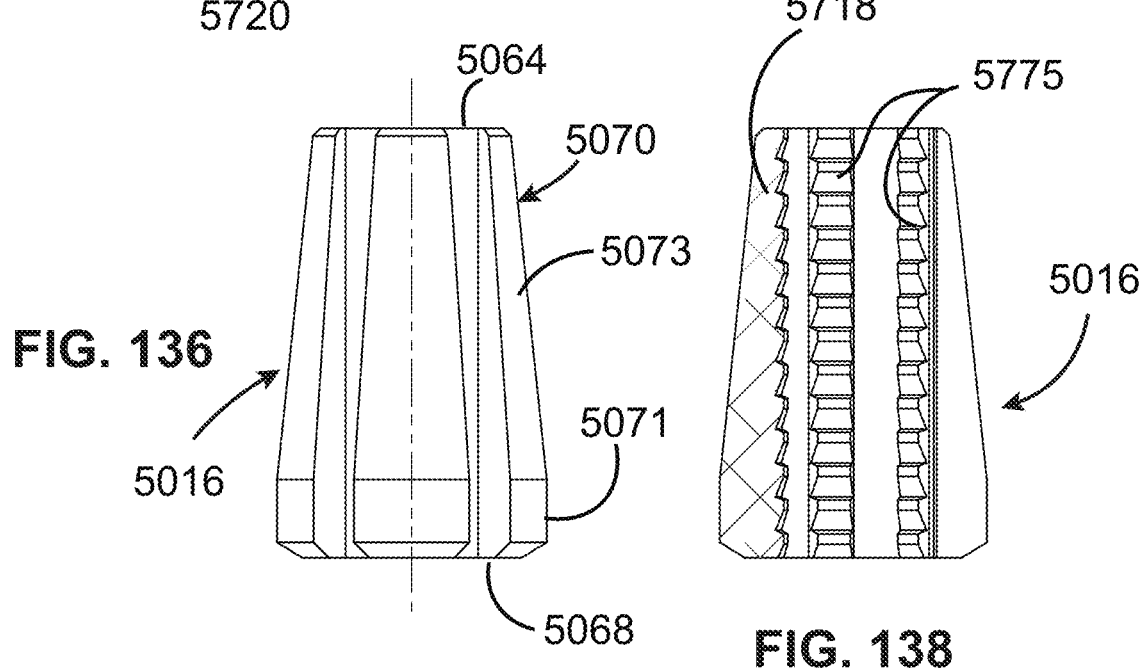
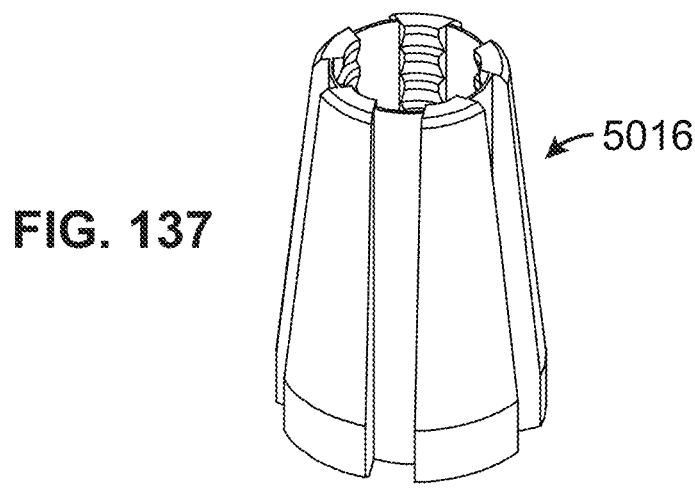

ANCHOR APPARATUS

BACKGROUND OF THE INVENTION

This invention relates generally to medical implants, and more particularly to a method for applying tension along or across a ligament to repair, augment, or replace it, or applying tension across a bone fracture to reduce it.

Medical implants for tensioning purposes typically comprise one or more tensile members (e.g., sutures or orthopedic cables) connected to one or more anchors (e.g., suture anchors or suture locks) to create a converging tensile force between the two anchors. This general concept has been used in the orthopedic and sports medicine fields to repair torn or damaged tendons and ligaments, to replace missing or displaced tendons and ligaments, and to anchor grafted or artificial tendons and ligaments to bones so that they can grow back together.

Prior art anchor/tensile member configurations typically fall into three functional categories; (1) a configuration in which the tensile member in held in place by an interference fit between the tensile member and bone, (2) a configuration in which the tensile member is tied, glued, melted, or otherwise connected to the anchor during manufacturing or intraoperatively, and (3) a configuration in which the tensile member is tensioned or made tight with the use of one of many available and well-known slip-knots.

It is often desirable to have the ability to tension the configuration provisionally (i.e. without setting a final irreversible tension) so that the effect of a particular level of tension can be evaluated and have the opportunity to "settle in" before it is made permanent.

However, one problem with prior art anchors is that they do not generally permit accurate provisional tensioning. When standard suture anchors are used, the tension is set by estimating the length of the final suture implant or tying a slipknot that can be tightened by hand. Some are even tensioned by wrapping the suture around a Kirschner wire ("K-wire") and twisting the wire to tighten. Even if the initial tension is estimated well, suture will settle into the soft tissue around it and lose tension after implantation. There does not currently exist a good way to tension a suture to a known load, "trial" its tension and allow for some settle in, re-tension, and repeat as needed.

Another problem with prior art suture tensioning techniques is that of determining that excessive tension is our applied. More specifically, because the tension in a suture strand does not exceed its failure load during the operative procedure does not mean it will not experience a load greater than its failure load during cyclic loading in-situ.

BRIEF SUMMARY OF THE INVENTION

At least one of these problems are addressed by a modular orthopedic device, and implant/instrument system, and method.

According to one aspect of the technology described herein, an anchor for anchoring one or more tensile members to bone includes: a housing extending along a central axis between open first and second ends, and having a hollow interior; a collet disposed in the hollow interior of the housing, the collet having a peripheral wall defining a central bore for accepting one or more tensile members therethrough and an exterior surface, wherein the collet is configured to be swaged around and against the one or more tensile members; a sleeve having a peripheral wall defining opposed interior and exterior surfaces, the sleeve disposed in the hollow interior of the housing and positioned generally axially adjacent to the collet, so as to be movable parallel to the central axis between first and second positions; and wherein at least one of the exterior surface of the collet and the interior surface of the sleeve is tapered and the sleeve and the collet are arranged such that movement of the sleeve from the first position to the second position will cause the interior surface of the sleeve to bear against the exterior surface of the collet, causing the collet to swage radially inwards around and against the one or more tensile members.

According to another aspect of the technology described herein, an apparatus for attaching a clamp for anchoring one or more tensile members includes: a clamp, including: a collet having a peripheral wall defining a central bore for accepting one or more tensile members therethrough and an exterior surface, wherein the collet is configured to be swaged around and against the one or more tensile members; a sleeve having a peripheral wall defining opposed interior and exterior surfaces, the sleeve positioned generally axially adjacent to the collet, so as to be movable parallel to a mutual central axis of the sleeve and the collet, between first and second positions; and wherein at least one of the exterior surface of the collet and the interior surface of the sleeve is tapered and the sleeve and the collet are arranged such that movement of the sleeve from the first position to the second position will cause the interior surface of the sleeve to bear against the exterior surface of the collet, causing the collet to swage radially inwards around and against the one or more tensile members; and an insertion instrument including: two or more moveable jaws cooperatively defining a housing extending along a central axis between open first and second ends, and having a hollow interior sized to receive the clamp; and a driving mechanism operable to move the sleeve from the first position towards the second position.

According to another aspect of the technology described herein, an insertion instrument is configured to implant a tensile member anchor which includes a housing containing a collet and a sleeve. The insertion instrument includes: a body configured to be connected to the housing; a hollow pushrod extending through the stem and slidably movable between retracted and extended positions; a driving mechanism operable to move the pushrod between the retracted and extended positions; and a tensioner including a housing coupled to the body of the insertion instrument, the housing including two or more sub-housings each including a yoke which is configured to engage a tensile member and which is selectively movable relative to the sub-housing, wherein each of the yokes is movable independently of the other yokes.

BRIEF DESCRIPTION OF THE DRAWINGS

The invention may be best understood by reference to the following description taken in conjunction with the accompanying drawing figures in which:

FIG. 9 is a schematic cross-sectional view of a housing having female threads engaging an instrument having male threads;

FIG. 10 is a schematic cross-sectional view of a housing having male threads engaging an instrument having female threads;

FIGS. 11 and 12 are schematic cross-sectional views of a housing having bayonet fitting slots engaging bayonet lugs of a corresponding instrument;

FIGS. 13 and 14 are schematic cross-sectional and top plan views, respectively of a housing having a circumferential slot engaging axial lugs of a corresponding instrument;

FIG. 15 is a schematic cross-sectional view of a housing having a counterbore formed therein engaging collet jaws of a corresponding instrument;

FIGS. 21 and 22 are schematic cross-sectional and end views, respectively, of a collet having a slotted construction;

FIGS. 23 and 24 are schematic cross-sectional and end views, respectively, of a collet having curvilinear slots formed therein;

FIGS. 25 and 26 are schematic cross-sectional and end views, respectively, of a collet having a spring structure;

FIG. 40 is a schematic side elevation view of an exemplary housing assembled with a snap-on cap;

FIG. 41 is a sectional view of the housing and cap of FIG. 40;

FIG. 42 is a schematic exploded perspective view of an exemplary housing assembled with a screw-on cap;

FIG. 43 is a sectional view of the housing and cap of FIG. 42;

FIG. 53 is a schematic cross-sectional view of a distal end of a stem of an alternative installation instrument of, showing an anchor ready to be loaded therein;

FIG. 54 is a view of the stem of FIG. 53, showing an anchor lightly received in jaws of the stem, with a locking sleeve retracted;

FIG. 55 is another view of the stem of FIG. 53, showing a locking sleeve pushed down over the jaws to secure the anchor;

FIGS. 56 and 57 are sequential views showing actuation of a pushrod of the stem of FIG. 49;

FIG. 58 is another view of the stem of FIG. 49, showing a clip in a released position, with the jaws opened to release the anchor;

FIG. 72 is a partially cutaway perspective view of an alternative embodiment of an anchor;

FIG. 73 is a side view of the anchor of FIG. 72;

FIG. 88 is a schematic perspective view of a tensile member cutting instrument;

FIG. 89 is a cross-sectional view of a portion of the cutting instrument of FIG. 88 in an open position;

FIG. 90 is a cross-sectional view of a portion of the cutting instrument of FIG. 88 in a closed position;

FIGS. 109A and 109B are schematic views of the lateral and medial aspects, respectively of the human foot, showing a double bundle ligament augmentation;

FIG. 118 is a schematic side view of a clamp for a cerclage repair;

FIG. 119 is a schematic cross-sectional view of the clamp of FIG. 118;

FIG. 120 is a schematic exploded perspective view of an alternative clamp for a cerclage repair;

FIG. 121 is a cross-sectional view of the clamp of FIG. 120;

FIG. 122 is a schematic perspective view of the human femur having a cerclage applied thereto;

FIG. 123 is a schematic perspective view of a self-tracking reamer;

FIG. 133 is a sectioned perspective view of a portion of the anchor of FIG. 130, showing a breakaway structure thereof;

FIG. 134 is an enlarged view of a portion of FIG. 133;

FIG. 135 is an end view of a collet shown in FIG. 131;

FIG. 136 is a side elevation view of the collet of FIG. 135;

FIG. 137 is a perspective view of the collet of FIG. 135;

FIG. 138 is a cross-sectional view of the collet shown in FIG. 135;

FIGS. 139-142 are views showing the collet of FIGS. 135-138 in a swaged condition;

FIGS. 143-147 are views showing an alternative collet;

FIGS. 148-151 are views showing another alternative collet;

FIG. 152 is a schematic cross-sectional view of the anchor of FIG. 130 coupled to an insertion device, prior to a swaging operation;

FIG. 153 is a schematic cross-sectional view of the anchor of FIG. 130, upon completion of a swaging operation;

FIG. 154 is a schematic cross-sectional view of the anchor of FIG. 130, subsequent to completion of a swaging operation, showing an extension portion of the housing of anchor being separated from the remainder of the anchor;

Figure 155:
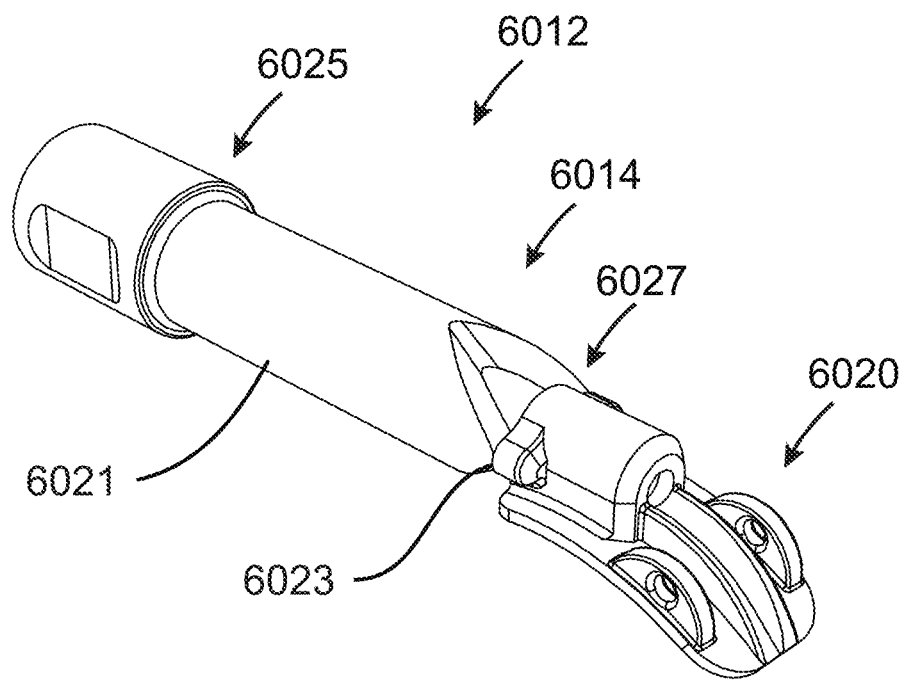
Figure 156:
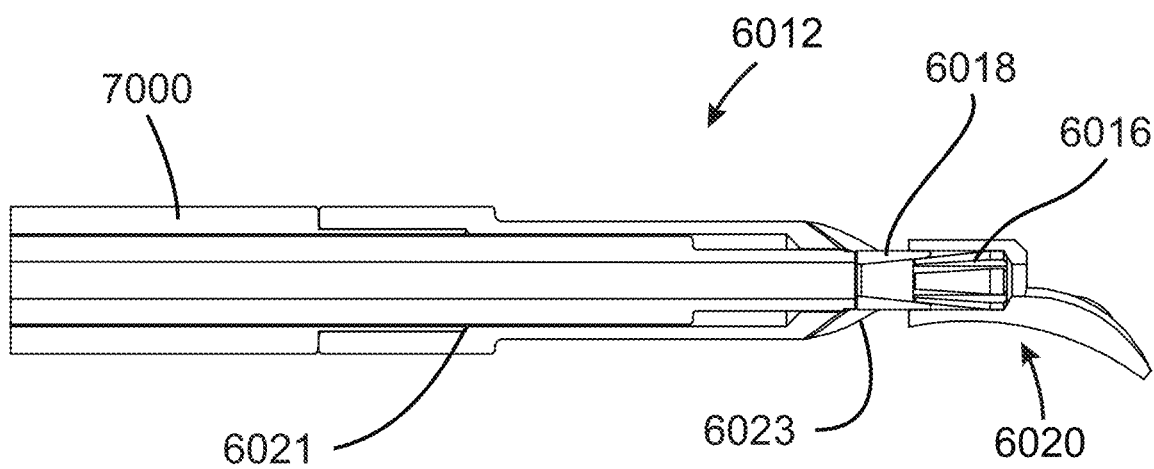
Figure 157:
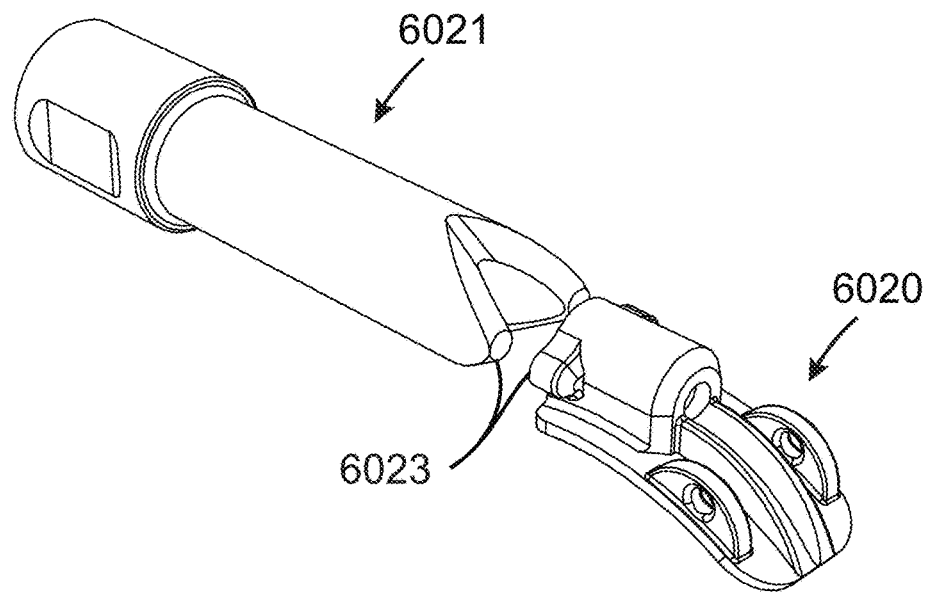
Figure 158:
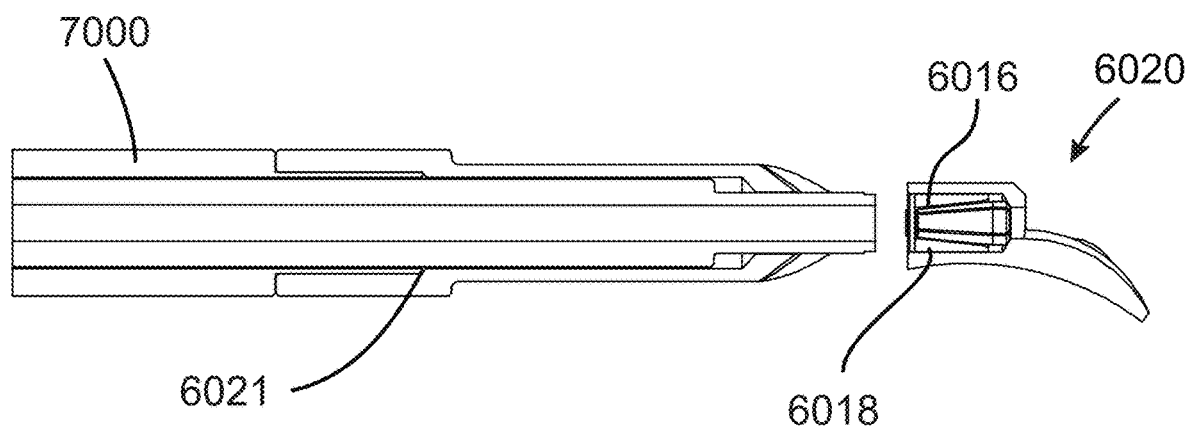
Figure 159:
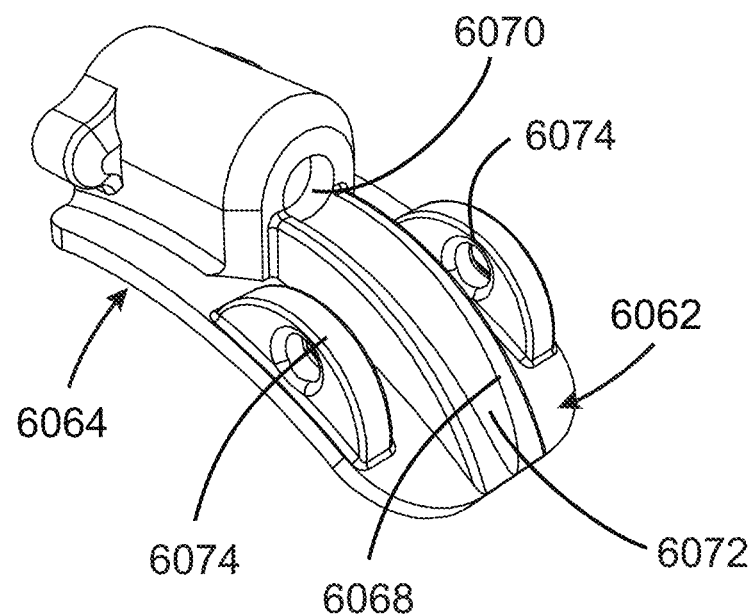
Figure 160:
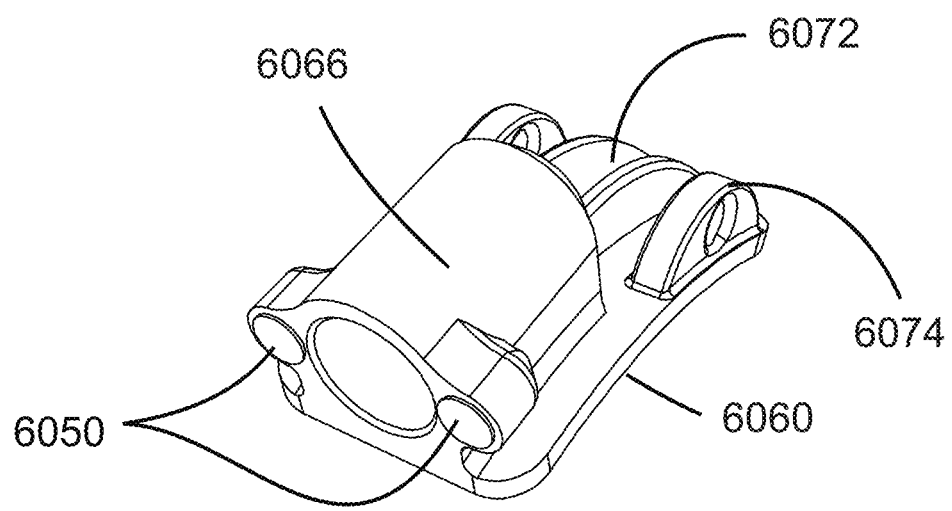
Figures 161, 162:
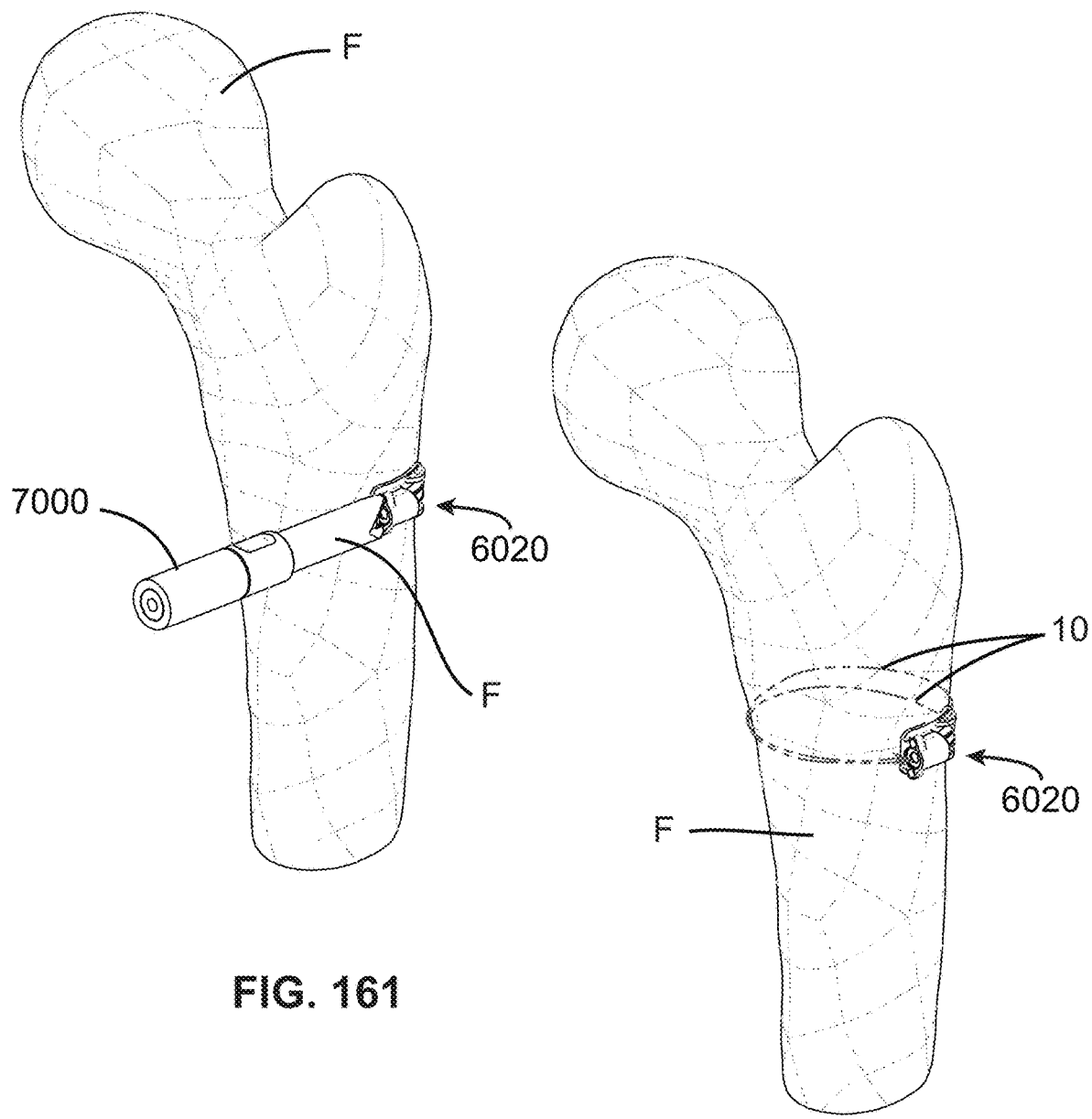
Figure 163:
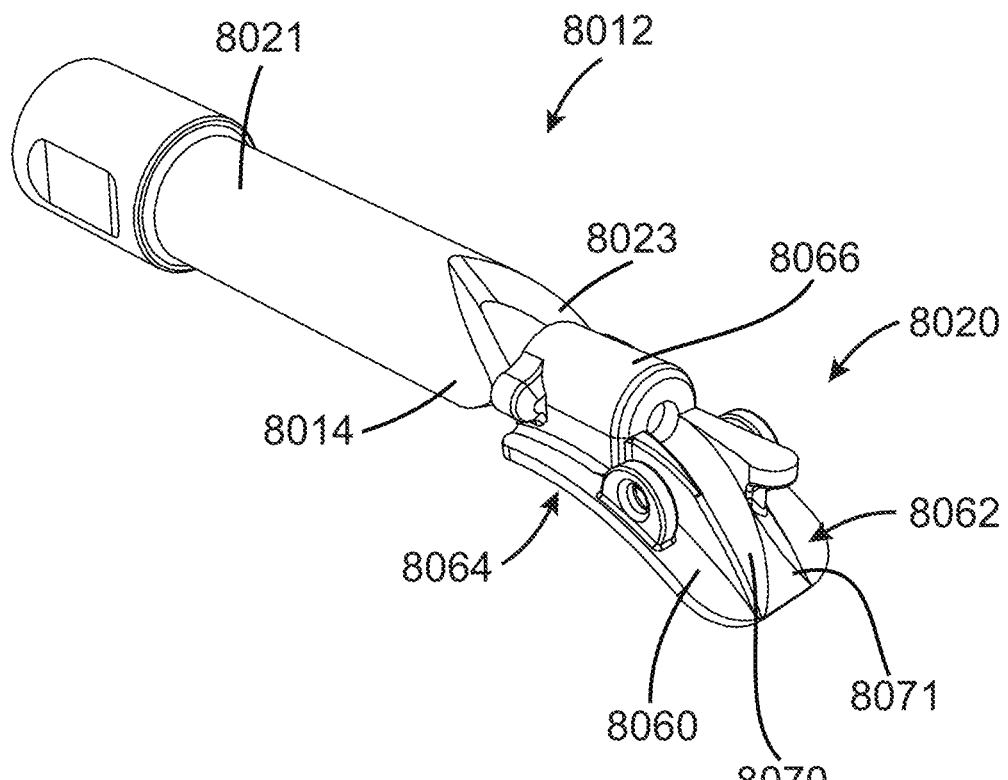
Figure 164:
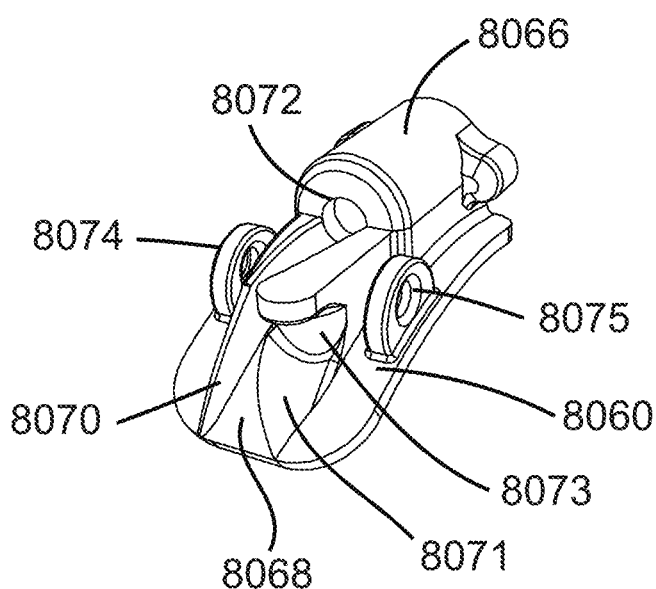
Figure 165:
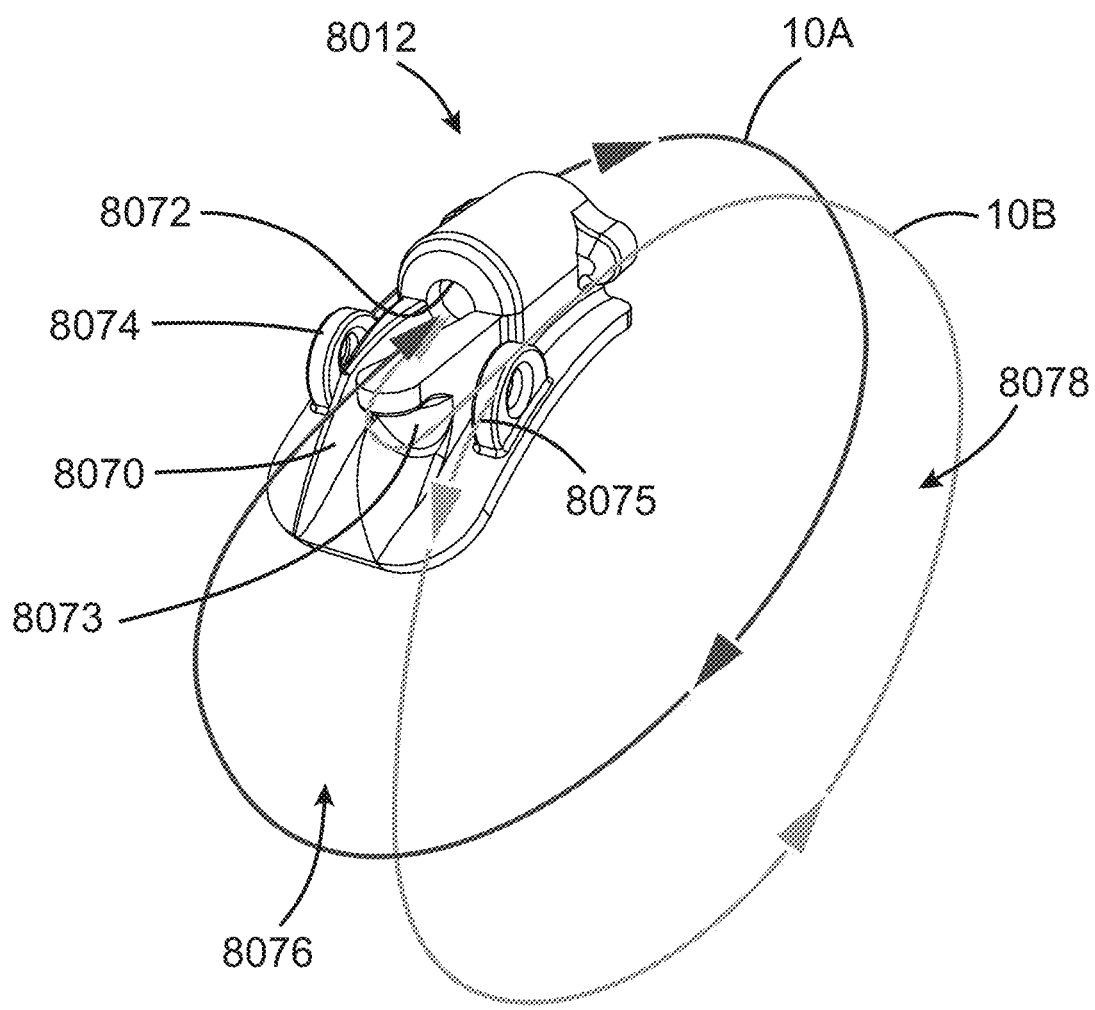
Figure 166:
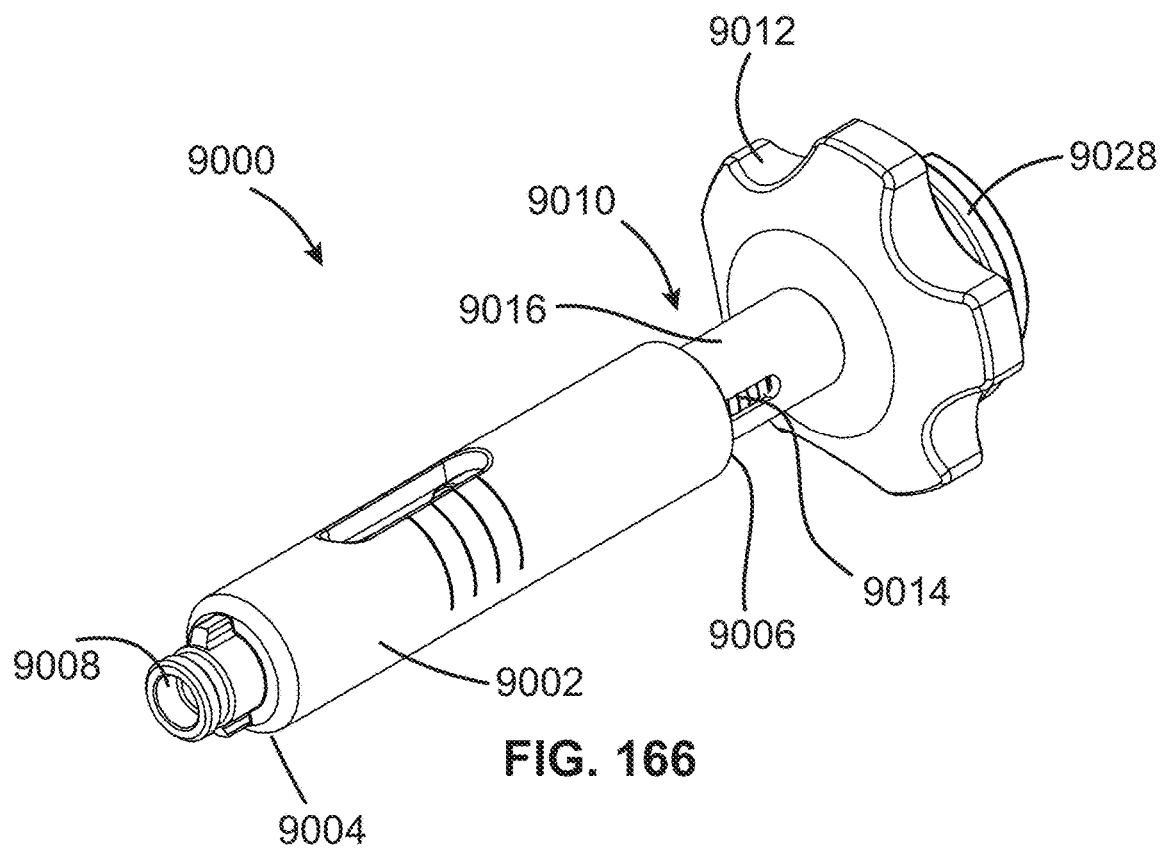
Figure 167:
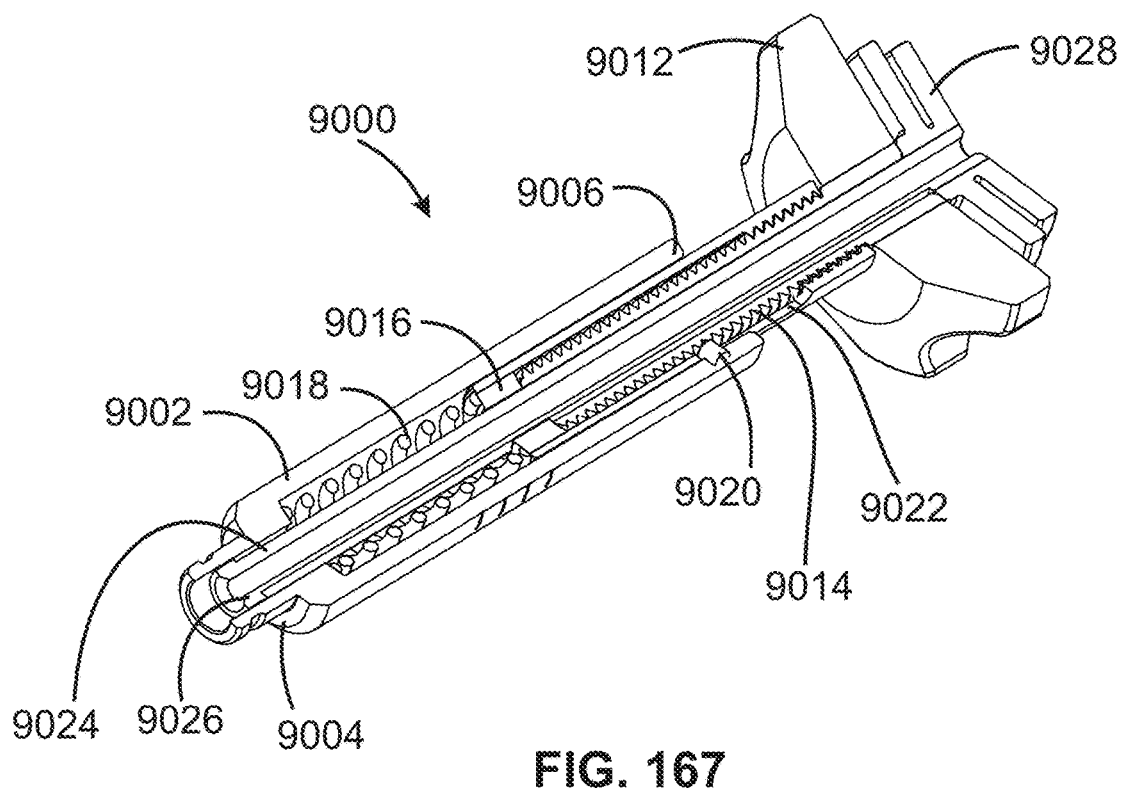

FIG. 155 is a schematic side view of an alternative clamp for a cerclage repair;

FIG. 156 is a cross-sectional view of the clamp of FIG. 155;

FIG. 157 is a perspective view of the clamp of FIG. 155, in a separated condition;

FIG. 158 is a cross-sectional view of the separated clamp of FIG. 157;

FIG. 159 is a perspective view of a body portion of the clamp of FIG. 155;

FIG. 160 is another perspective view of the body portion of FIG. 159;

FIG. 161 is a schematic perspective view of the human femur having the clamp of FIG. 155 placed thereon, in preparation for the application of a cerclage; and FIG. 162 is a schematic perspective view of the human femur having a cerclage applied thereto;

FIG. 163 is a schematic perspective view of an alternative clamp for a cerclage repair;

FIG. 164 is another perspective view of the clamp of FIG. 163;

FIG. 165 is a schematic perspective view of the clamp of FIG. 163 being used to apply a cerclage;

FIG. 166 is a schematic perspective view of an exemplary tensioner;

FIG. 167 is a partially cut away perspective view of the tensioner of FIG.

Figure 168:
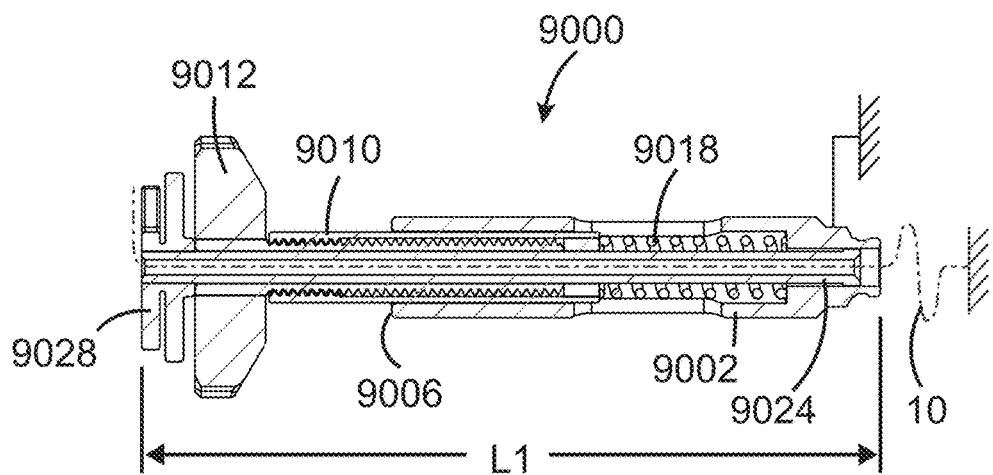
Figure 169:
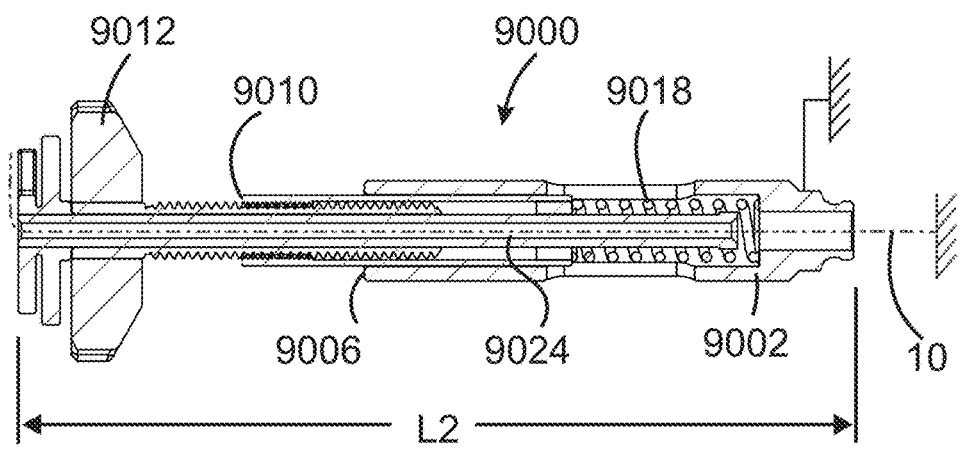
Figure 170:
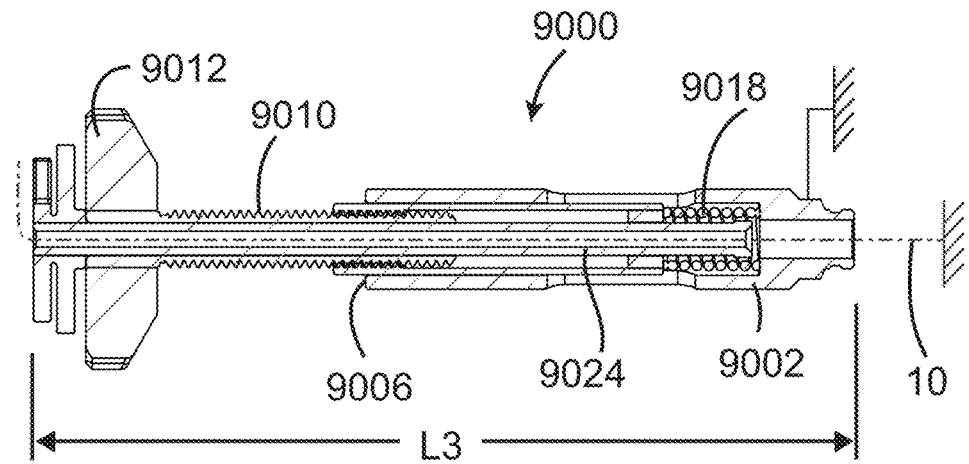
Figure 171:
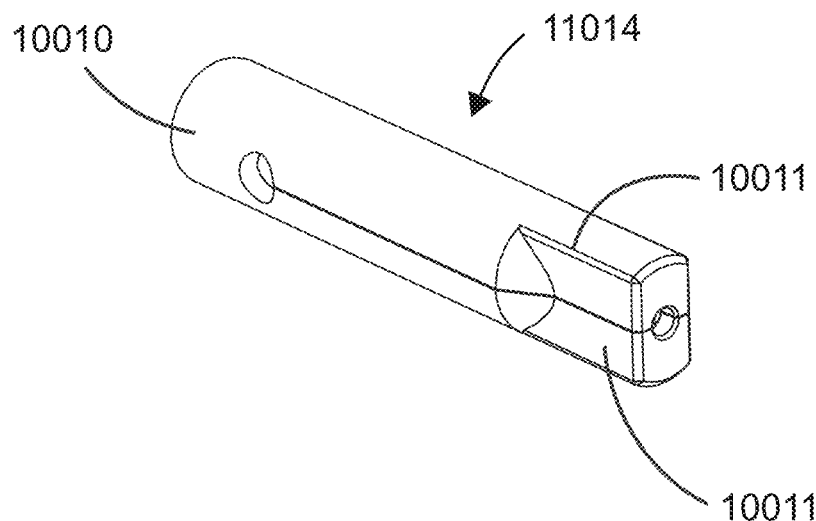
Figure 172:
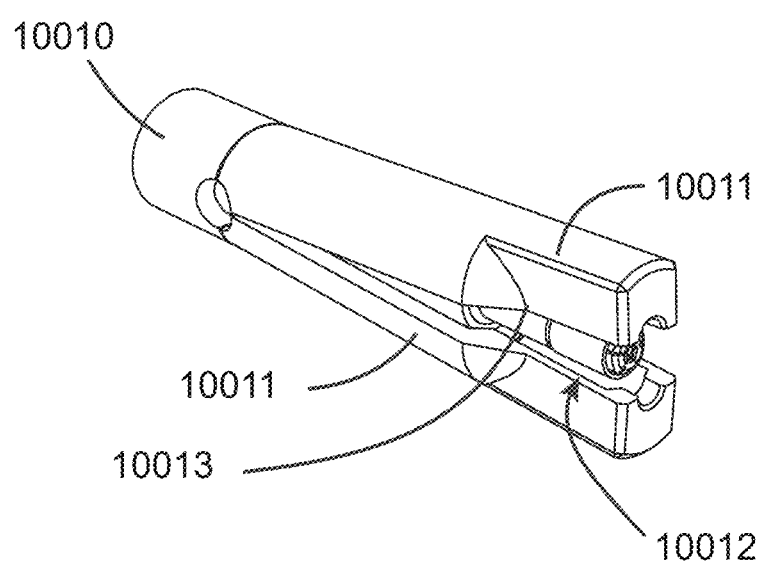
Figure 173:
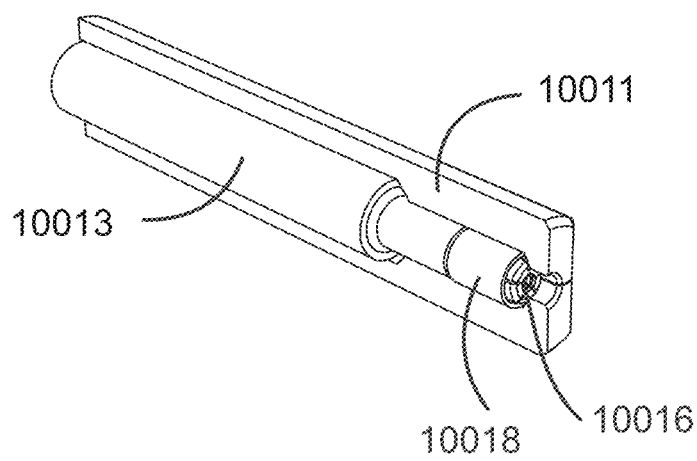
Figures 174, 175:
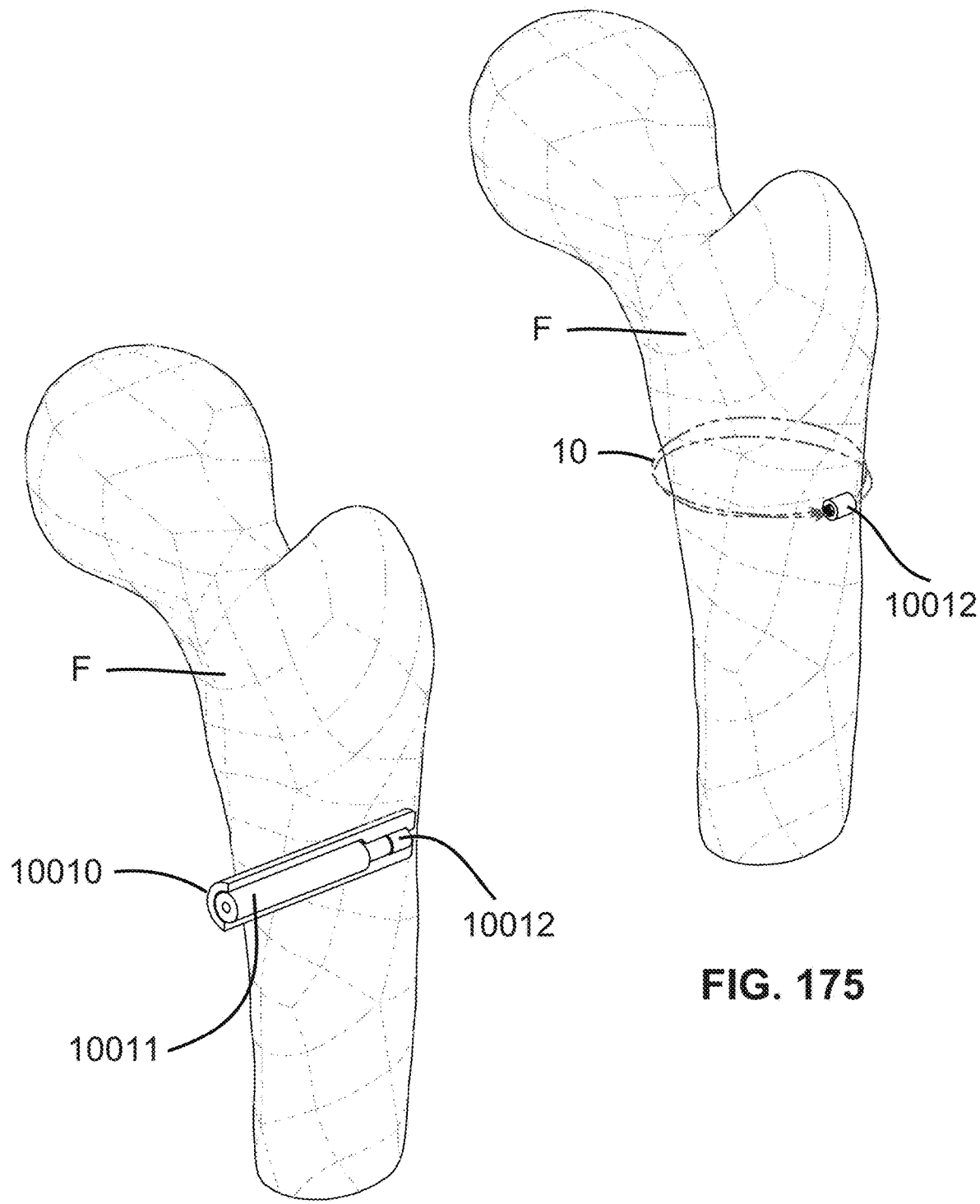
Figure 176:
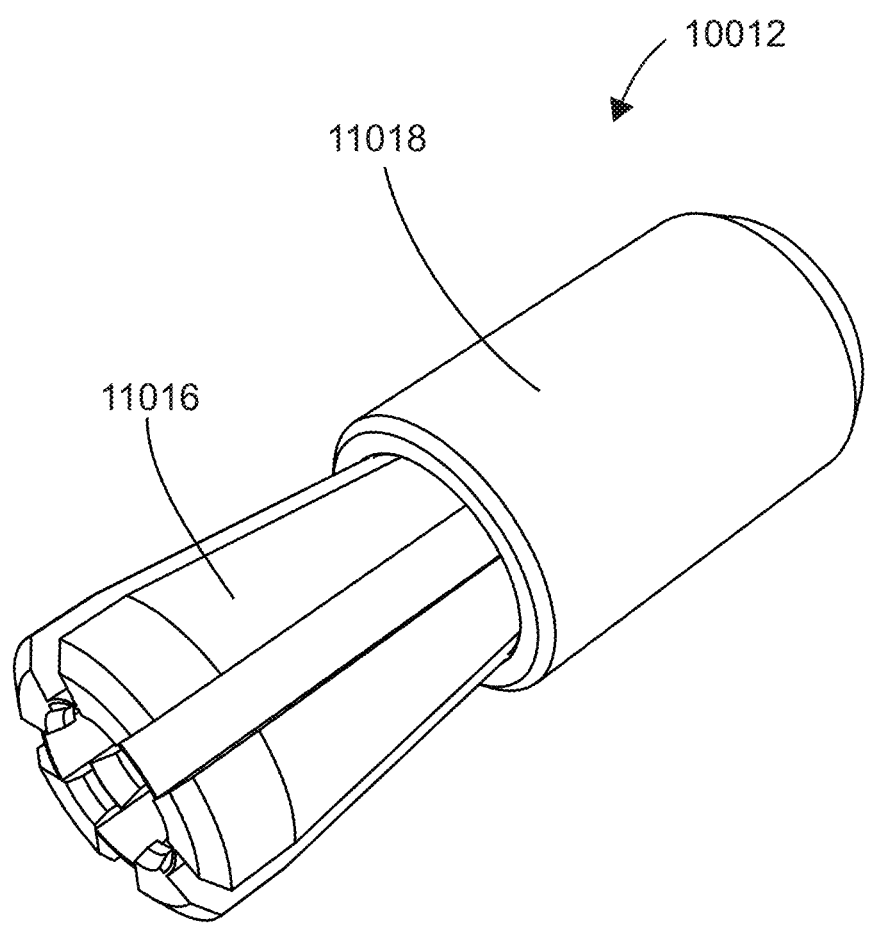
Figure 177:
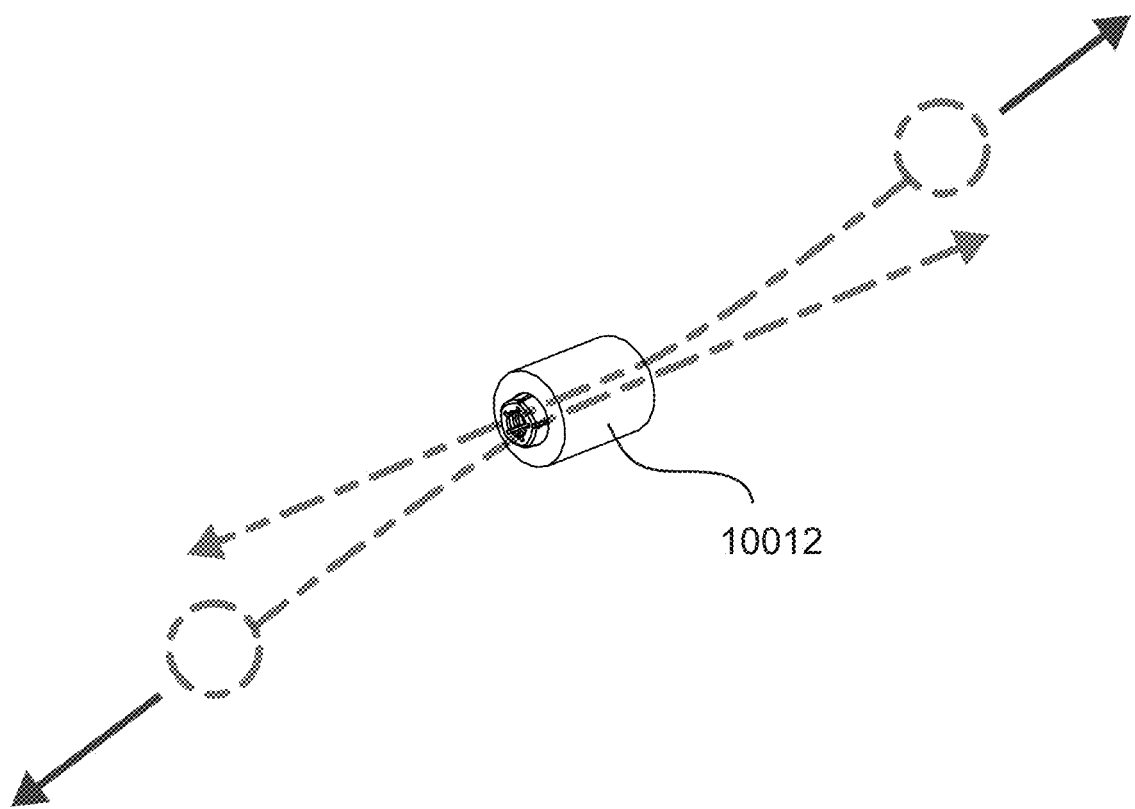
Figure 178:
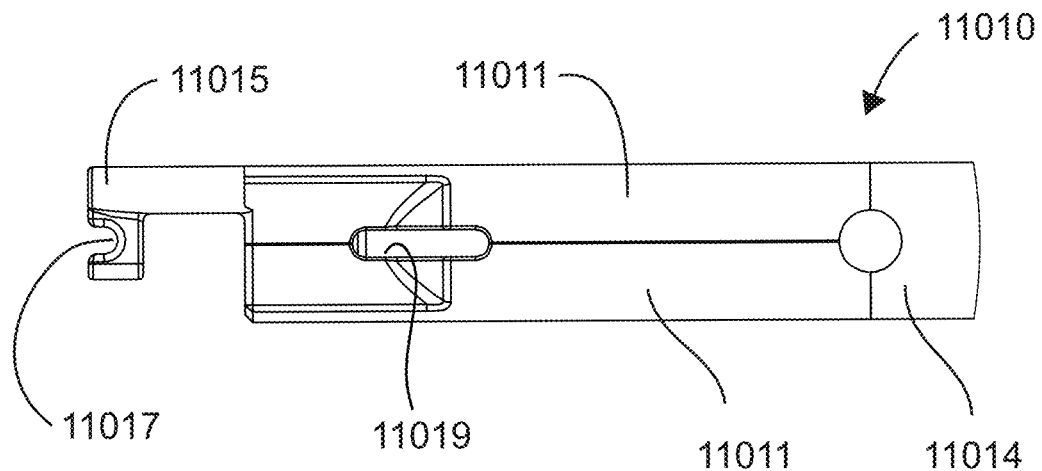
Figure 179:
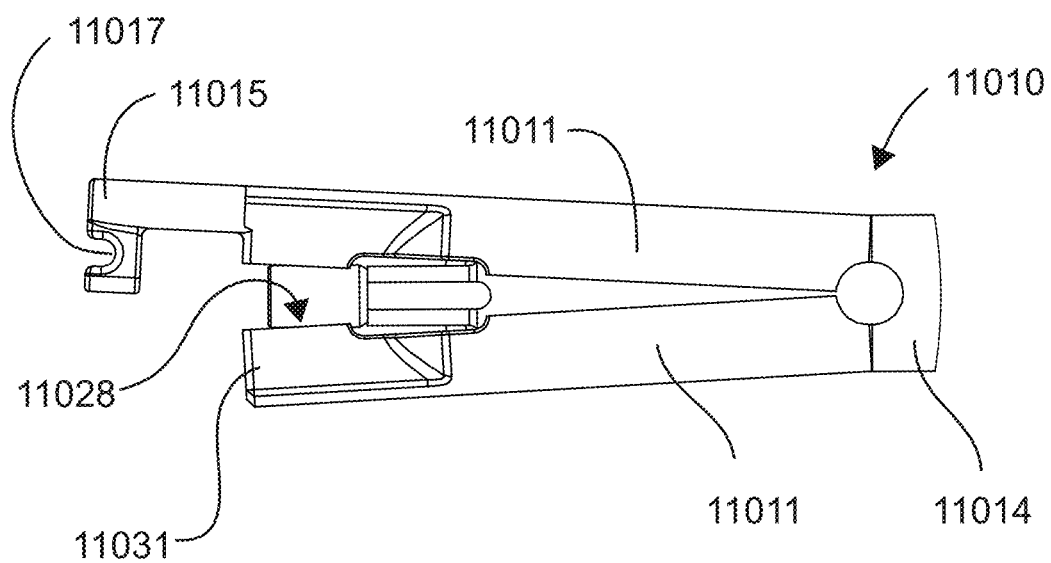
Figure 180:
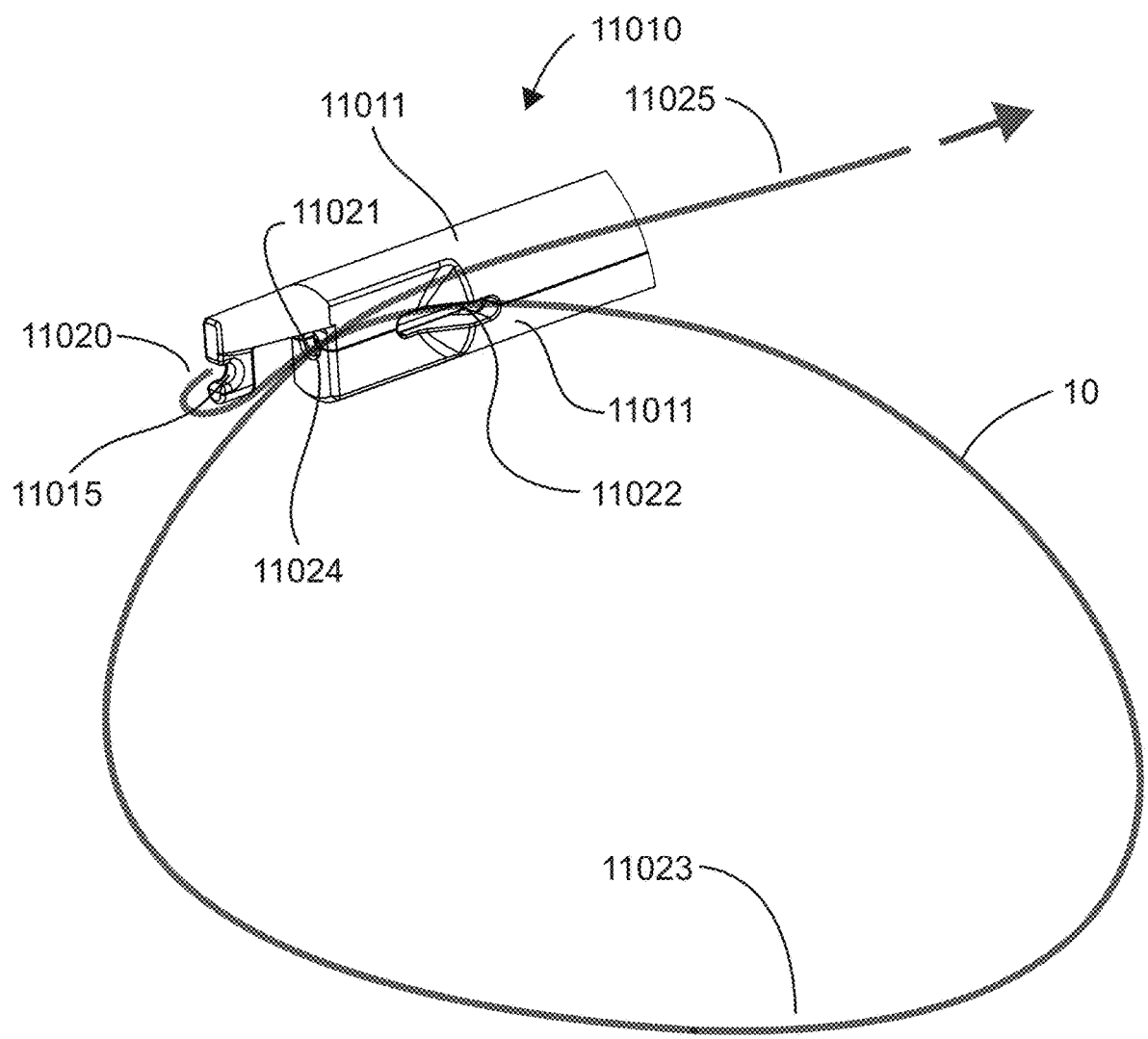
Figure 181:
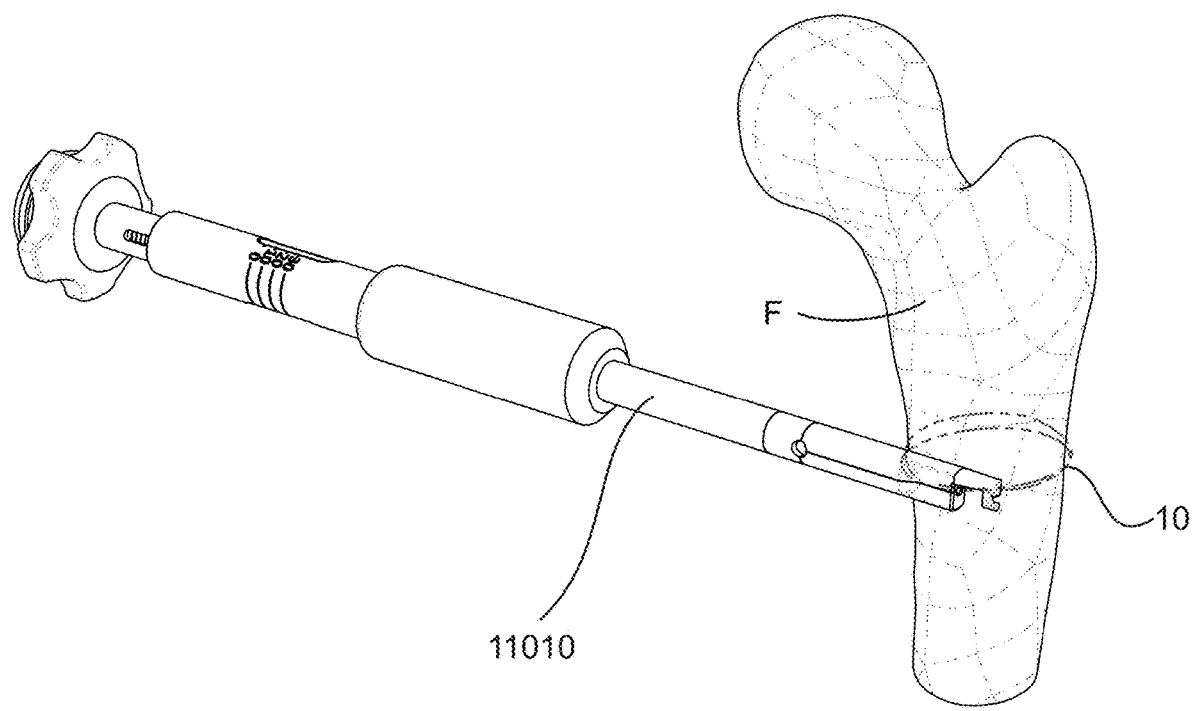
Figure 182:
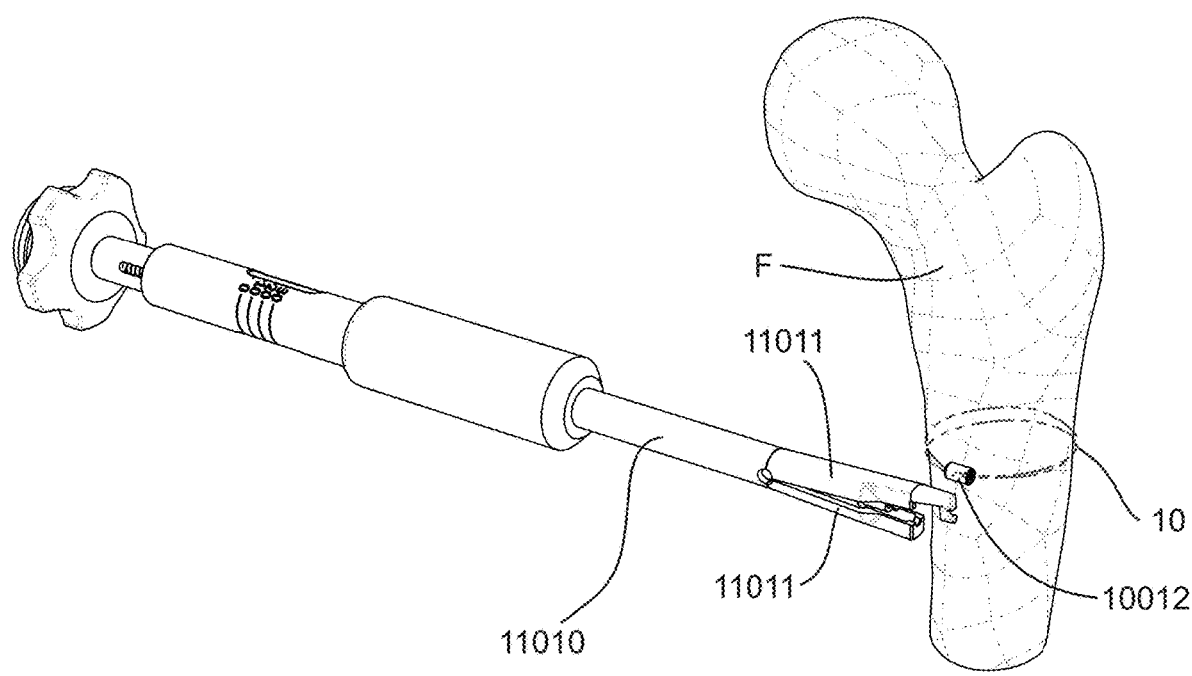
Figure 183:
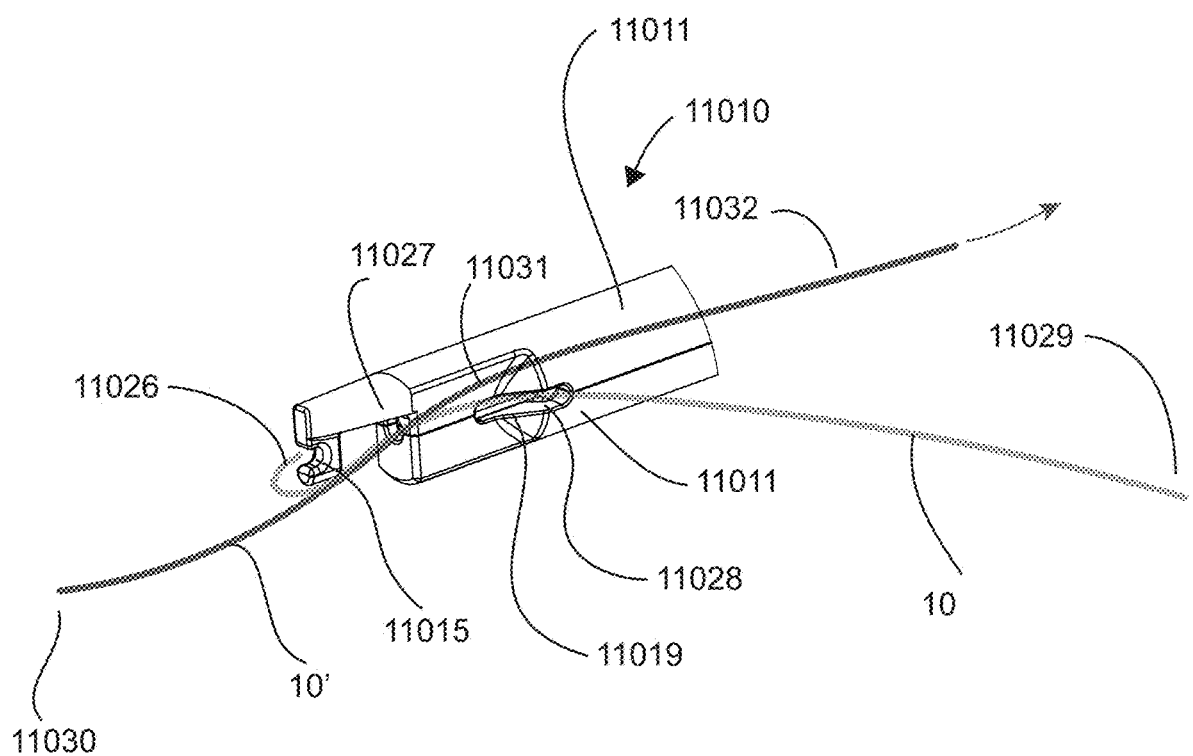
Figure 184:
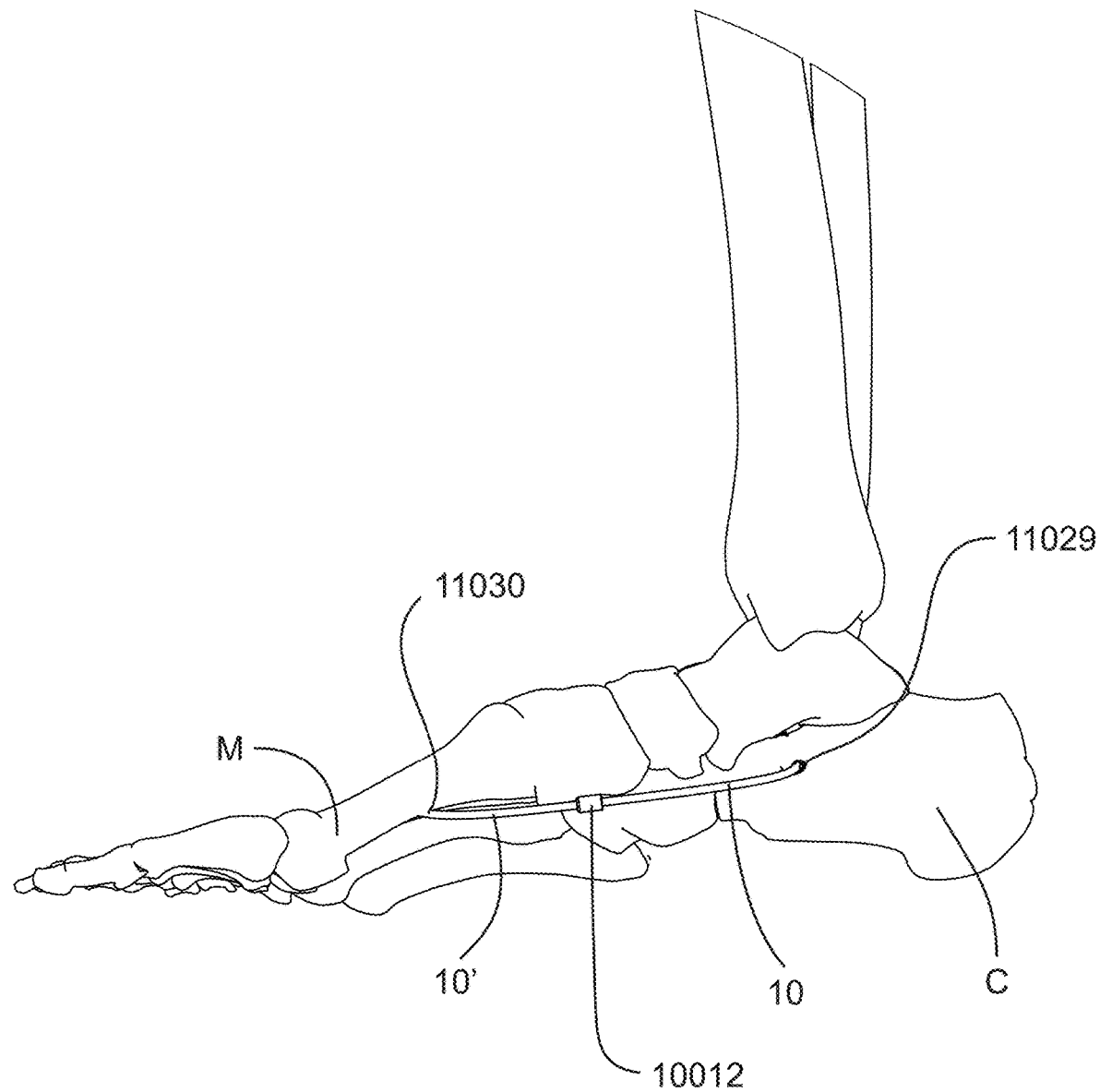
Figure 185:
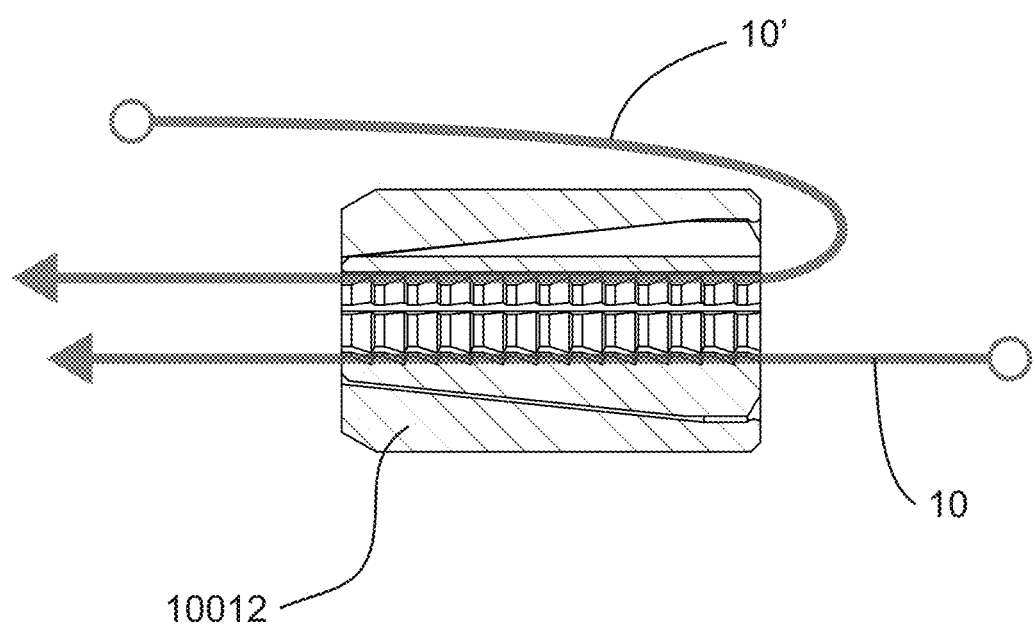
Figure 186:
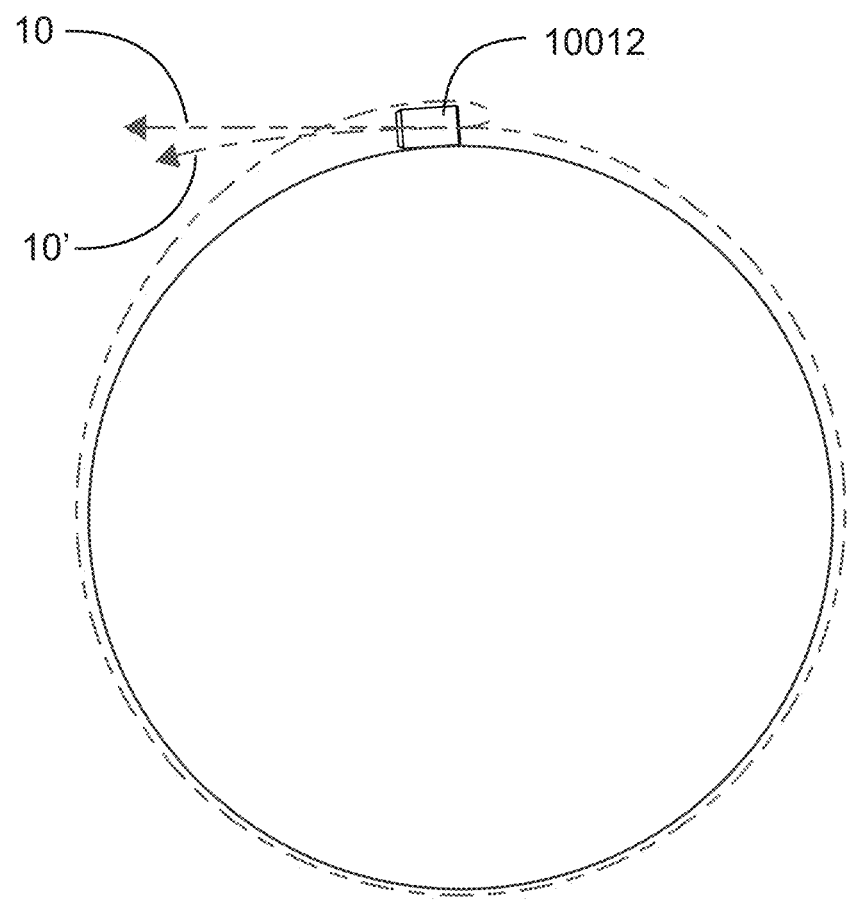
Figure 187:
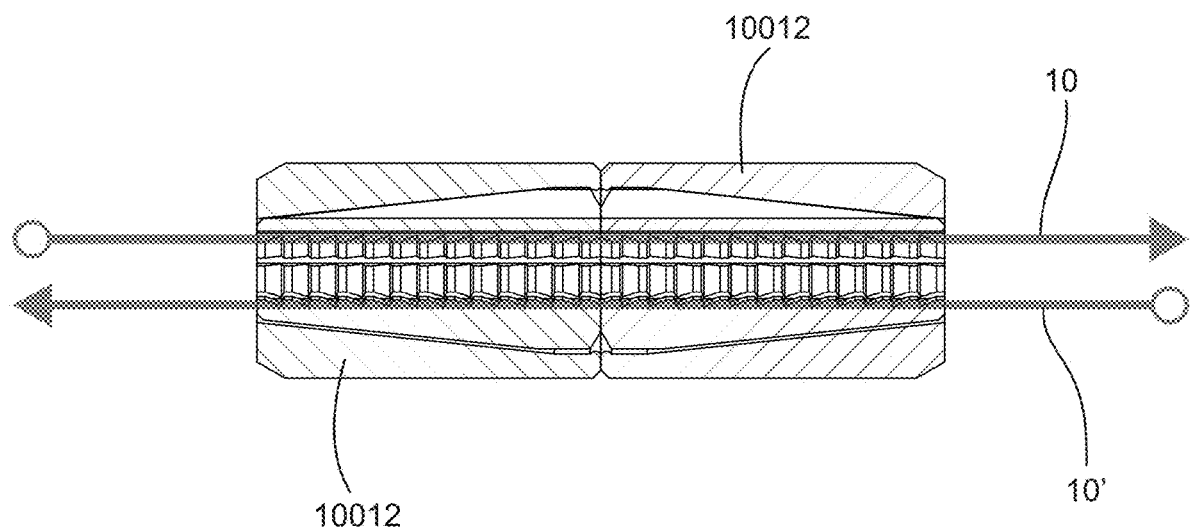
Figure 188:
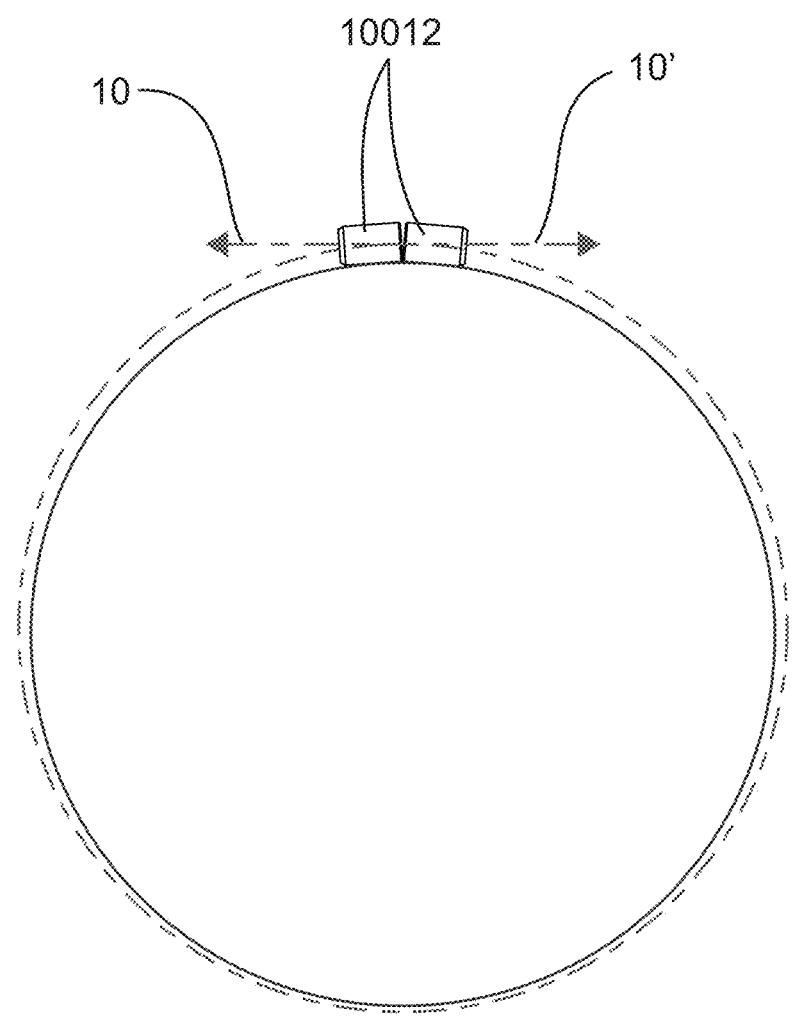

FIG. 168 is a sectional view of the tensioner of FIG. 166 during a first step of a tensioning process;

FIG. 169 is a sectional view of the tensioner of FIG. 166 during a second step of a tensioning process;

FIG. 170 is a sectional view of the tensioner of FIG. 166 during a third step of a tensioning process;

FIG. 171 is a schematic perspective view of an alternative clamp and instrument for a cerclage repair, in a closed position;

FIG. 172 is another perspective view of the clamp and instrument of FIG. 171, in an open position;

FIG. 173 is a partially-sectioned view of the clamp of FIG. 171;

FIG. 174 is a schematic perspective view of the human femur having the clamp of FIG. 171 placed thereon, in preparation for the application of a cerclage; and FIG. 175 is a schematic perspective view of the human femur having a cerclage applied thereto;

FIG. 176 is a schematic perspective view of the clamp seen in FIG. 173, in a condition prior to swaging;

FIG. 177 is a schematic perspective view of the clamp of FIG. 176, subsequent to swaging;

FIG. 178 is a schematic perspective view of an alternative instrument for a cerclage repair, in a closed position;

FIG. 179 is another perspective view of the instrument of FIG. 178, in an open position;

FIG. 180 is a schematic diagram illustrating an instrument and clamp configured for a cerclage application;

FIG. 181 is a schematic diagram illustrating an instrument in the process of applying a cerclage to a human femur bone;

FIG. 182 is a schematic diagram illustrating a completed cerclage as applied in FIG. 181;

FIG. 183 is a schematic diagram illustrating an instrument and clamp configured for an in-line application;

FIG. 184 is a schematic diagram illustrating an in-line application of the tensile member using a clamp;

FIG. 185 is a cross-sectional diagram of a clamp securing a pair of tensile members;

FIG. 186 is a schematic diagram showing the clamp of FIG. 185 is applied in a cerclage application;

FIG. 187 is a cross-sectional diagram of a pair of clamps arranged in tandem, securing a pair of tensile members; and FIG. 188 is a schematic diagram showing the clamps of FIG. 187 in a cerclage application.

DETAILED DESCRIPTION OF THE INVENTION

In general, the technology described herein provides a modular device and implant system and method that enables provisional and permanently stable tensioning of the tensile member, with minimally-invasive access to and limited visualization of the bone surface, using a device that is small and low-profile to prevent stress-shielding and soft tissue hang-up, implanted by simple and intuitive instrumentation that optimizes workflow and can be accomplished by one person.

Figure 1:
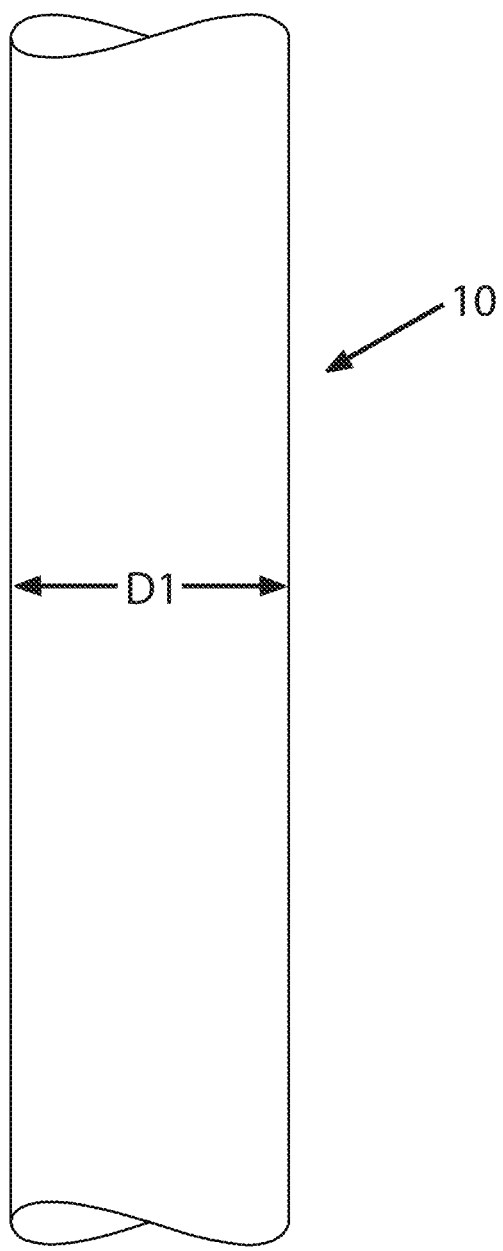
FIG. 1 is a schematic side elevation view of a segment of a prior art tensile member.

The anchor, installation system, and installation method described herein are suitable for receiving and securing a tensile member to bone. The term "tensile member" as used herein generally refers to any flexible element capable of transmitting a tensile force. Nonlimiting examples of known types of tensile members include sutures and orthopedic cables. FIG. 1 illustrates a short segment of a representative tensile member 10 having a diameter "D1". Commercially-available tensile members intended to be implanted in the human body may have a diameter "D1" ranging from tens of microns in diameter to multiple millimeters in diameter. Commercially-available tensile members may be made from a variety of materials such as polymers or metal alloys. Nonlimiting examples of suitable materials include absorbable polymers, nylon, ultrahigh molecular weight polyethylene ("UHMWPE") or polypropylene titanium alloys, or stainless steel alloys. Known physical configurations of tensile members include monofilament, braided, twisted, woven, and wrapped. Optionally, the tensile member 10 may be made from a shape memory material, such as a temperature-responsive or moisture-response material.

Figure 2:
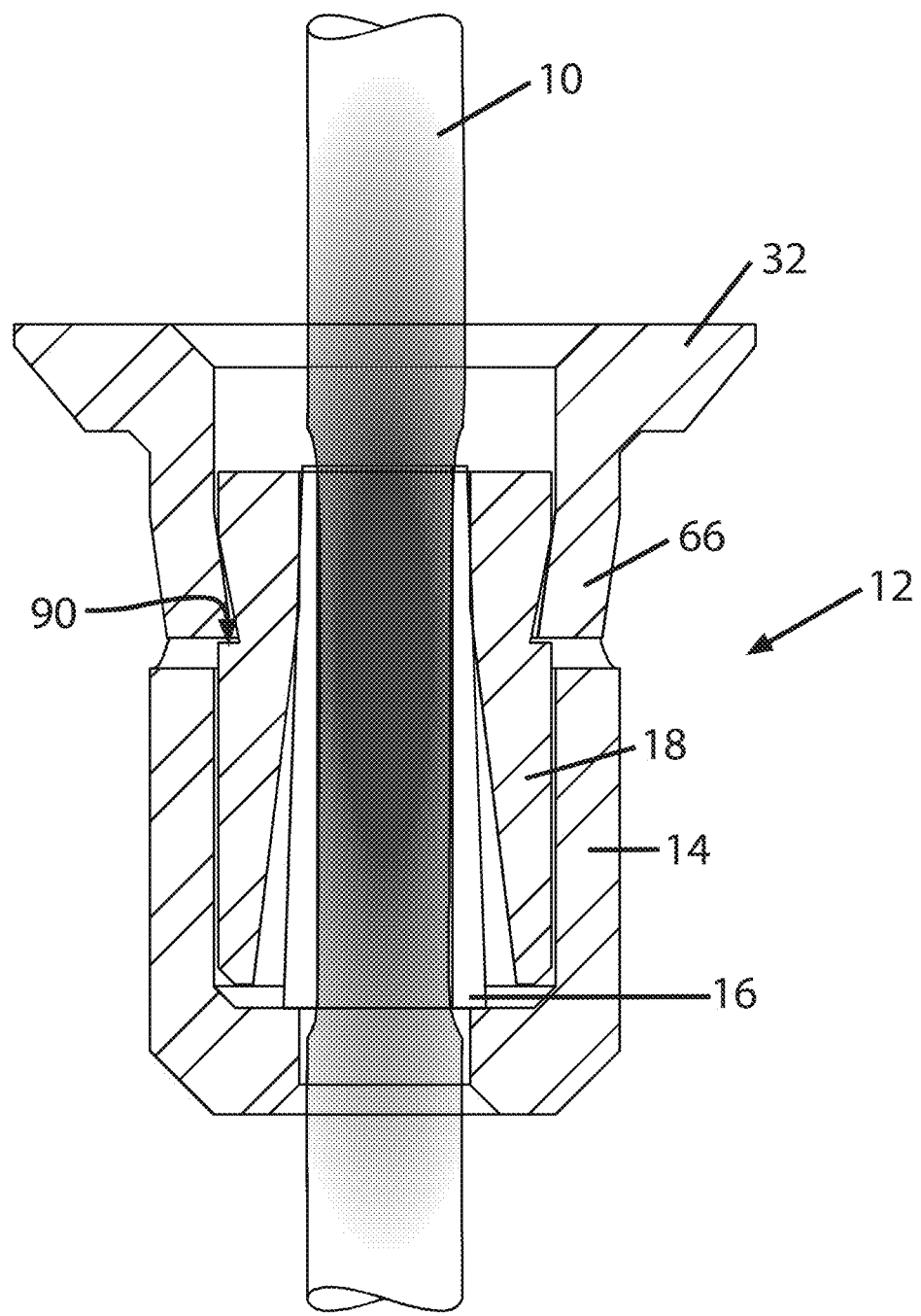
FIG. 2 is cross-sectional view of an assembled anchor with a tensile member engaged therein.
Figure 3:
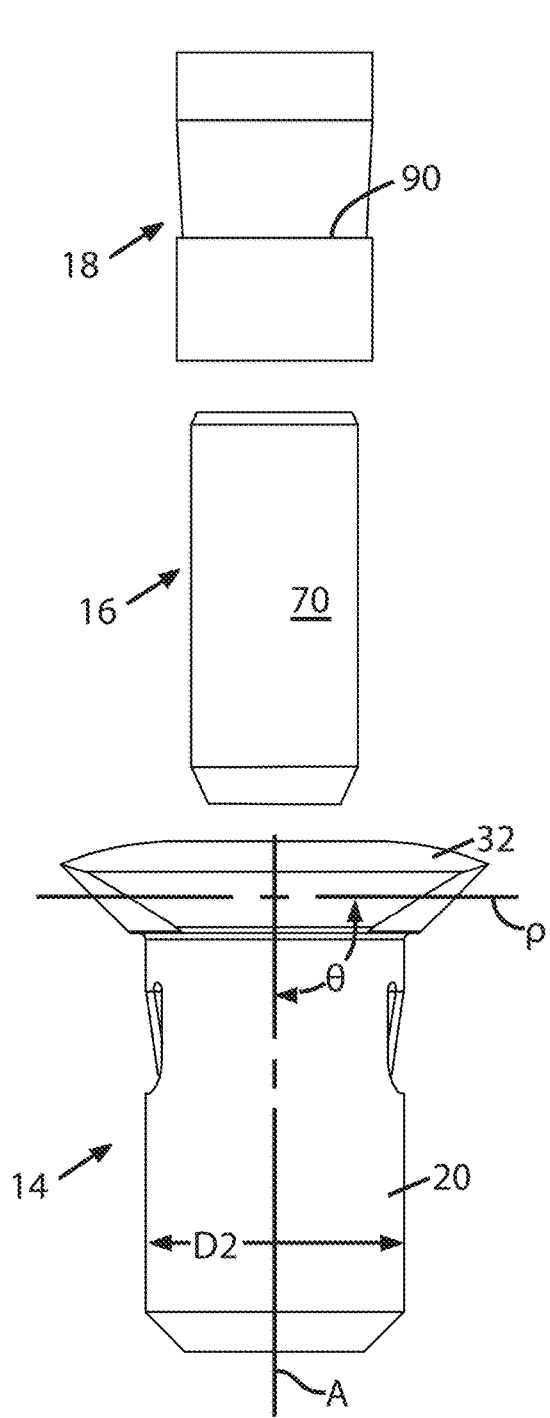
FIG. 3 is an exploded view of the anchor of FIG. 2.

FIG. 2 illustrates an exemplary embodiment of an anchor 12. The anchor 12 includes three functional elements, namely a housing 14 configured to be implanted into bone, a collet 16 received in the housing 14 and configured to be swaged around and against a tensile member 10 without moving axially relative to the housing 14 or tensile member 10, and a sleeve 18 received in the housing 14 which is capable of moving axially within the housing 14 so as to swage the collet 16, thus retaining the tensile member 10. (Some minimal axial movement of the collet 16 not significantly affecting tension may occur during swaging). Each of these basic elements is described in detail below with reference to FIGS. 3 and 4.

The housing 14 has a body 20 extending along a central axis "A" between first and second ends 22, 24. The body 20 is defined by a peripheral wall 26 having interior and exterior surfaces 28, 30 respectively, and defining a hollow interior 29. In the illustrated example, the body 20 is generally cylindrical in shape. The first and second ends 22, 24 of the body 20 may be chamfered and/or radiused as illustrated or otherwise shaped to ease insertion into bone. The first end of the body 22 has an internal flange 31 which is sized to define a stop against axial motion of the collet 16.

Figure 4:
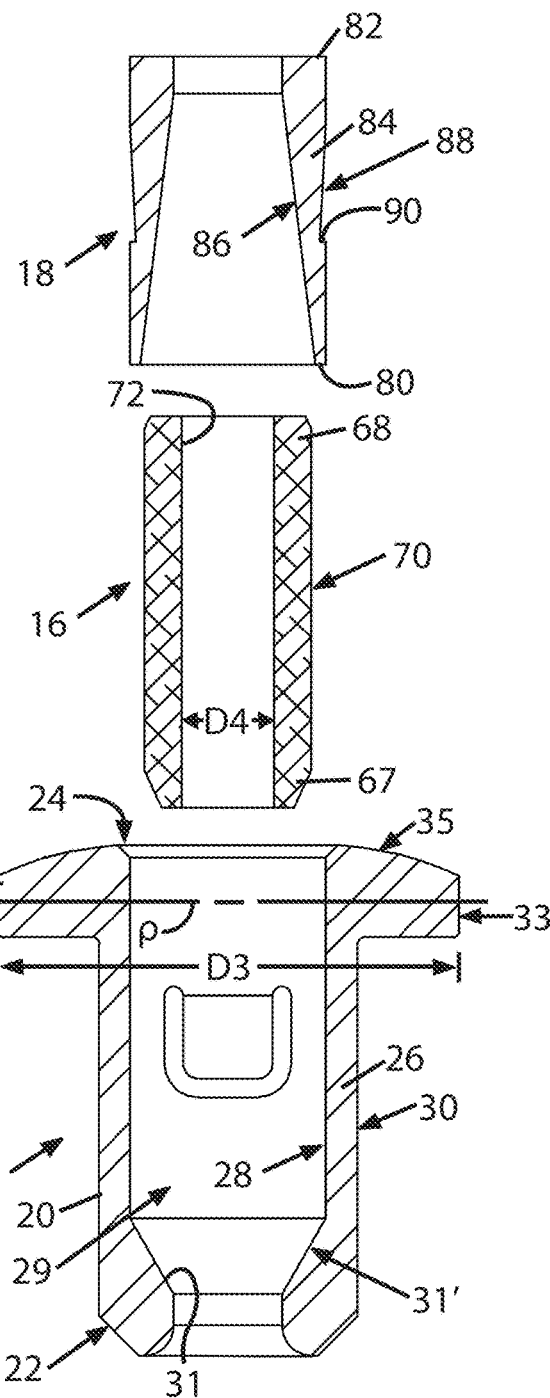
FIG. 4 is a cross-sectional view of FIG. 3.
Figure 5:
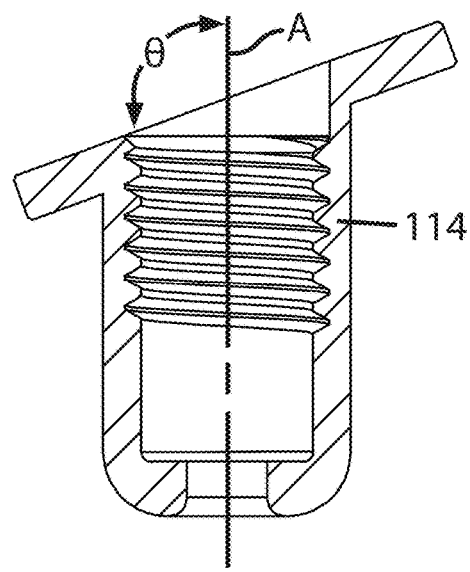
FIG. 5 is a schematic cross-sectional view of a housing having a flange disposed at an oblique angle.

A generally annular flange 32 is located at or near the second end 24 and extends radially outwards from the body 20. The flange 32 defines lateral and axial surfaces 33, 35 respectively. The size and shape of the flange 32 may be selected to suit a particular application. In the example illustrated in FIG. 4, a reference plane "P" passing through the flange 32 is oriented at an angle θ perpendicular to the central axis A. It will be understood that the orientation of the flange may be varied to suit a particular application. For example, FIG. 5 shows a housing 114 in which the angle θ is oblique to the central axis A.

Figure 127:
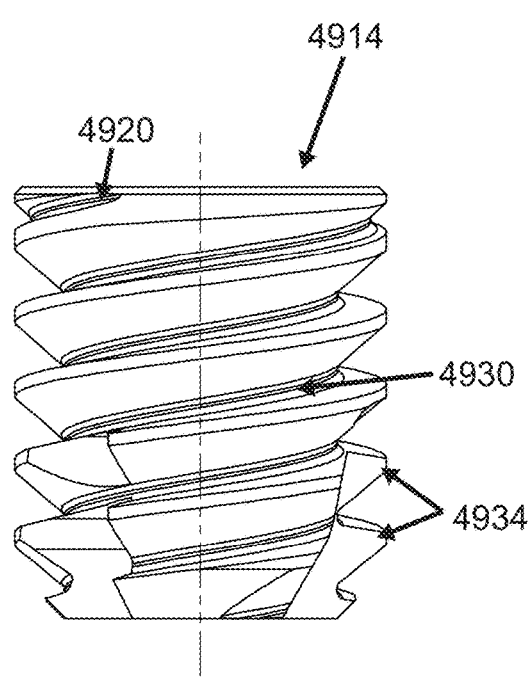
FIG. 127 is a schematic side elevation view of a flangeless anchor housing.
Figure 128:
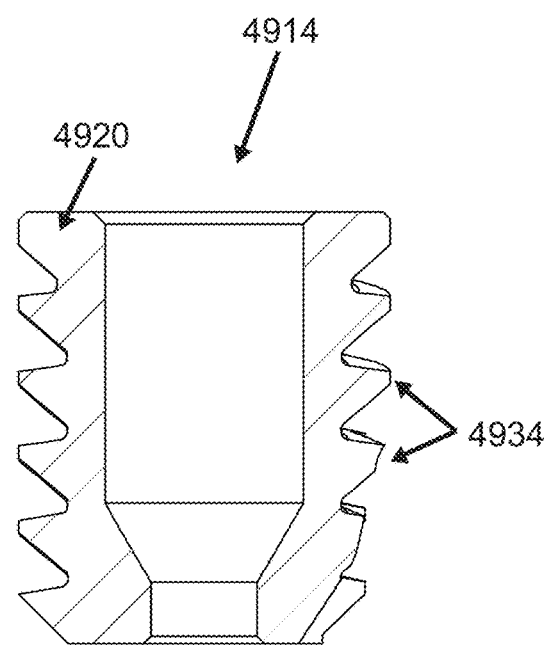
FIG. 128 is a cross-sectional view of the anchor housing of FIG. 127.
Figure 129:
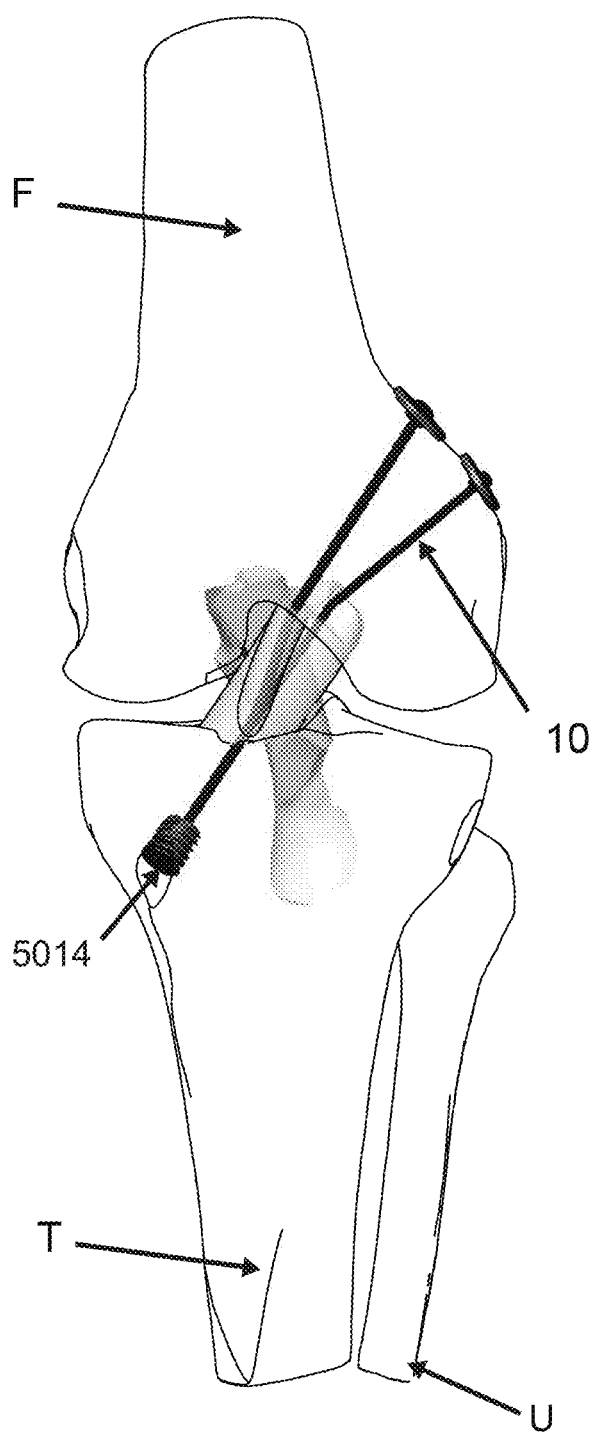
FIG. 129 is a schematic view of the anterior aspect of a human knee joint having a double-bundle ligament augmentation using the anchor housing shown in FIGS. 127 and 128.

Other means may be provided in order to permit the anchor 12 to be implanted in various orientations. For example, FIGS. 127 and 128 illustrate a housing 4914 which lacks a flange as depicted in other embodiments. (The housing 4914 may optionally include an extension portion and breakaway structure as described with respect to other anchor embodiments, not shown in FIG. 127 or 128). An exterior surface 4930 of the body 4920 of the housing 4914 is formed into male threads 4934. Alternatively, exterior surface 4930 may be configured (in terms of structure, material selection, or both) according to one of the other embodiments shown in FIG. 6-8 to improve the connection between the housing 4914 and the bone. Stated another way, a maximum diameter of the housing is defined by an outer extent of the threads 4934. The lack of the flange extending beyond the outer extent of the threads 4934 permits the housing 4914 to be implanted flush or sub-flush relative to the bone surface. More importantly, it permits it to be installed in a bore or passage which is oriented at any arbitrary angle relative to the surface of the bone. In such situations, if a flange were used, a gap would be present between at least some portions of the flange and the bone. Stated another way, the bore or passage in the bone can extend along an axis which is oblique to the surface of the bone. An example is shown in FIG. 129 wherein implant having housing 4914 is implanted into a human tibia T, in a passage which is oblique to the surface of the bone.

The anchor 12 may have an overall size which is generally small enough to be implanted inside a human body. In one example the housing 14 may be cylindrical in shape with an outside diameter "D2" of about 3 to 12 mm, and the flange 32 may have an outside diameter "D3" about 5 to 20 mm.

The exterior surface 30 of the housing 14, specifically the body 20 may be configured (in terms of structure, material selection, or both) to improve the connection between the housing 14 and the bone. Examples of exterior surfaces configured to achieve this function are illustrated in FIGS. 6, 7, and 8.

Figure 6:
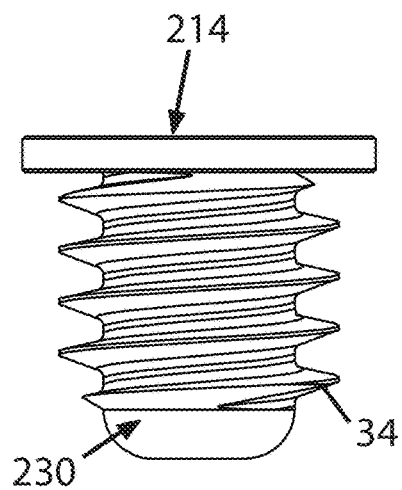
FIG. 6 is a schematic side elevation view of a housing having an exterior surface including male threads.

FIG. 6 shows a housing 214 in which an exterior surface 230 of the body is formed into male threads 34.

Figure 7:
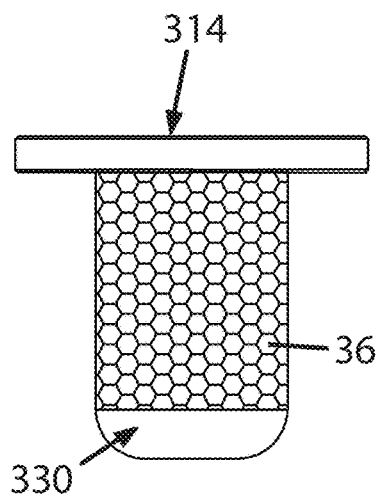
FIG. 7 is a schematic side elevation view of a housing having an exterior surface including a surface coating.

FIG. 7 shows a housing 314 in which an exterior surface 330 of the body has a coating 36 applied thereto which encourages bone growth. One example of a known type of coating that encourages bone growth and infiltration is an inorganic crystalline structure such as hydroxyapatite ("HA").

Figure 8:
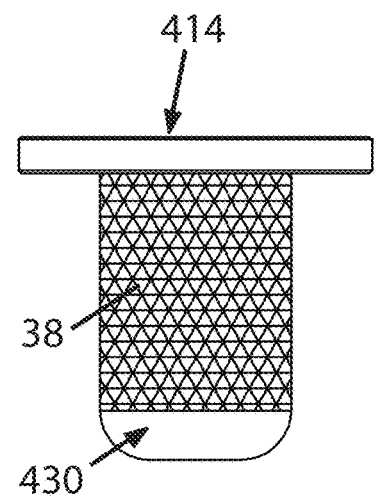
FIG. 8 is a schematic side elevation view of a housing having an exterior surface incorporating knurling.

FIG. 8 shows a housing 414 in which an exterior surface 430 of the body has a surface texture 38 incorporating areas which are relatively raised interspersed with areas that a relatively lowered. One example of a known type of surface texture is knurling.

Figure 94:
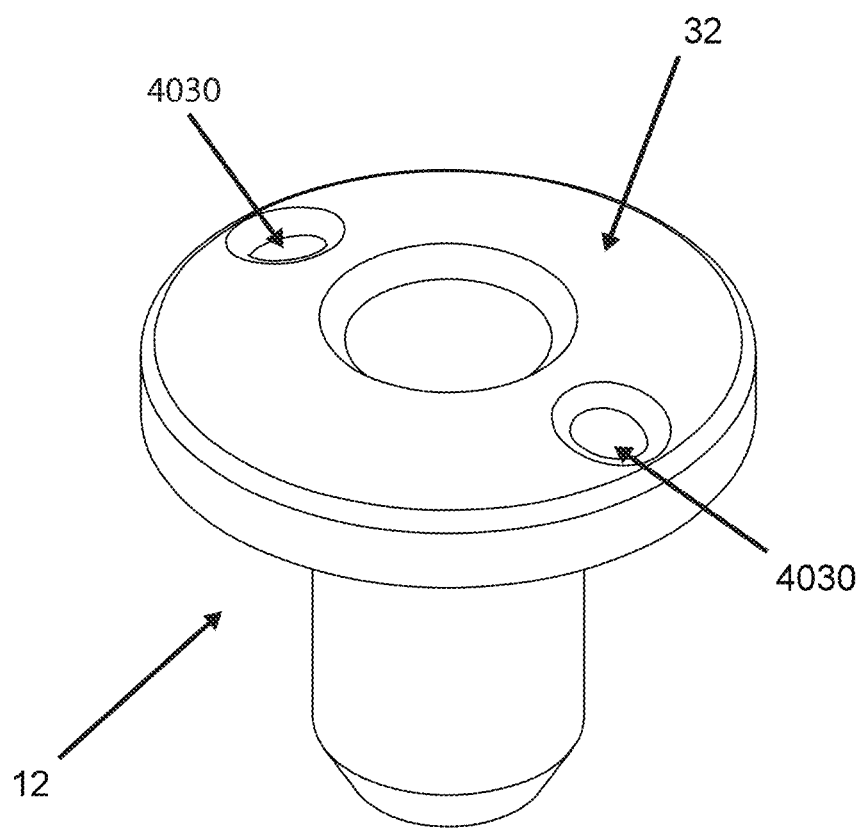
FIG. 94 is a schematic perspective view of an anchor housing including suture holes in the flange thereof.

The housing 12 may be provided with means for securing it to bone. For example, FIG. 94 illustrates a housing 12 with holes 4030 passing through the flange 32. In use, a suture loop (not shown) may be passed around a bone or other part of a patient's body. Distal ends of the suture loop may be passed through the holes 4030 and tied together to secure the housing 12 against the bone surface.

The housing 14 may incorporate a connection feature configured to permit a secure, releasable connection to an instrument used for insertion or manipulation of the anchor 12. Examples of connection features are illustrated in FIGS. 9-17.

FIG. 9 shows a housing 514 incorporating female threads 40 which engage male threads 42 of an insertion instrument (shown generically at "I").

FIG. 10 shows a housing 614 having a flange incorporating male threads 44 which engage female threads 48 of an insertion instrument I.

FIGS. 11 and 12 show a housing 714 having internal slots 50 which receive external lugs 52 formed on the periphery of an insertion instrument I, forming a "bayonet" type connection.

FIGS. 13 and 14 show a housing 814 having circumferential slots 54 formed in the flange 32 which receive cylindrical lugs 55 formed on an end surface of an insertion instrument I.

FIG. 15 shows a housing 914 having a counterbore 56 formed therein sized to receive collet jaws 58 formed on an insertion instrument I.

Figure 16:
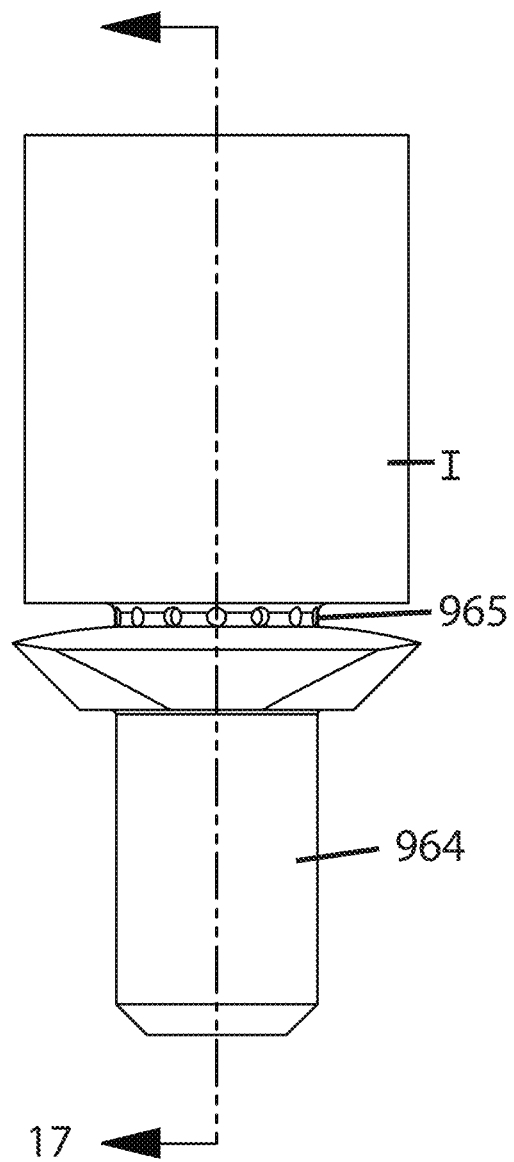
FIGS. 16 and 17 are schematic side elevation and cross-sectional views, respectively of a housing having a breakaway connection to a corresponding instrument.
Figure 17:
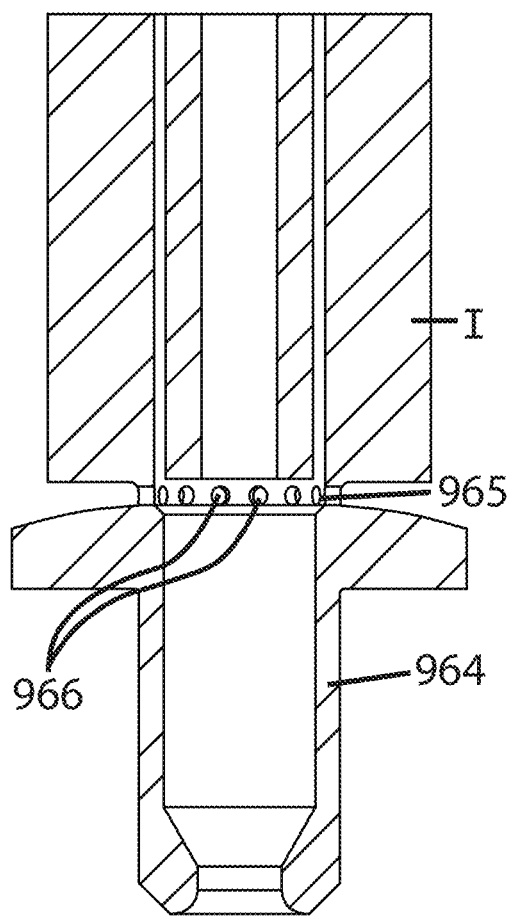

FIGS. 16 and 17 show a housing 964 connected to a distal end of an insertion instrument I by an integral collar 965 which is perforated with openings 966. In use, insertion instrument I may be used to implant the housing 964, and secure the tensile member 10. The collar 965 may then be fractured in order to detach insertion instrument I. This may be described as a "breakaway" or "snap-off" connection.

The housing 14 may incorporate a sleeve retention feature configured to retain the sleeve 18 in an activated position. These features interact with retention features of the sleeve 18 which are described in more detail below. Examples of sleeve retention features are illustrated in FIGS. 18-20.

Figure 18:
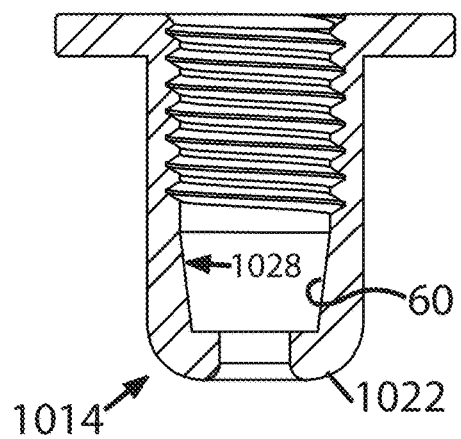
FIG. 18 is a schematic cross-sectional view of a housing having a tapered sleeve retention feature.

FIG. 18 shows a housing 1014 incorporating a tapered section 60 in the interior surface 1028 of the peripheral wall. The tapered section 60 is located near the first end 1022 of the body 1020.

Figure 19:
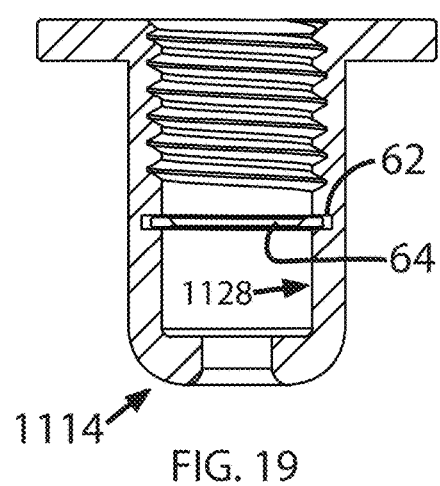
FIG. 19 is a schematic cross-sectional view of a housing having a snap ring sleeve retention feature.

FIG. 19 shows a housing 1114 in which the interior surface 1128 of the peripheral wall 1126 incorporates a circumferential groove 62 which receives a resilient snap ring 64.

Figure 20:
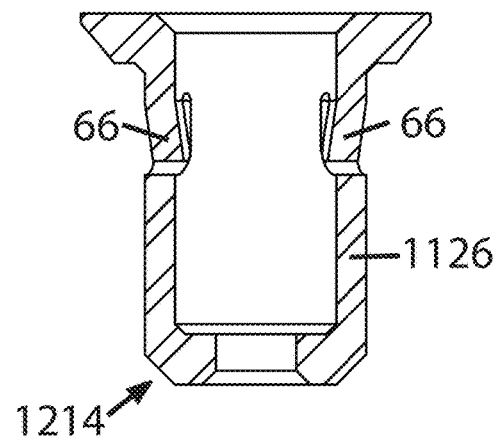
FIG. 20 is a schematic cross-sectional view of a housing having resilient sleeve retention tabs.

FIG. 20 shows a housing 1214 in which the peripheral wall 1226 defines one or more integral resilient locking tabs 66 that extend radially inward.

The housing 14 may be made from any material which is biocompatible and which will engage the other elements so as to transfer tensile force thereto. As used herein, the term "biocompatible" refers to a material which is not harmful to living tissue. Nonlimiting examples of suitable materials for the housing 14 include polymers and metal alloys. Nonlimiting example of suitable metal alloys include stainless steel alloys and titanium alloys. The housing 14 may be fabricated by a technique such as machining, forging, casting, sintering, or additive manufacturing (e.g., "3D printing"). Optionally, the housing 14 may comprise a porous material.

The housing 14 may be treated with known coating such as titanium nitride, chrome plating, carbon thin films, and/or diamond-like carbon coatings.

The housing 14 may allow for the placement of a cap after implantation to protect the pieces inside or to create a smoother surface. Examples are shown in FIGS. 40-43.

FIGS. 40 and 41 illustrate a housing 2114 with a flange 2132. A smooth, convex-curved cap 2133 includes an internal recess 2134 closely matched to the exterior shape of the flange 2132 so that the cap 2133 can engage the flange 2132 in a snap-fit relationship.

FIGS. 42 and 43 illustrate a housing 2214 with a flange 2232 and internal threads 2233. A cap 2234 with a smooth, convex-curved exterior includes a central stud 2235 with external threads 2236 that can engage internal threads 2233 to secure the cap 2234 to the housing 2214.

Referring back to FIGS. 3 and 4, the collet 16 is a hollow member with first and second ends 67, 68 and an exterior surface 70. The collet 16 has a central bore 72 which is sized to receive the tensile member 10 described above. For example, the central bore 72 may be cylindrical, with a diameter "D4" which is initially slightly larger than a diameter D1 of the tensile member 10. The central bore 72 need not have a circular cross-section; the cross-section may be a polygon shape (e.g. triangular, square) or it may be a lobed shape (e.g., triangular with radiused corners) or spline shaped.

The collet 16 is configured so as to readily permit it to be swaged, i.e. shaped in such a manner to reduce its cross-section and the size of the central bore 72 so that it firmly engages the tensile member 10 and allows a tensile force to be applied thereto. The act of swaging may involve the collet 16 being deformed, crushed, collapsed, or compressed. The collet 16 is configured, e.g., sized and shaped, such that when subjected to pressure from the sleeve 18, it will abut the internal flange 31 of the body 20, thus stopping its further axial movement, and permitting the swaging action (described in more detail below) to take place without axial movement of the collet 16 relative to the tensile member 10 or housing 14.

The exterior surface 70 has a shape adapted to interact with the interior surface of the sleeve 18 described below so as to produce a radially inwardly directed force on the collet 16 in response to the axial movement of the sleeve 18. Fundamentally, at least one of the exterior surface 70 of the collet 16 and the interior surface of the sleeve 18 incorporates a taper i.e., a diameter or lateral dimension which is larger near the first end and smaller near the second end of the respective element. As used herein, the term "taper" may include straight tapers as well as other shaped which are effectively tapered such as stepped shapes or shapes incorporating concave or convex curves. In the example shown in FIGS. 3 and 4, the exterior surface 70 is cylindrical with chamfered ends. FIGS. 21-26 generally show alternative collets where the peripheral exterior surface is tapered, defining a shape like a frustum of a cone.

Additionally, the internal flange 31 of the housing 14 and the exterior surface 70 may be configured such that axial movement of the collet 16 towards the first end 22 causes a radially inwardly directed force on the collet 16. For example, FIG. 4 illustrates a transition section 31' adjacent the interface of the internal flange 31 in the cylindrical portion of the interior surface 28. The shaping of this transition section 31' may be tailored to control the direction and magnitude of a radially-inward force applied to the collet 16. In general, the transition section defines a constriction adjacent the internal flange 31. In the illustrated example, the transition section 31' is a straight taper or generally conical section; other shapes such as chamfers, fillets, curves, splines, etc. may be used.

The collet 16 may be made from any material which will engage the tensile member 10 so as to transfer tensile force thereto and which can be successfully swaged. Nonlimiting examples of suitable materials include polymers and metal alloys. One nonlimiting example of a suitable metal alloy is an aluminum alloy. The collet 16 may be fabricated by a technique such as machining, forging, casting, sintering, or additive manufacturing (e.g., "3D printing"). The collet 16 may be made from a material which has a lower effective elastic modulus than the sleeve 18, or stated another way, is "softer" than the sleeve 18. Optionally, the collet 16 may comprise a porous material.

Optionally, the collet 16 may be coated with a low-friction coating such as diamond-like carbon ("DLC").

Optionally, the collet 16 may incorporate a geometry having sections of removed material or "negative space" which is configured to facilitate collapse of the collet 16, so as to optimize stress around the tensile member 10. Examples of collapsing geometries are illustrated in FIGS. 21-26.

FIGS. 21 and 22 show a collet 116 having a longitudinal through slot 74 formed on one side, and a longitudinal groove 76 formed opposite the through slot 74.

FIGS. 23 and 24 show a collet 216 having a plurality of curvilinear openings 77 formed through the wall thereof, providing a negative space that allows the collet 216 to collapse inwards.

FIGS. 25 and 26 show a collet 316 having a plurality of longitudinal through slots 78 formed in the wall thereof, each slot 78 being open to at least one end and extending less than the full length of the collet 316. The through slots 78 are arranged to define a spring-like structure.

Optionally, the collet 16 may incorporate a geometry having sections of removed material or "negative space" which are configured to facilitate collapse of the collet 16, in such a way that portions of the collet protrude inward into the central bore to provide improved engagement with a tensile member 10. Examples of collapsing geometries are illustrated in FIGS. 80-85.

Figure 80:
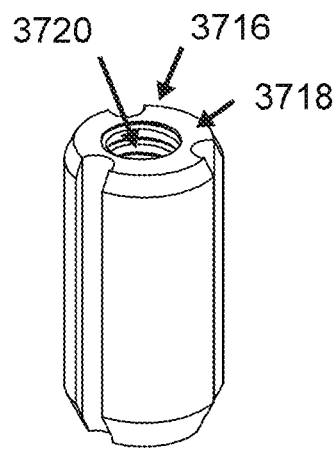
FIGS. 80-82 are schematic side, end, and enlarged partial sectional views, respectively, of a collet having a collapsible construction.
Figure 81:
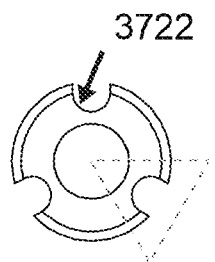
Figure 82:
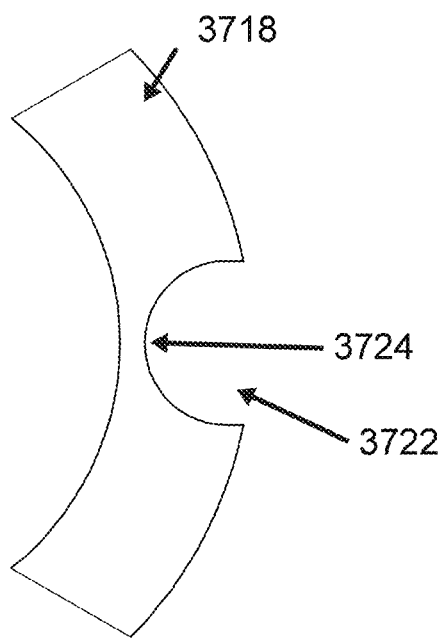

FIGS. 80-82 show a collet 3716 having a sidewall 3718 defining a central bore 3720. It may be made from sintered powdered metal alloy or another material with similar swaging characteristics. The central bore 3720 may include a surface texture 3721 such as the illustrated threads which serve to enhance grip on a tensile member 10 (not shown in FIG. 82). An array of longitudinal grooves 3722 having a U-shape are formed in the outer surface of the sidewall 3718. Each of the grooves 3722 defines a thin neck or web 3724 (see FIG. 82).

Figure 83:
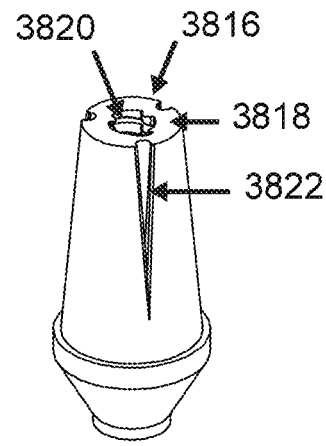
FIGS. 83-85 are schematic side, end, and enlarged partial sectional views, respectively, of the collet of FIG. 82, in a collapsed condition.
Figure 84:
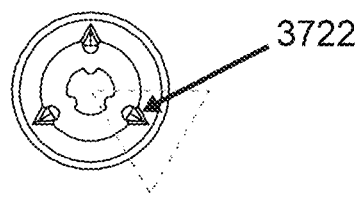
Figure 85:
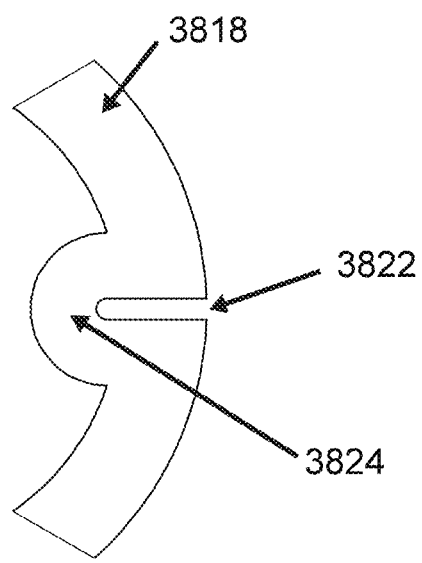

The example shown in FIGS. 80-82 is generally cylindrical prior to swaging. FIGS. 83-85 show the collet 3716 after swaging. Post-swaging, the grooves 3722 may be tapered, having a maximum width at a distal end of the collet 3716, and tapering away to a negligible dimension near a middle portion of the collet 3716. When swaged as described herein, the sidewall 3718 tends to collapse in a manner such that each of the necks 3724 folds into a U-shape and protrudes into the central bore 3720 (see FIG. 85), forming a protrusion 3726 which may have a shape similar to a Roman arch.

Referring back to FIGS. 3 and 4, the sleeve 18 is a hollow member with open first and second ends 80, 82 The sleeve 18 is sized is such that the tensile member 10 described above can pass through the first and second ends 80, 82. The sleeve 18 is defined by a peripheral wall 84 having interior and exterior surfaces 86, 88, respectively. In the illustrated example, the sleeve 18 is generally cylindrical in shape.

The interior surface 86 has a shape adapted to interact with the exterior surface 70 of the collet 16 described above so as to produce a radially inwardly directed force on the collet 16 in response to the axial movement of the sleeve 18. As noted above, at least one of the exterior surface 70 of the collet 16 and the interior surface 86 of the sleeve 18 incorporates a taper i.e., a diameter or lateral dimension which is larger near the first end and smaller near the second end of the respective element. In the example shown in FIGS. 3 and 4, the interior surface 86 is tapered, defining a shape like a frustum of a cone, with a larger diameter at the first end 80.

The interior surface 86 of the sleeve 18 may have various geometries selected to optimize the swaging force. The interior surface 86 of the sleeve 18 shown in FIG. 4 has a one-way taper. Examples of alternative compression surface geometries are illustrated in FIGS. 27-29.

Figure 27:
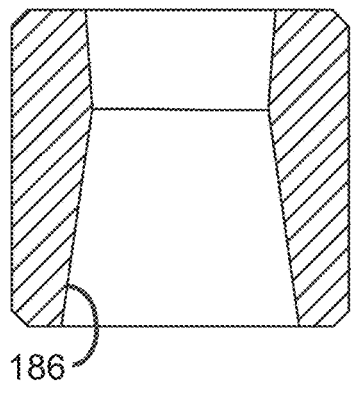
FIG. 27 is a schematic cross-sectional view of a sleeve having a double taper interior surface.

FIG. 27 shows an interior surface 186 with a two-way taper.

Figure 28:
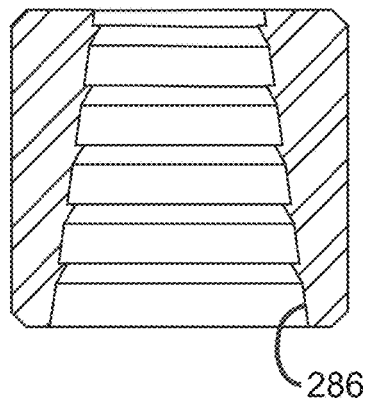
FIG. 28 is a schematic cross-sectional view of a sleeve having a scaled interior surface.

FIG. 28 shows an interior surface 286 having a series of step-like faces defining a "scaled" geometry.

Figure 29:
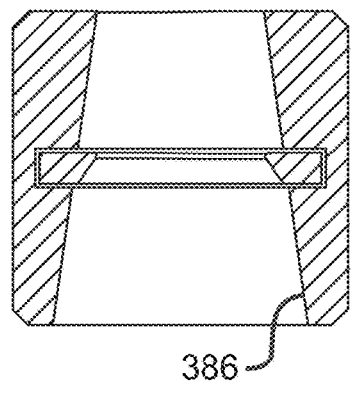
FIG. 29 is a schematic cross-sectional view of a sleeve having an integral snap ring interior surface.

FIG. 29 shows an internal surface 386 with an integral snap ring geometry.

The sleeve 18 may incorporate a retention feature which cooperates with the sleeve retention feature of the housing described above in order to retain the sleeve 18 in an activated position. FIG. 4 illustrates an exemplary retention feature in the form of an annular step 90 formed in the exterior surface 88 of the sleeve 18.

The sleeve 18 may be made from any material which is biocompatible and which can receive axial force and transfer radial compressive force to the collet 16. Nonlimiting examples of suitable materials include polymers and metal alloys. One nonlimiting example of a suitable metal alloy is a stainless steel alloy. The sleeve 18 may be fabricated by a technique such as machining, forging, casting, sintering, or additive manufacturing (e.g., "3D printing"). Optionally, the sleeve 18 may comprise a porous material.

All or a portion of the sleeve 18 may be provided with a known coating such as titanium nitride, chrome plating, carbon thin films, and/or diamond-like carbon coatings.

Figure 30:
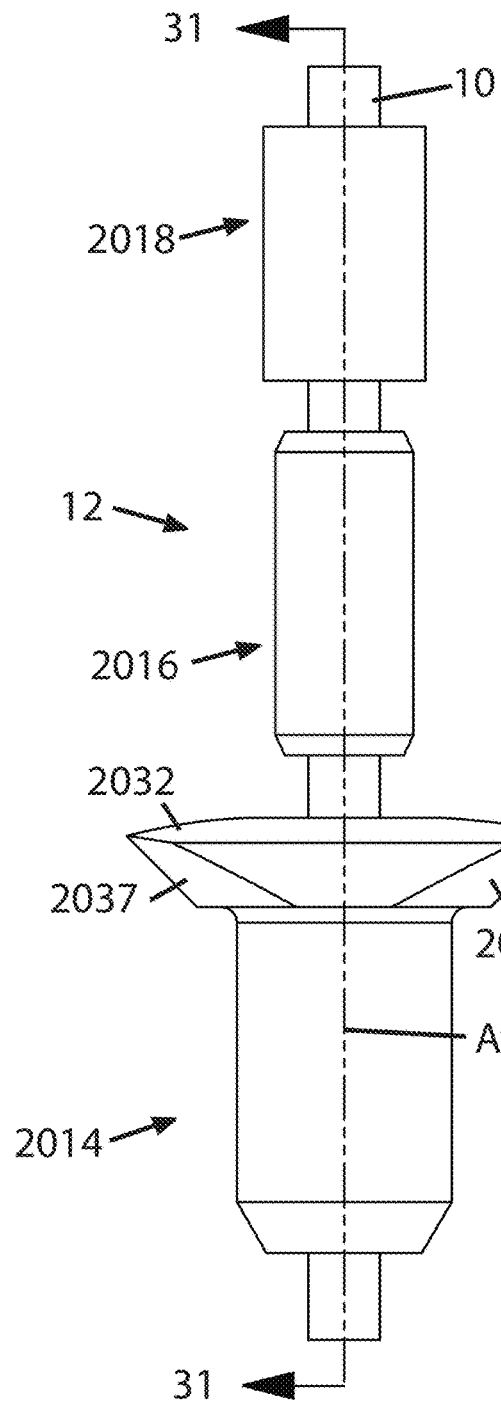
FIG. 30 is an exploded view of another exemplary embodiment of an anchor.
Figure 31:
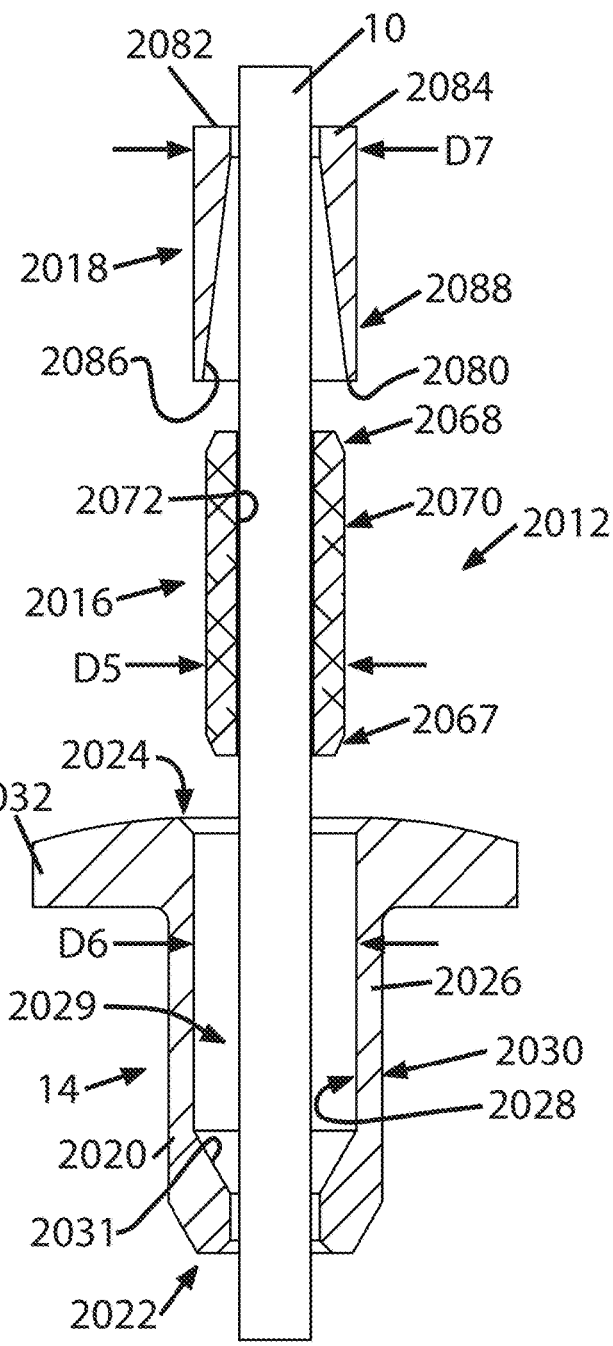
FIG. 31 is a cross-sectional view of FIG. 30.

FIGS. 30-37 illustrate another exemplary embodiment of an anchor, denoted 2012 generally. The anchor 2012 is generally similar in construction to the anchor 12 described above. Any elements of the anchor 2012 not specifically described may be taken to be identical to those of the anchor 12. Referring to FIGS. 30 and 31, the anchor 2012 includes a housing 2014, a collet 2016 received in the housing 2014, and a sleeve 2018 received in the housing 2014 which is capable of moving axially within the housing 2014 so as to swage the collet 2016, thus retaining the tensile member 10.

The housing 2014 has a body 2020 extending along a central axis "A" between first and second ends 2022, 2024. The body 2020 is defined by a peripheral wall 2026 having interior and exterior surfaces 2028, 2030 respectively, and defining a hollow interior 2029. In the illustrated example, the body 2020 is generally cylindrical in shape. The first end of the body 2022 has an internal flange 2031 which is sized to define a stop against axial motion of the collet 2016.

A generally annular flange 2032 is located at or near the second end 2024 and extends radially outwards from the body 2020. In the example illustrated in FIGS. 30 and 31, the flange 2032 incorporates chamfered surfaces 2037 which are configured to engage jaws of an insertion instrument is described in more detail below.

The exterior surface 2030 of the housing 2014 may be configured to improve the connection between the housing 2014 and the bone. Examples of exterior surfaces configured to achieve this function are described above and illustrated in FIGS. 6, 7, and 8.

The housing 2014 may incorporate a connection feature configured to permit a secure, releasable connection to an instrument used for insertion or manipulation of the anchor 2012. Examples of connection features are described above and illustrated in FIGS. 9-17.

The housing 2014 may incorporate a sleeve retention feature configured to retain the sleeve 2018 in an activated position. These features interact with retention features of the sleeve 2018 which are described in more detail below. In the illustrated example, the retention feature is a dimension (e.g., diameter) "D6" of the interior surface 2028 which is selected to provide a predetermined fit with the sleeve 2018, as described in more detail below.

The collet 2016 is a hollow member with first and second ends 2067, 2068 and an exterior surface 2070. The collet 2016 has a central bore 2072 which is sized to receive the tensile member 10 described above. For example, the central bore 72 may be cylindrical, with a diameter "D5" which is initially slightly larger than a diameter D1 of the tensile member 10. The central bore 2072 need not have a circular cross-section; the cross-section may be a polygon shape (e.g. triangular, square) or it may be a lobed shape (e.g., triangular with radiused corners).

The collet 2016 is configured so as to readily permit it to be swaged, i.e. shaped in such a manner to reduce its cross-section and the size of the central bore 2072 so that it firmly engages the tensile member 10 and allows a tensile force to be applied thereto. The act of swaging may involve the collet 2016 being deformed, crushed, collapsed, or compressed. The collet 2016 is configured, e.g., sized and shaped, such that when subjected to pressure from the sleeve 2018, it will abut the internal flange 2031 of the body 2020, thus stopping its further axial movement, and permitting the swaging action to take place without axial movement of the collet 2016 relative to the tensile member 10 or housing 2014.

The exterior surface 2070 has a shape adapted to interact with the interior surface of the sleeve 2018 described below so as to produce a radially inwardly directed force on the collet 2016 in response to the axial movement of the sleeve 2018. Fundamentally, at least one of the exterior surface 2070 of the collet 2016 and the interior surface of the sleeve 2018 incorporates a taper i.e., a diameter or lateral dimension which is larger near one end and smaller near the opposite end of the respective element. In the example shown in FIGS. 30 and 31, the exterior surface 2070 is cylindrical with chamfered ends. The exterior dimensions and shape of the exterior surface 2070 are selected so as to provide a predetermined fit with the sleeve 2018 both before and after a compression process, as described in more detail below.

Additionally, the internal flange 2031 of the housing 2014 and the exterior surface 2070 may be configured such that axial movement of the collet 2016 towards the first end 2022 causes a radially inwardly directed force on the collet 16. Examples of this configuration are described above.

The sleeve 2018 is a hollow member with open first and second ends 2080, 2082. The sleeve 2018 is sized is such that the tensile member 10 described above can pass through the first and second ends 2080, 2082. The sleeve 2018 is defined by a peripheral wall 2084 having interior and exterior surfaces 2086, 2088, respectively. In the illustrated example, the exterior surface 2088 of the sleeve 2018 is generally cylindrical in shape.

The interior surface 2086 has a shape adapted to interact with the exterior surface 2070 of the collet 2016 described above so as to produce a radially inwardly directed force on the collet 2016 in response to the axial movement of the sleeve 2018. As noted above, at least one of the exterior surface 2070 of the collet 2016 and the interior surface 2086 of the sleeve 2018 incorporates a taper i.e., a diameter or lateral dimension which is larger near one end and smaller near the opposite end of the respective element. In the example shown in FIGS. 30 and 31, the interior surface 2086 is tapered, defining a shape like a frustum of a cone, with a larger diameter at the first end 2080.

The interior surface 2086 of the sleeve 2018 may have any of the various geometries described above which are selected to optimize the swaging force.

The sleeve 18 may incorporate a retention feature which cooperates with the sleeve retention feature of the housing described above in order to retain the sleeve 18 in an activated position. In the illustrated example, the retention feature is a dimension (e.g., diameter) "D7" of the exterior surface 2088 which is selected to provide a predetermined fit with the sleeve 2018 both before and after a compression process, as described in more detail below.

Figure 34:
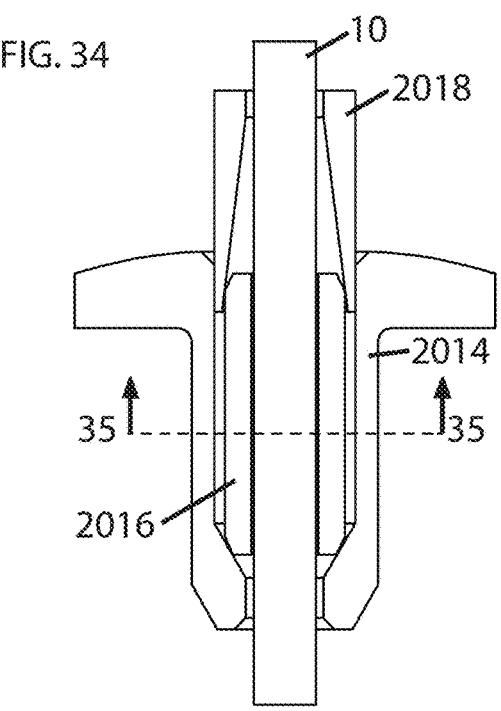
FIG. 34 is a cross-sectional view of the anchor FIG. 30 in an assembled condition, before compression.
Figure 35:
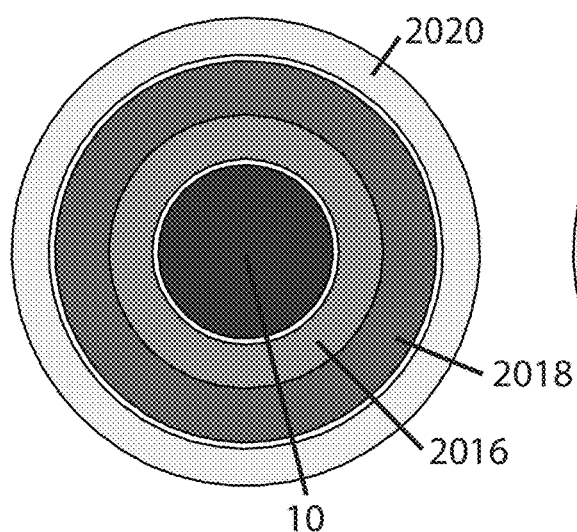
FIG. 35 is a sectional view taken along lines 35-35 of FIG. 34.

FIGS. 34-37 illustrate the engineered interference lock feature of the anchor 2012. Referring to FIGS. 34 and 35, in the assembled, but uncompressed condition, there is a small clearance between the inside diameter D6 of the housing 2014 and the outside diameter D7 of the sleeve 2018. There is also a small clearance between the inside diameter D5 of the collet 2016 and the outside diameter D1 of the tensile member 10.

Figure 36:
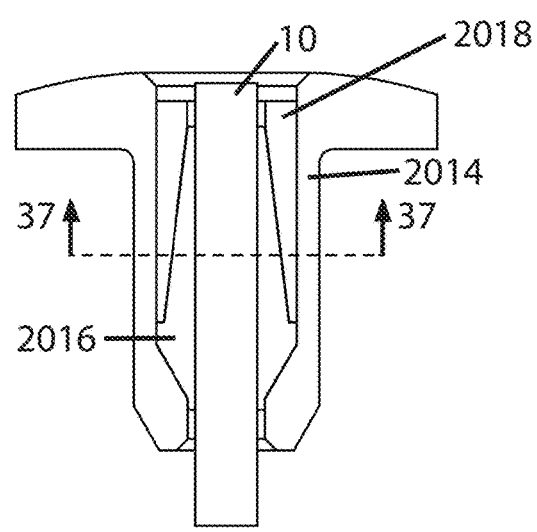
FIG. 36 is a cross-sectional view of the anchor FIG. 30 in a compressed condition.
Figure 37:
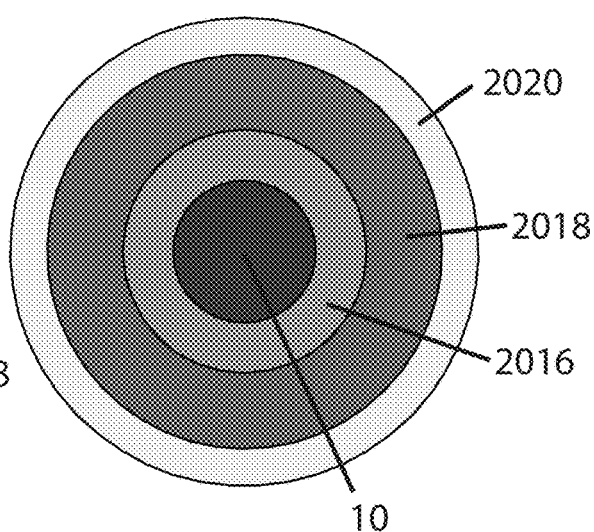
FIG. 37 is a sectional view taken along lines 37-37 of FIG. 36.

FIGS. 36 and 37 illustrate the anchor 2012 in the compressed or actuated condition (e.g. after being compressed by one of the insertion instruments described herein). There is a predetermined interference fit between the inside diameter D6 of the housing 2014 and the outside diameter D7 of the sleeve 2018. This occurs because the sleeve 2018 is forced radially outwards as it is pushed axially over the collet 2016. Furthermore, there is a predetermined interference fit between the inside diameter D5 of the collet 2016 and the outside diameter D1 of the tensile member 10. In this compressed condition, the tensile member 10 is significantly compressed radially and held by the housing-sleeve-collet concentrically compressed configuration.

The materials and/or coatings used in the construction of the housing 2014, collet 2016, and sleeve 2018 may be as described for the housing 14, collet 16, and sleeve 18 described above.

FIGS. 72-76 illustrate another exemplary embodiment of an anchor, denoted 3012 generally, which incorporates a "breakaway" or "snap-off" connection. The anchor 3012 is generally similar in construction to the anchor 2012 described above. Any elements and/or features of the anchor 3012 not specifically described may be taken to be identical to those of the anchor 2012. Referring to FIGS. 72-73, the anchor 3012 includes a housing 3014, a collet 3016 received in the housing 3014, and a sleeve 3018 received in the housing 3014 which is capable of moving axially within the housing 3014 so as to swage the collet 3016, thus retaining a tensile member 10 (not shown in FIGS. 72, 73).

The housing 3014 has a body portion 3020 extending along a central axis "A" between first and second ends 3022, 3024. The portion 3020 is defined by a peripheral wall 3026 having opposed interior and exterior surfaces, and defining a hollow interior. In the illustrated example, the body portion 3020 is generally cylindrical in shape. The first end of the body portion 3020 has an internal flange 3031 which is sized to define a stop against axial motion of the collet 3016.

A generally annular flange 3032 is located at or near the second end 2024 and extends radially outwards from the body 3020.

The housing 3014 includes an extension portion 3021 extending away from the second end 3024 of the body portion 3020. The extension portion 3021 is coupled to the body portion 3020 by a breakaway structure 3023. As manufactured and prior to use, the entire housing 3014 forms a single unitary, integral, or monolithic structure including the body portion 3020, extension portion 3021, and breakaway structure 3023.

The extension portion 3021 extends between a first end 3025 and a second 3027. The second end 3027 is interconnected to the breakaway structure 3023. The first end 3025 may be provided with a mechanical connector for being connected to an insertion instrument which is described in more detail below. In the illustrated example (FIG. 74) the first end 3025 is provided with a connector 3029 in the form of screw threads. Other mechanical connecting devices such as bayonet connectors, barbs, interrupted threads, ball detents, or lugs and grooves may be used instead of threads. As used herein, the term "mechanical connector" thus refers to a connection that may be readily separated without the use of tools.

The breakaway structure 3023 is configured in terms of its shape, dimensions, and material properties such that it will retain its structural integrity and interconnected to the body portion 3020 and the extension portion 3021 when subjected to tensile loads up to a first magnitude sufficient to complete a swaging process of the anchor 3012 as described elsewhere herein. This is referred to herein as a "first predetermined tensile load". The breakaway structure 3023 is further configured in terms of its shape, dimensions, and material properties such that it will fail and permit separation of the body portion 3020 and the extension portion 3021 when subjected to tensile loads equal to or greater than a second magnitude, referred to herein as a "second predetermined tensile load". The second tensile load is greater than the first tensile load. The second tensile load may be selected to be sufficiently greater than the first predetermined tensile load such that failure of the breakaway structure 3023 is unlikely to occur during the swaging process. Stated another way, the second predetermined tensile load may have a safety margin over the first predetermined tensile load. In one example, the second predetermined tensile load may be selected to be at least 50% to 100% greater than the first predetermined tensile load.

In general, the breakaway structure 3023 may include one or more stress-concentrating columns which present a known cross-sectional area, thus permitting reliable computation of the tensile stresses in the breakaway structure 3023 for a given applied load.

Figure 75:
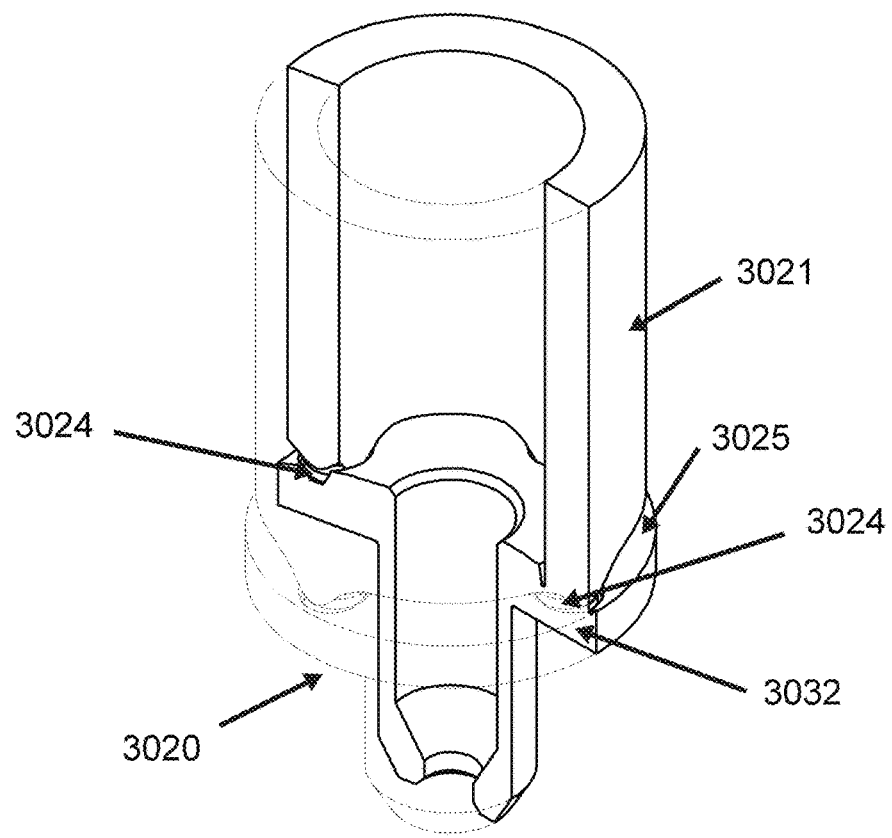
FIG. 75 is a sectioned perspective view of a portion of the anchor of FIG. 72, showing a breakaway structure thereof.
Figure 76:
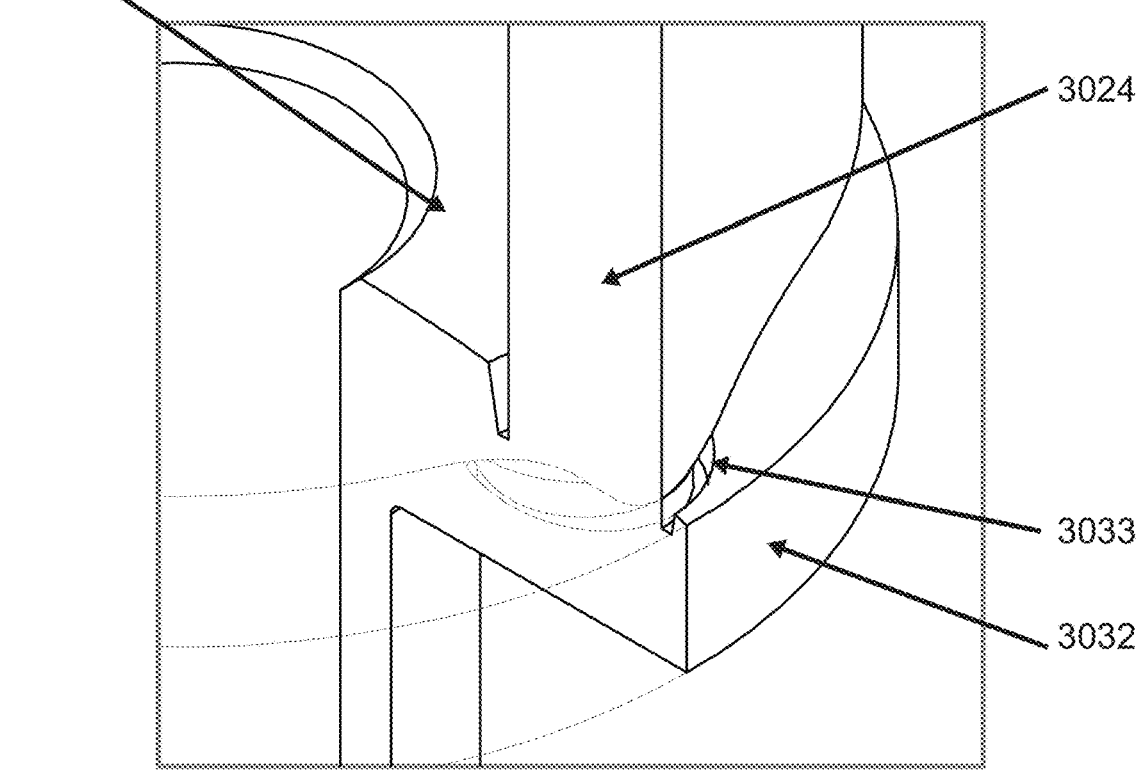
FIG. 76 is an enlarged view of a portion of FIG. 75.

In the illustrated example, best seen in FIGS. 75 and 76, the breakaway structure 3023 includes a plurality of stress-concentrating columns 3024 arrayed around the periphery of the flange 3032, which have a circular cross-sectional shape adjacent to and/or or at the flange 3032. The stress-concentrating columns 3024 are separated by openings 3069. It will be understood that other column cross-sectional shapes providing a predictable cross-sectional area may be used, and that the cross-sectional shape may vary over the length of the column.

Optionally, the stress-concentrating columns 3024 may intersect the flange 3032 at the bottom of recesses 3033 formed in the flange 3032. In use, this permits the stress-concentrating columns 3024 to separate along a fracture plane which is "below" a top surface 3035, or stated another way it is sub-flush to, or recessed from, the top surface 3035.

The exterior surface of the housing 2014 may be configured to improve the connection between the housing 2014 and the bone. Examples of exterior surfaces configured to achieve this function are described above and illustrated in FIGS. 6, 7, and 8.

The housing 3014 and sleeve 3018 may incorporate mutual retention features configured to retain the sleeve 3018 in an activated position, as described above with respect to anchor 2012.

The collet 3016 is a hollow member having a central bore 2072 which is sized to receive the tensile member 10 described above. In one example, the collet 3016 may incorporate substantially the same features as collet 2016 described above.

The sleeve 3018 is a hollow member. In one example, the sleeve 3018 may incorporate substantially the same features as sleeve 2018 described above.

All or a portion of the anchors described above may be made as part of an integral, unitary, or monolithic whole. This may be accomplished, example, by using additive manufacturing process.

Figure 38:
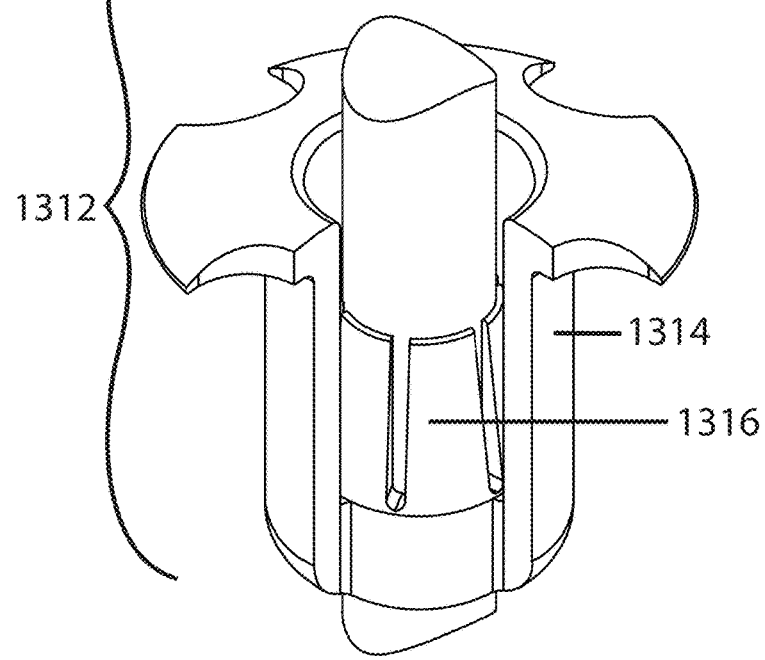
FIG. 38 is a schematic, partially-sectioned perspective view of an exemplary anchor having an integral collet.

FIG. 38 illustrates an exemplary anchor 1312 comprising a housing 1314, a collet 1316, and a sleeve 1318 corresponding to those components as described above. In this example, the collet 1316 is integral, unitary, or monolithic with the anchor 1312. The sleeve 1318 is a separate component.

Figure 39:
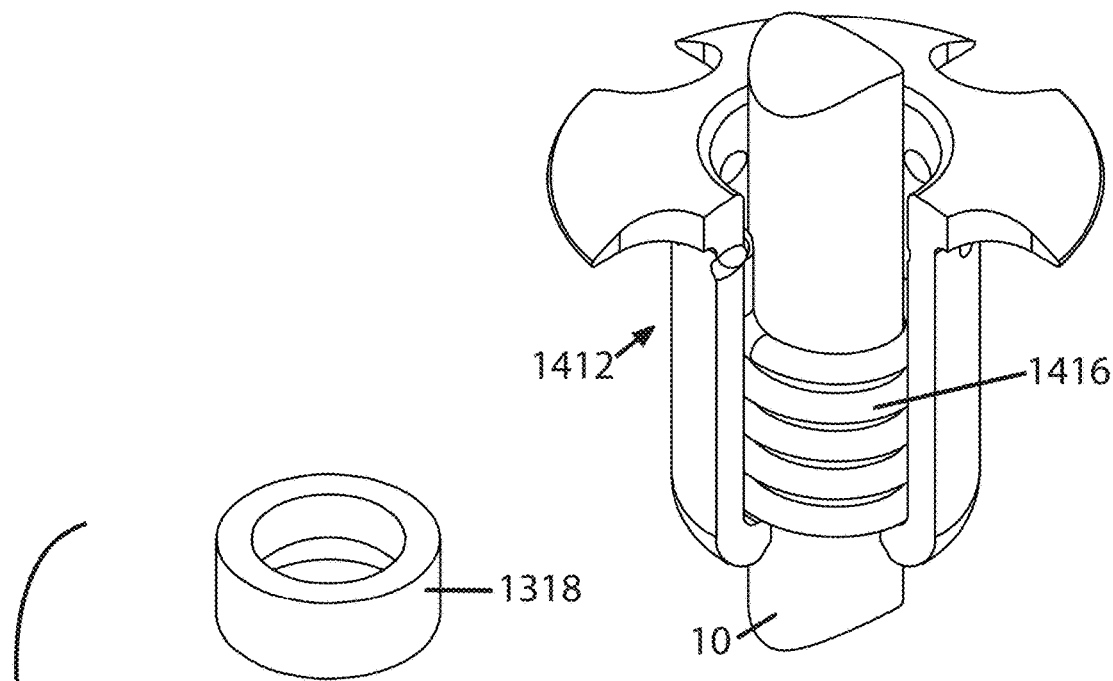
FIG. 39 is a schematic, partially-sectioned perspective view of an exemplary anchor having an integral collet and sleeve.

FIG. 39 illustrates an exemplary anchor 1412 comprising a housing 1414 which receives an internal member 1416. The internal member 1416 is integral, unitary, or monolithic with the anchor 1412. This internal member 1416 is shaped like a tapered coil spring. The bottom end of the coil spring 1416 is held stationary while the top of the coil spring 1416 is allowed to rotate by means of a rotary actuator tool (not shown) that holds the housing 1412 stationary. This tool could be similar to a spanner-type device with pins or lugs and holds the housing 1412 stationary by interfacing with the four locking recesses cut into the flange as shown. When the top of the internal member 1416 is rotated (in this case clockwise), the inner diameter is gradually reduced and constricts around the tensile member 10 to hold it in place axially.

Figure 68:
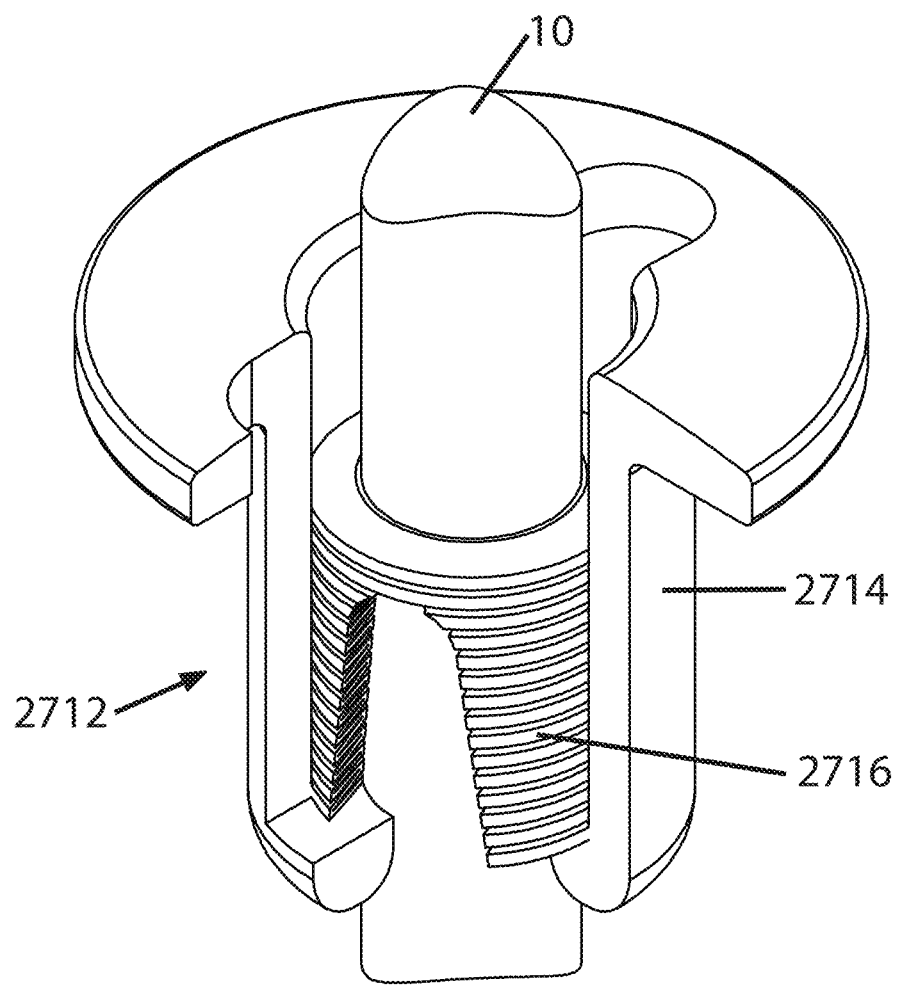
FIG. 68 is a schematic, partially-sectioned perspective view of an exemplary anchor having an integral internal member.

FIG. 68 illustrates an exemplary anchor 2712 comprising a housing 2714 which receives an internal member 2716. This internal member 2716 is shaped like an accordion or wave spring. When compressed axially, the folds deform, bind together, and swage down on the tensile member 10 radially inward. Internal member 2716 thus functions as both a collet and a sleeve. The internal member 2716 optionally may be integral, unitary, or monolithic with the anchor 2712.

Figure 44:
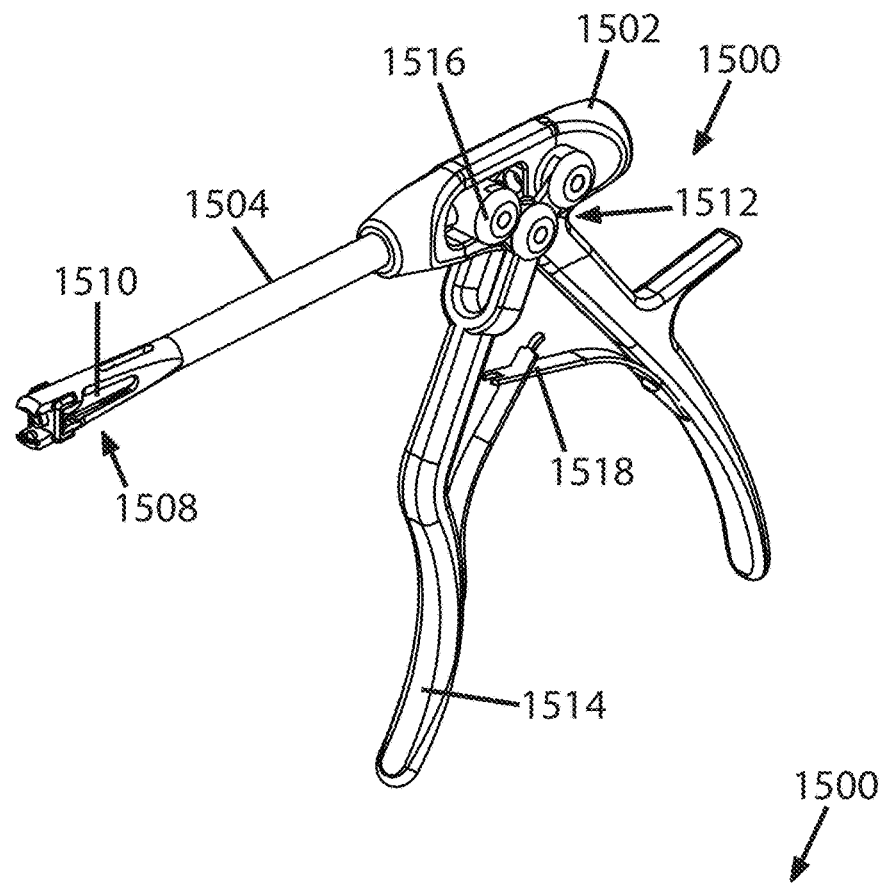
FIG. 44 is a schematic perspective view of an installation instrument for use with the anchor described herein.
Figure 45:
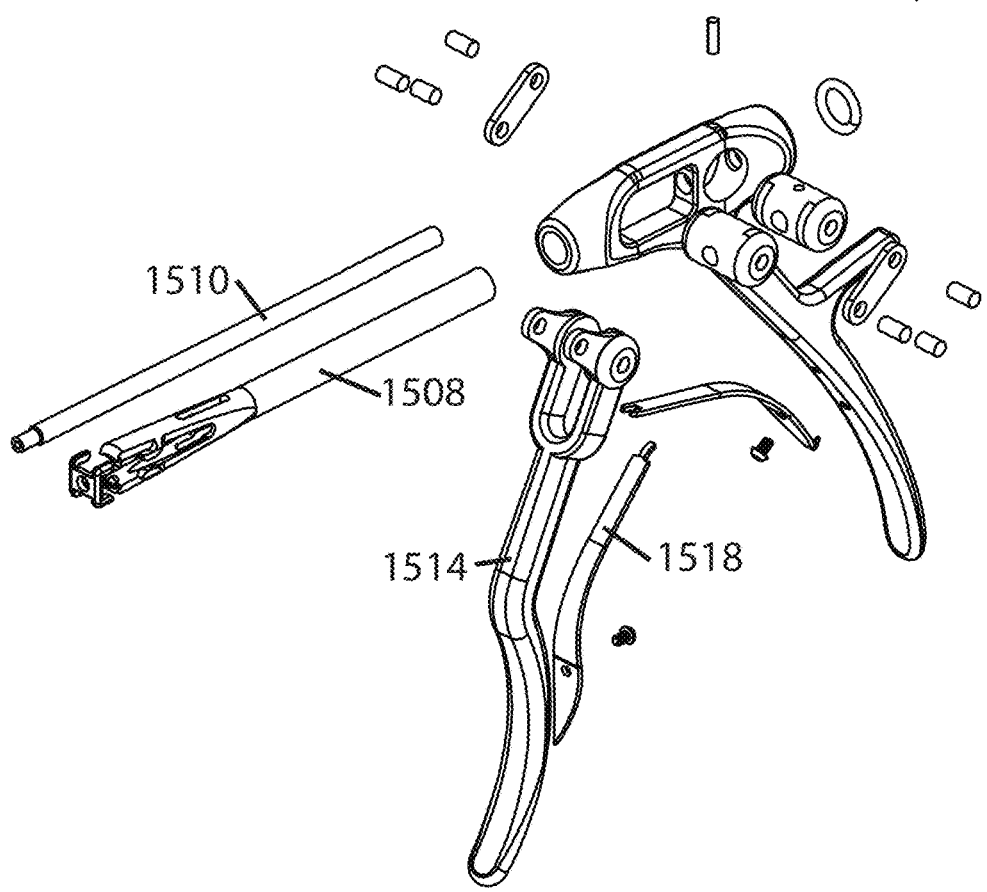
FIG. 45 is an exploded view of the installation instrument of FIG. 44.

FIGS. 44 and 45 an exemplary insertion instrument 1500 which may be used to insert, tension, and activate the anchors 12 described above. The basic components of the insertion instrument 1500 are a body 1502 having a handle, a stem 1504 extending from the body 1502 and having an anchor connection mechanism 1508 disposed at a distal end thereof, a hollow pushrod 1510 extending through the stem 1504 and slidably movable between retracted and extended positions, and a driving mechanism 1512 for moving the pushrod 1510 between retracted and extended positions. The stem 1504 and the pushrod 1510 may be rigid or flexible.

In the illustrated example, the driving mechanism 1512 comprises a toggle linkage 1516 which is manually operated by an operating handle 1514. More specifically, the toggle linkage 1516 is arranged such that when the operating handle 1514 is released, return springs 1518 drive the operating handle 1514, toggle linkage 1518, and pushrod 1510 towards the retracted position, and when the operating handle 1514 is squeezed, it moves the toggle linkage 1516 which in turn extends the pushrod 1510 towards the extended position. The toggle linkage 1516 may be arranged to have a fixed or adjustable range of motion.

It will be understood that the driving mechanism 1512 could be replaced with a different type of mechanical linkage or with the powered devices such as an electrical, pneumatic, or hydraulic actuator (not shown).

Figure 46:
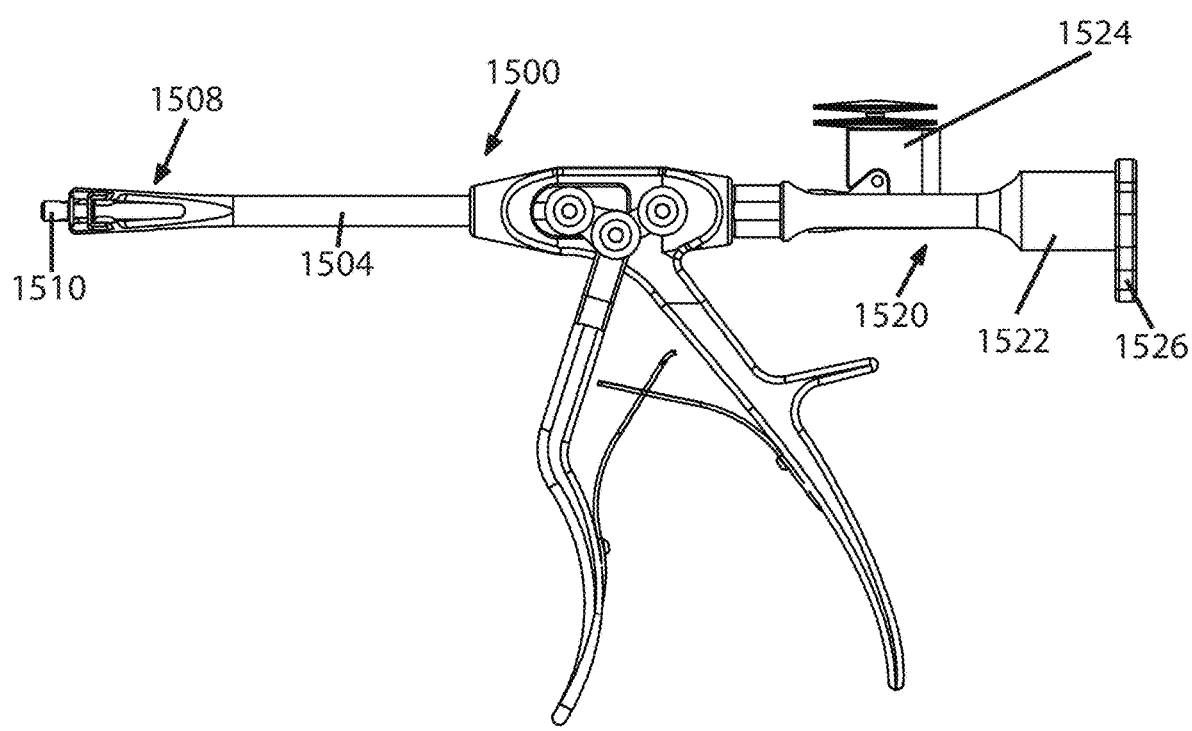
FIG. 46 is a schematic side elevation view of the installation instrument of FIG. 44, with a tensioner attached thereto.

FIG. 46 illustrates an exemplary tensioner 1520 having a housing 1522 which may be connected to the insertion instrument 1500. The tensioner 1522 includes a yoke 1524 configured to clamp a tensile member 10 passing through the pushrod 1510. The yoke 1524 is movable relative to the housing 1522, for example using an internal mechanical driving mechanism (not shown) actuated by an operating knob 1526. Means may be provided for measuring the tension applied to the tensile member 10. For example, the yoke 1524 may be connected to the housing 1522 through a calibrated spring such that the deflection of the yoke 1524 is proportional to applied tension. Alternatively, a calibrated force gauge or other similar mechanism (not shown) may be provided.

The tensioner 1520 of FIG. 46 is effective to set the tension on a single tensile member 10. In various applications, which will be described in more detail below, it is desirable to pass multiple tensile members 10 through a single anchor, and to set the tension of each of the tensile members 10 independently.

Figure 86:
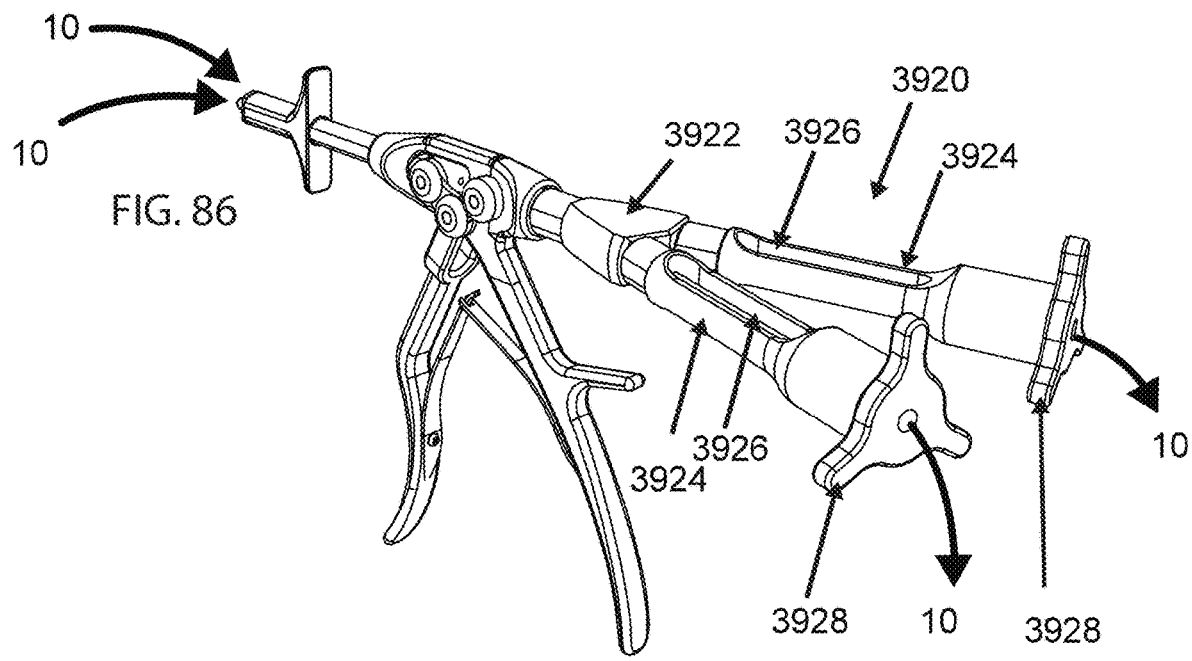
FIG. 86 is a schematic perspective view of an installation instrument, with a first embodiment of a multiple-strand tensioner attached thereto.

FIG. 86 illustrates an exemplary multi-strand tensioner 3920 having a housing 3922 which may be connected to the any of the insertion instruments described herein. The housing 3922 includes first and second sub-housings 3924 Which are arranged in a diverging Y-shape. Each sub-housing 3924 includes a yoke 3926 configured to clamp a tensile member 10 passing through the pushrod of the insertion instrument. Each yoke 3926 is movable relative to its respective sub-housing 3924, for example using an internal mechanical driving mechanism (not shown) actuated by an operating knob 3928. Means may be provided for measuring the tension applied to the tensile member 10. For example, the yoke 3926 may be connected to the respective sub-housing 3924 through a calibrated spring such that the deflection of the yoke 3926 is proportional to applied tension. Alternatively, a calibrated force gauge or other similar mechanism (not shown) may be provided.

Figure 87:
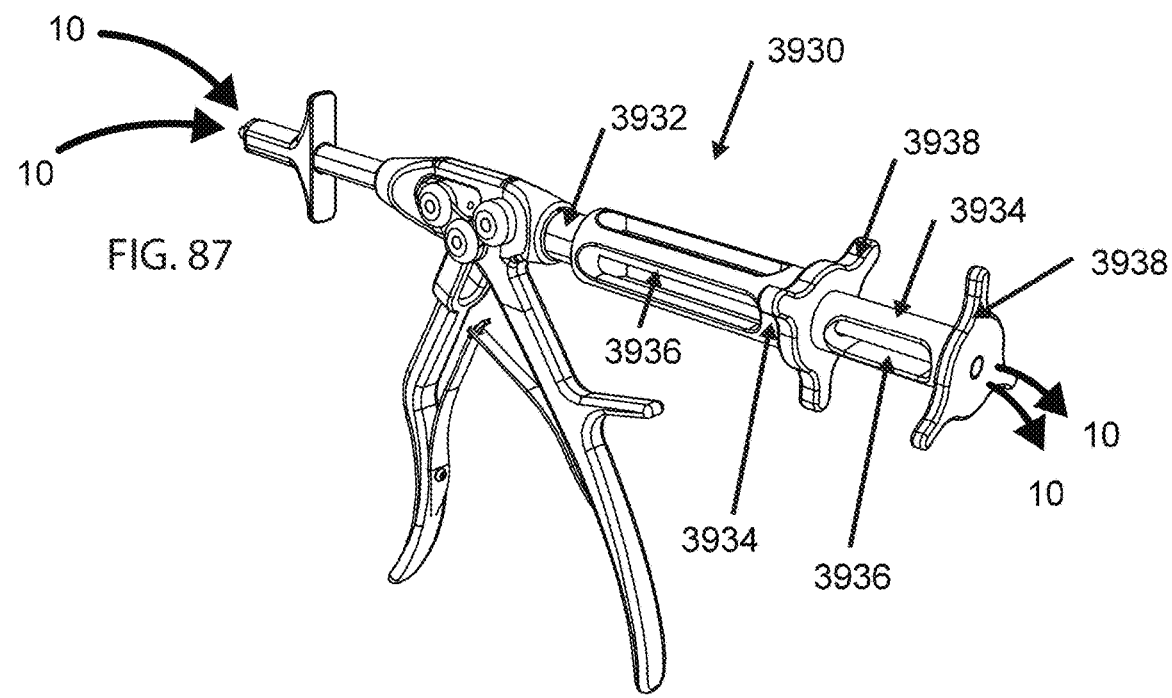
FIG. 87 is a schematic perspective view of an installation instrument, with a second embodiment of a multiple-strand tensioner attached thereto.

FIG. 87 illustrates another example of a multi-strand tensioner 3930 including a housing 3932 including first and second sub-housings 3934 arranged in a coaxial configuration. Each sub-housing 3934 includes a yoke 3936 configured to clamp a tensile member 10 passing through the pushrod of the insertion instrument. Each yoke 3936 is movable relative to its respective sub-housing 3934, for example using an internal mechanical driving mechanism (not shown) actuated by an operating knob 3938. Means may be provided for measuring the tension applied to the tensile member 10. For example, the yoke 3936 may be connected to the respective sub-housing 3934 through a calibrated spring such that the deflection of the yoke 3936 is proportional to applied tension. Alternatively, a calibrated force gauge or other similar mechanism (not shown) may be provided.

Figures 47, 48:
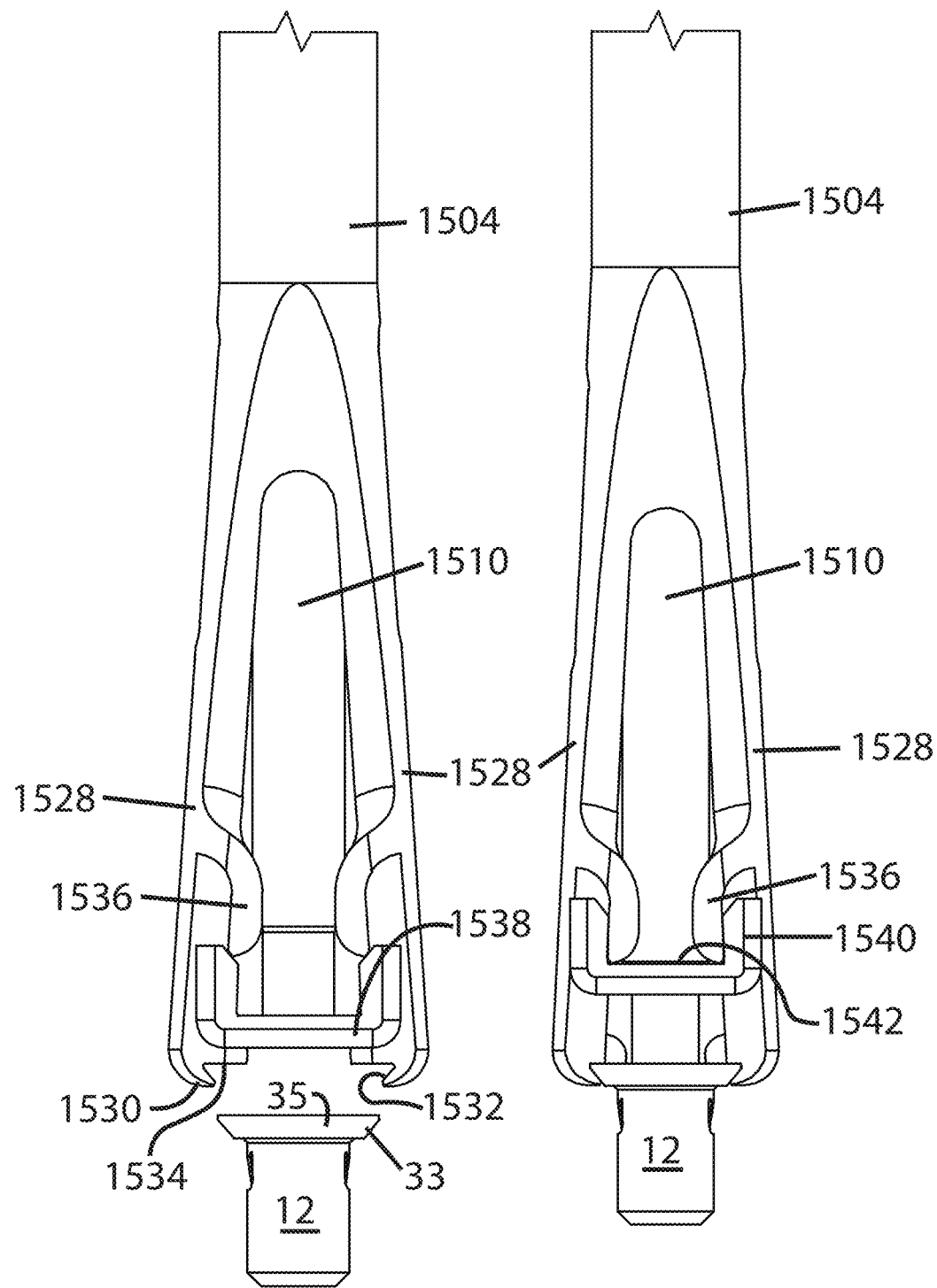
FIG. 47 is a schematic cross-sectional view of a distal end of the stem of the installation instrument of FIG. 44, with jaws thereof in an open position.
FIG. 48 is a view of the stem shown in FIG. 44, with jaws thereof in a closed position.

An exemplary configuration of the stem 1504 and pushrod 1510 are shown in more detail in FIGS. 47 and 48.

The distal end of the stem 1504 incorporates means for engaging and holding an anchor 12. In the illustrated example, the stem 1504 includes a pair of opposed jaws 1528 with tips 1530, which may be formed as integral, spring-like extensions of the stem 1504. The tips 1530 may be formed with lateral and axial engagement surfaces 1532, 1534 respectively, in order to engage lateral and axial faces, 33, 35 respectively of the anchor 12 (shown schematically in FIG. 47). The jaws 1528 are provided with axially-extending hooks 1536 which are set back from the tips 1530. A clip 1538 having a U-shape with axially-extending legs 1540 is disposed laterally between the jaws, in an axial position which is between the tips 1530 and the hooks 1536. The clip 1538 may have an opening 1542 passing therethrough, and the pushrod 1510 may be stepped, having a first portion at its distal end small enough to pass through the opening 1542, and a second portion sufficiently larger to engage the clip 1538.

Figures 32, 33:
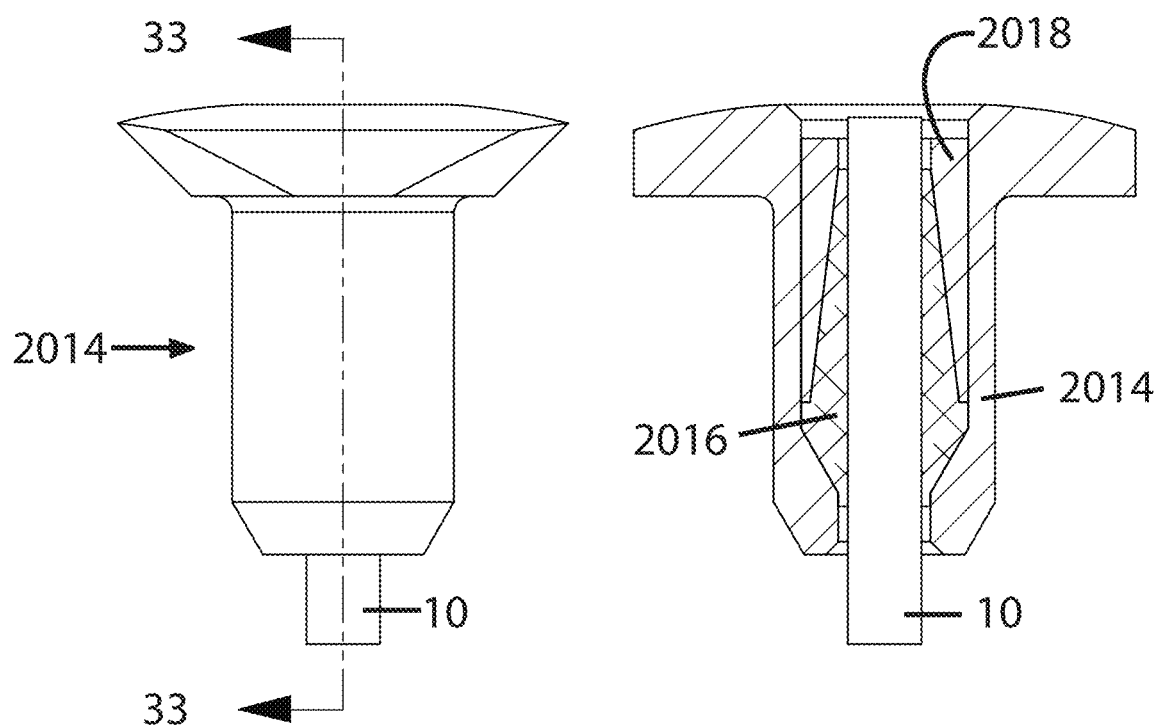
FIG. 32 is a schematic side elevation view of a portion of the anchor of FIG. 30 in a compressed condition.
FIG. 33 is a cross-sectional view of FIG. 32.

FIG. 47 shows the stem 1504 with the pushrod 1510 in a fully extended position, pushing the clip 1538 outwards and spreading the jaws 1528 apart so as to release the anchor 12. FIG. 48 shows the stem 1504 with the pushrod 1510 in a retracted position, allowing the clip 1538 to move inwards, engaging the hooks 1536, thereby pulling the jaws inwards so the tips 1530 engage the flange 32 of the anchor 12. In this position, the anchor 12 is securely held by the stem 1504 and may be manipulated as necessary. The clip 1538 secures the jaws 1528 in the closed position until such time as the pushrod 1510 is actuated, thus disengaging the clip in the jaws as shown in FIG. 33.

Figure 49:
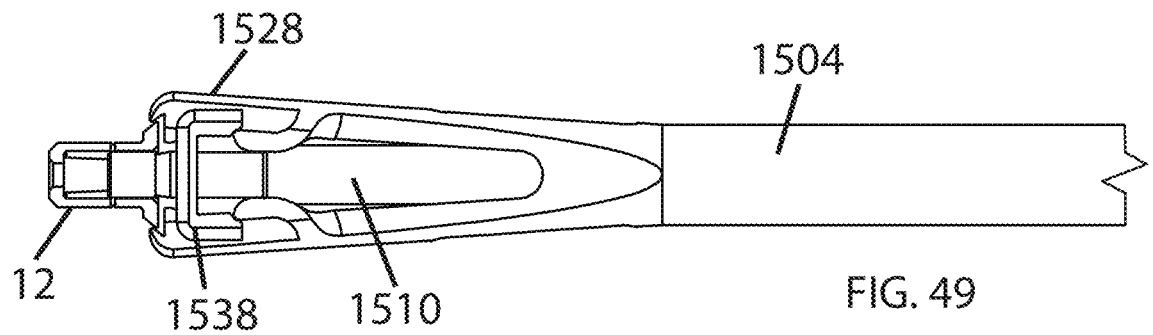
FIG. 49 is a schematic cross-sectional view of a distal end of the stem of the installation instrument of FIG. 44, showing an anchor loaded therein.
Figure 50:
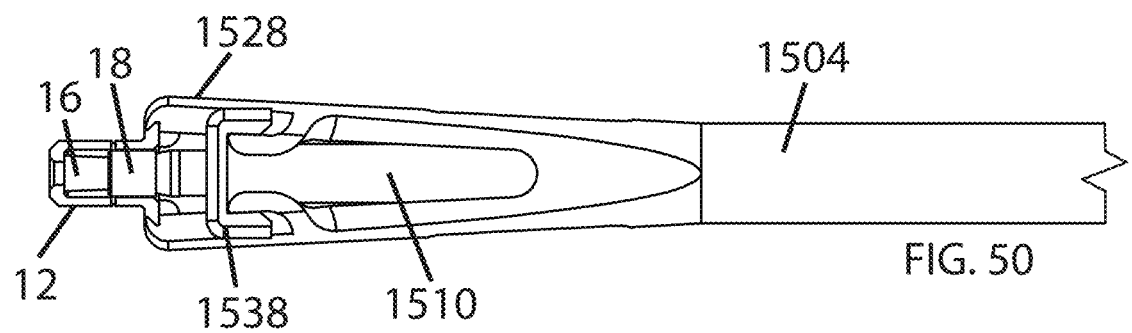
FIG. 50 is a view of the stem of FIG. 49, showing a clip in an engaged position.
Figure 51:
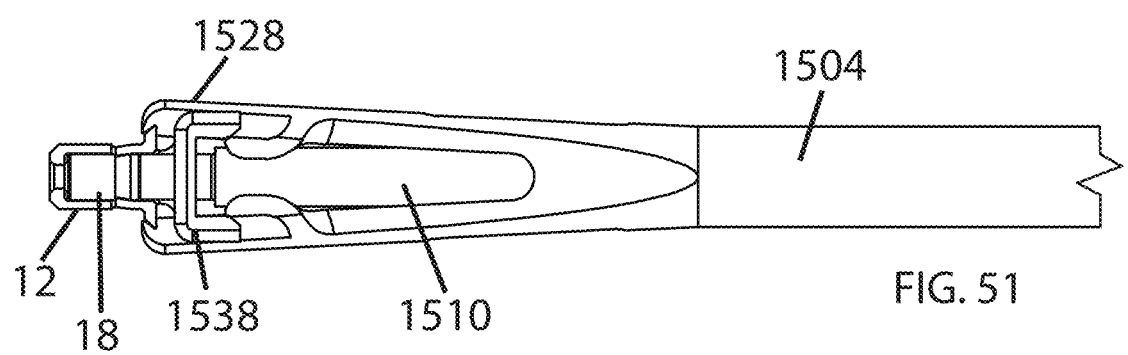
FIG. 51 is another view of the stem of FIG. 49, showing a pushrod thereof being actuated.
Figure 52:
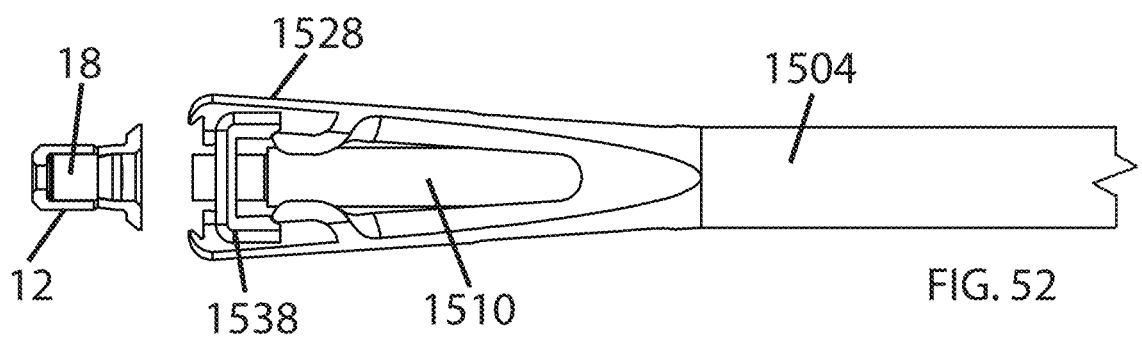
FIG. 52 is another view of the stem of FIG. 49, showing a clip in a released position, with the jaws opened to release the anchor.

FIGS. 49-52 show the sequence of operation of the insertion instrument 1500. FIG. 49 shows an anchor 12 received in the jaws 1528, with the clip 1538 is in a released position. FIG. 50 shows the clip 1538 in an engaged position, holding the jaws 1528 closed. The clip 1538 may be engaged manually, or may be pressed against a tool or fixture (not shown) in order to engage it. FIG. 51 shows the pushrod 1510 being actuated to press the sleeve 18 down over the collet 16. FIG. 52 shows the clip 1538 moved to the released position by the pushrod 1510, and the jaws 1528 open so that the insertion instrument can be removed.

FIGS. 53-58 illustrate an alternative stem 2504 and a method of its operation. The distal end of the stem 2504 includes pair of opposed jaws 2528 with tips 2530, which may be formed as integral, spring-like extensions of the stem 2504. The jaws 2528 flank a pushrod 2510 substantially similar to pushrod 1510 described above. The tips 1530 may be formed with V-shaped engagement surfaces 2532 in order to engage an anchor 12. The V-shaped engagement surfaces 2532 are especially suitable for engaging the chamfered surfaces 2037 of the flange 2032 of the anchor 2012. A generally tubular lock sleeve 2538 having conical end face 2540 surrounds the stem 2504.

FIGS. 53-58 show the sequence of operation of the alternative stem 2504. FIG. 53 shows the lock sleeve 2538 retracted from the jaws 2528. An anchor 2012 is ready to be picked up by the jaws 2538. The anchor 2012 may be held in this position by suitable packaging (not shown).

FIG. 54 shows the jaws 2538 sprung over top of and lightly engaging the flange 2032 of the anchor 2012 with spring pressure.

FIG. 55 shows the lock sleeve 2538 axially slid over the jaws 2538, applying radially inward compressive pressure to the jaws and securely retaining the anchor 2012.

FIGS. 56-57 shows successive stages of actuation of the pushrod to crimp a tensile member 10 in the anchor 2012, substantially as described above.

Three. 58 shows the lock sleeve 2538 retracted from the jaws 2538, allowing the stem 2504 two be detached from the anchor 2012.

Figure 59:
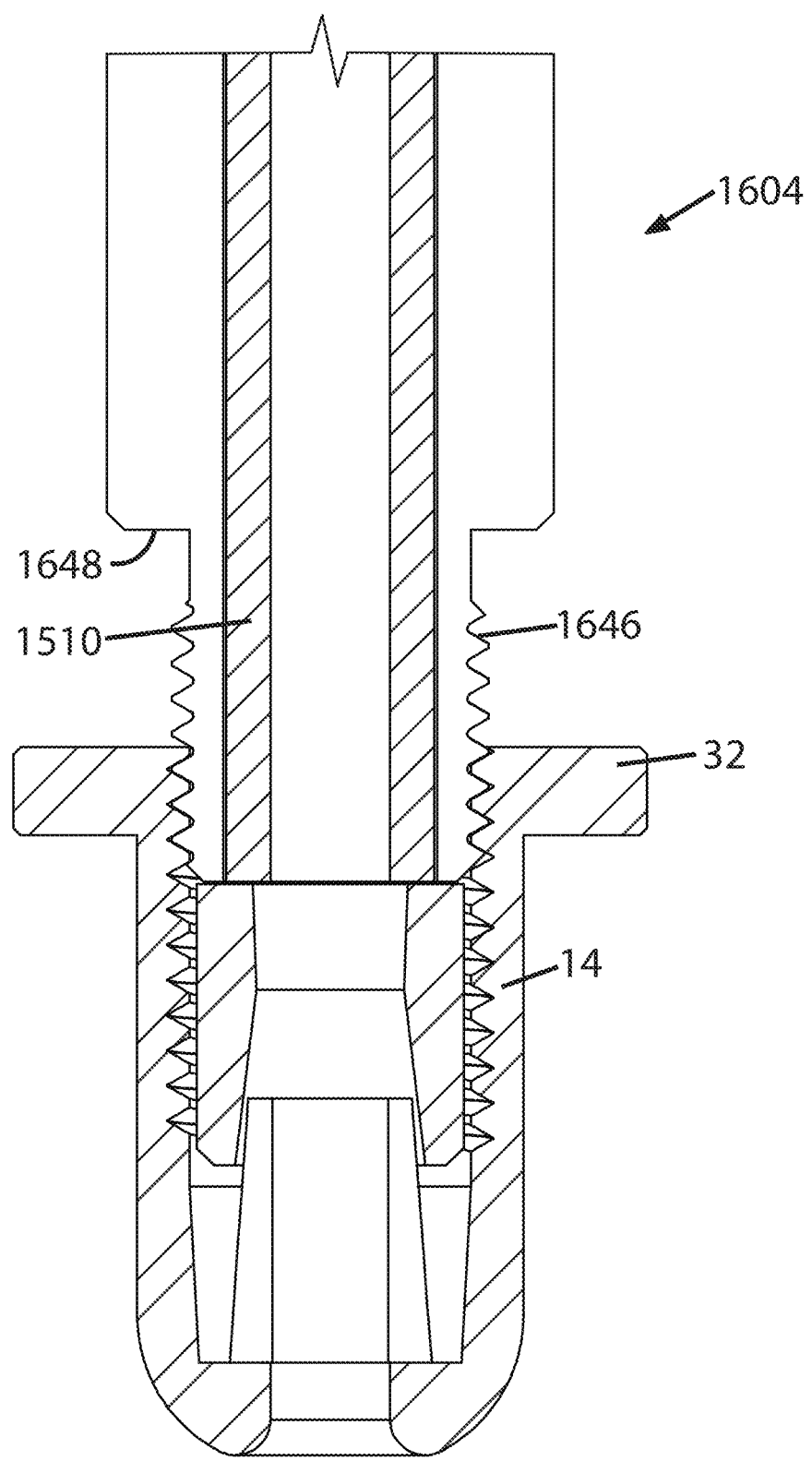
FIG. 59 is a schematic cross-sectional view of an alternative embodiment of an installation instrument stem.

FIG. 59 illustrates another alternative stem 1604. It includes male threads 1646 formed on a distal end which engage female threads formed on anchor housing 14. It also includes an axially-facing shoulder 1648. When fully threaded onto the stem 1604, the flange 32 of the housing 14 abuts the shoulder 1646. This construction provides a highly rigid interconnection between the housing 14 and the stem 1604 in order to maximize the surgeon's control and ability to manipulate the anchor 12. The hollow pushrod 1610 is mounted inside the stem and operates like the pushrod 1510 described above in order to swage the collet 16 when desired.

FIGS. 74 and 77-79 illustrate another alternative insertion instrument 3500 which may be used to insert, tension, and activate the anchors 12 described above. The insertion instrument 3500 is particularly suitable for use with the breakaway or snap-off anchor 3012 as shown in FIGS. 72-76. The basic components of the insertion instrument 3500 are a body 3502 having a handle, a hollow pushrod 3510 extending through the body 3502 and slidably movable between retracted and extended positions, and a driving mechanism 3512 for moving the pushrod 3510 between retracted and extended positions. The body 3502 may include a mechanical connector 3504 complementary to a connector 3029 of the anchor 3012. In the illustrated example, the body 3502 is provided with a connector 3504 in the form of screw threads.

Figure 74:
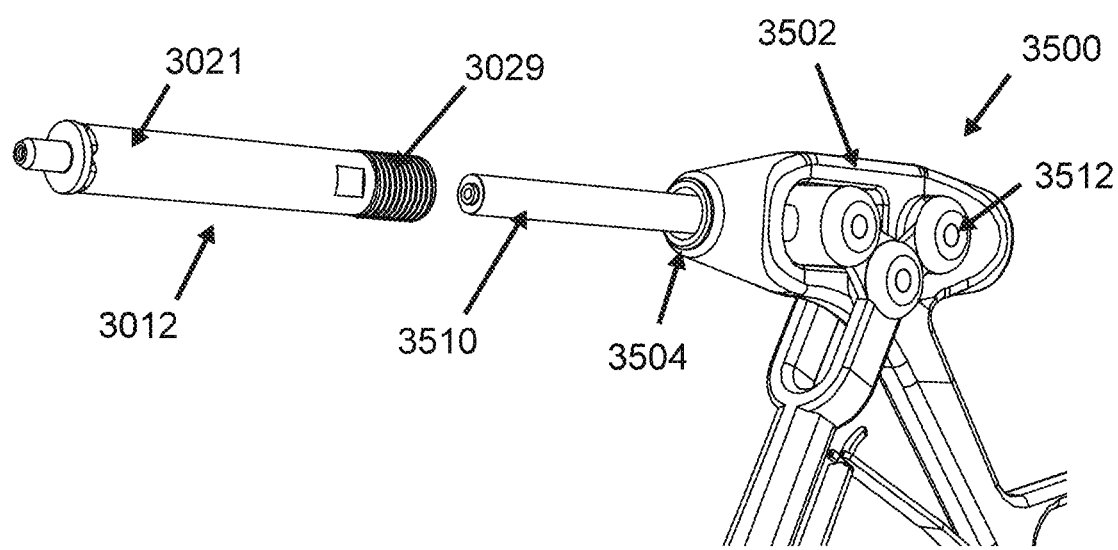
FIG. 74 is a schematic perspective exploded view of the anchor of FIG. 72 in combination with an insertion instrument.
Figure 77:
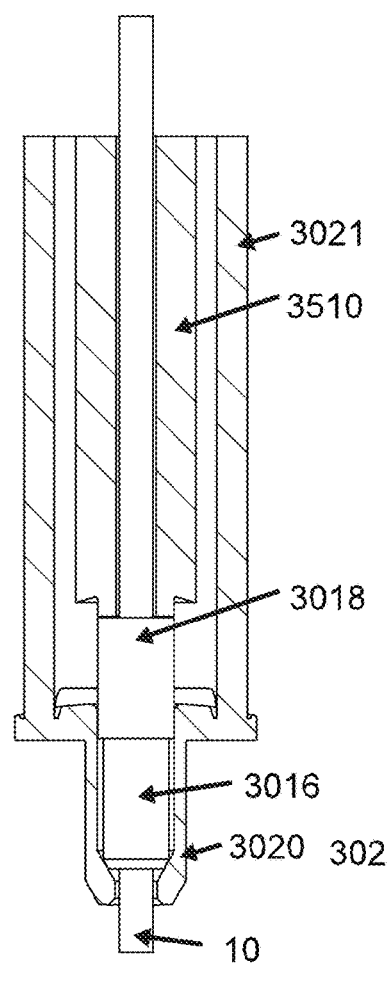
FIG. 77 is a schematic cross-sectional view of the anchor FIG. 72 coupled to an insertion device, prior to a swaging operation.
Figure 78:
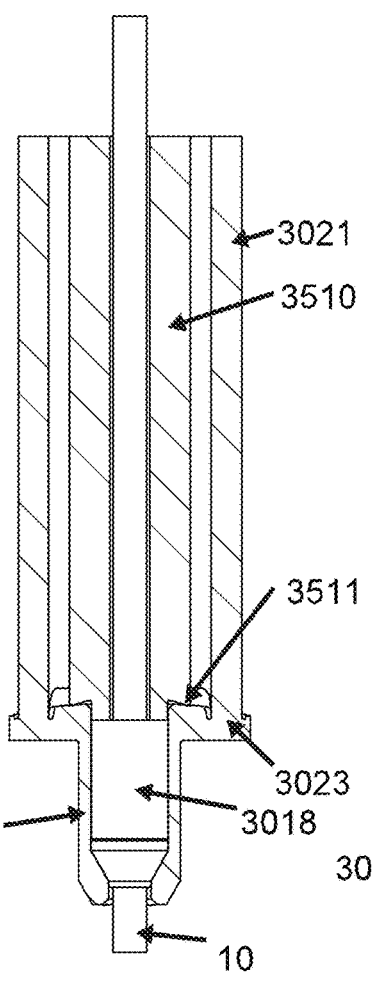
FIG. 78 is a schematic cross-sectional view of the anchor of FIG. 72, upon completion of a swaging operation.

The operation of the insertion instrument 3502 to implant anchor 3012 may be better understood with reference to FIGS. 74 and 77-79. As shown in FIG. 74, the anchor 3012 may be coupled to the instrument 3500 using their mutual connectors 3029, 3504. Referring to FIG. 77, the pushrod 3510 initially rests against an end surface of the sleeve 3018 with essentially no load applied. A tensile member 10 passes through the collet 3016, the sleeve 3018, and the hollow pushrod 3510.

Prior to any swaging operation, the tensile member 10 may be tensioned using methods described elsewhere herein. Once desired tension has been established, the instrument 3500 is actuated. More specifically, the pushrod 3510 extends outward from the body 3502. This applies a compressive load to the sleeve 3018, causing it to interact with the body portion 3020, collet 3016, or both in order to swage the collet 3016 around the tensile member 10, thus retaining the tensile member 10 in-place with the desired amount of tension. As the swage cycle is completed, a shoulder 3511 of the pushrod 3510 makes physical contact with the flange 3032 of the housing 3014 (see FIG. 78).

It will be understood that the extension housing 3021 is mechanically coupled to the body 3502 of the instrument 3500. Accordingly, extension of the pushrod 3510 results in a tensile load being applied to the breakaway structure 3023 described above. This load is transferred through some combination of friction between the sleeve 3018 and/or physical contact between the shoulder 3511 in the flange 3032. As described above, the step of swaging is accomplished using a first predetermined tensile load.

Figure 79:
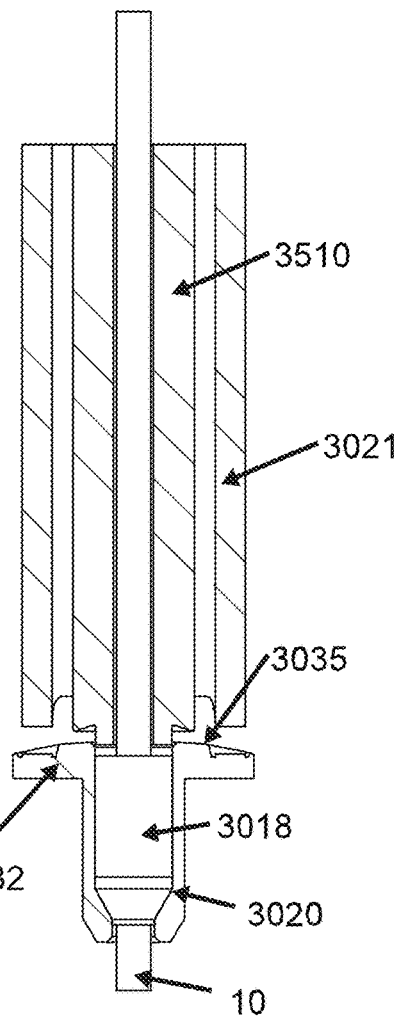
FIG. 79 is a schematic cross-sectional view of the anchor of FIG. 72, subsequent to completion of a swaging operation, showing an extension portion of the housing of anchor 72 being separated from the remainder of the anchor.

Once the swaging procedure is completed, the pushrod 3510 is further actuated as shown in FIG. 79 to apply a tensile load sufficient to fracture the breakaway structure 3023 and separate the housing body portion 3020 from the extension portion 3021. This is accomplished using a second predetermined tensile force greater than the first predetermined tensile load. Once accomplished, the instrument 3500 with the housing extension portion 3021 still attached may be withdrawn, leaving the anchor 3012 in-place with the tensile member 10 secured with the desired amount of tension. Any remaining portion of the breakaway structure 3023 is below flush from the outer surface 3035 of the flange 3032. It thus does not protrude to irritate or injure the patient or the surgeon, and no additional trimming operation is required.

Figure 60:
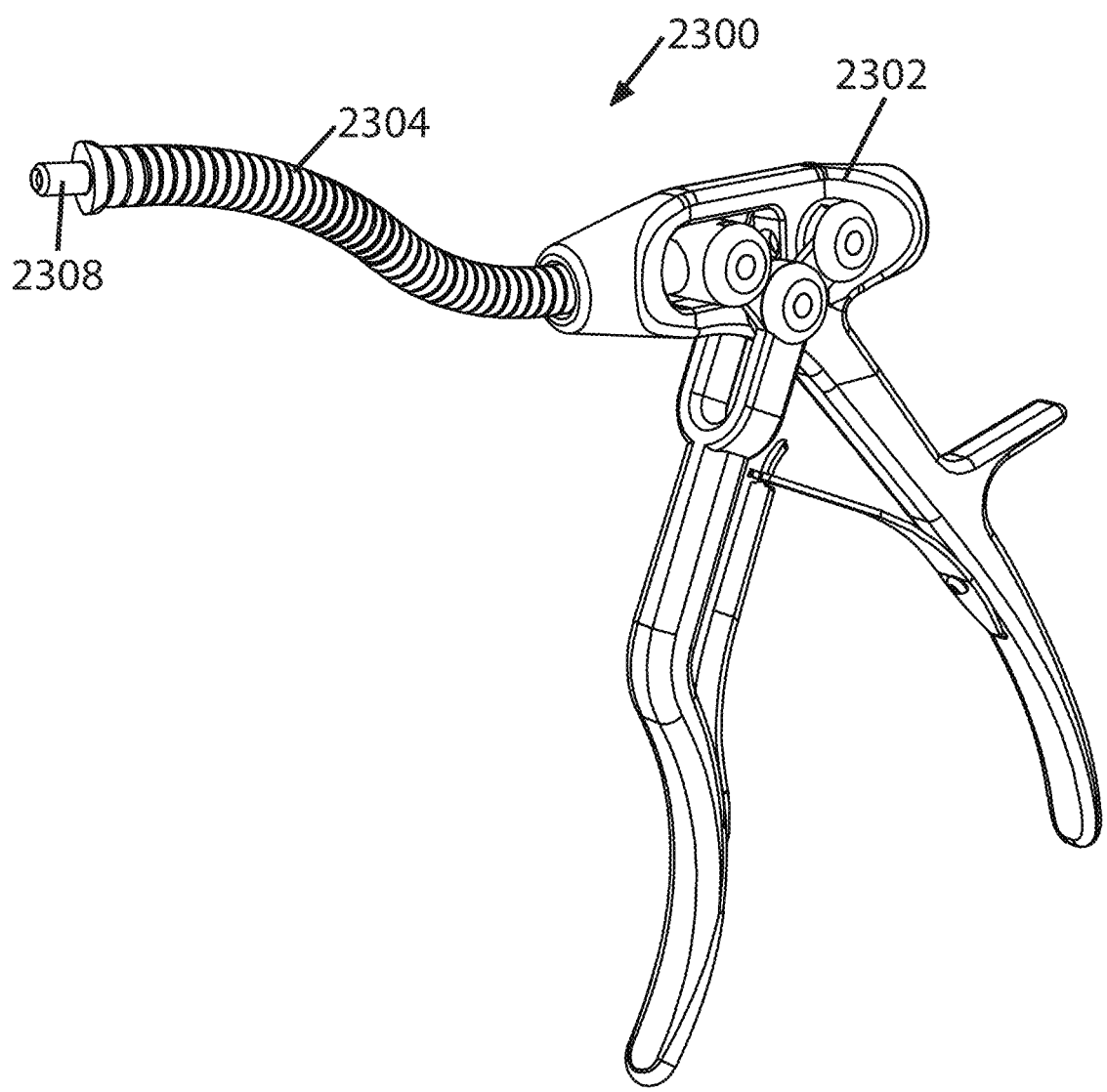
FIG. 60 is a schematic perspective view of an installation instrument having an alternative flexible stem.

FIG. 60 illustrates an alternative insertion instrument 2300. It includes a stem 2304 extending from the body 2302 and having an anchor connection mechanism 2308 disposed at a distal end thereof. The stem 2304 may be flexible as a result of its material selection. Alternatively, it may incorporate linked segments, corrugations, or similar structures to provide flexibility. A hollow pushrod (not visible), which may be flexible, extends through the interior of the stem 2304 and is slidably movable between retracted and extended positions. The hollow pushrod operates like the pushrod 1510 described above in order to swage the collet 16 when desired.

Figure 62:
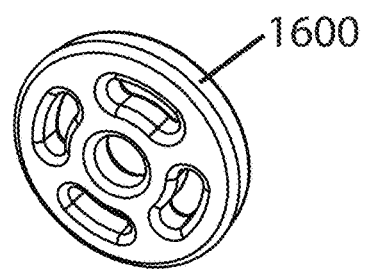
FIG. 62 is a schematic perspective view of a button anchor.
Figure 63:
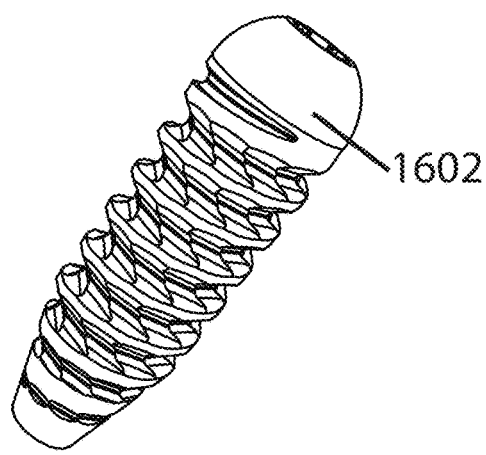
FIG. 63 is a schematic perspective view of a suture anchor.
Figure 64:
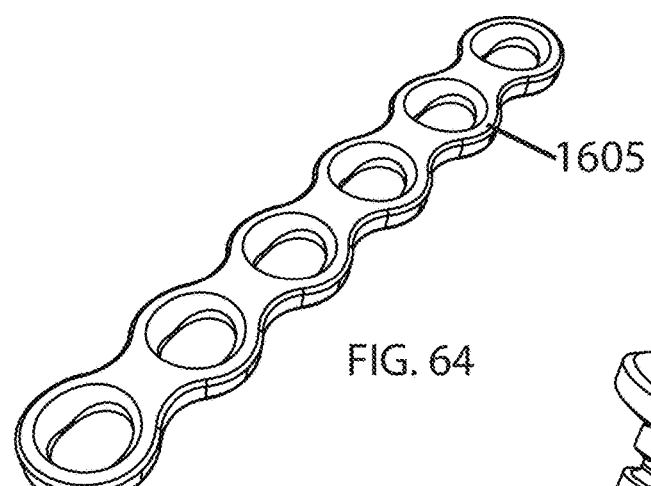
FIG. 64 is a schematic perspective view of an anchor plate.
Figure 65:
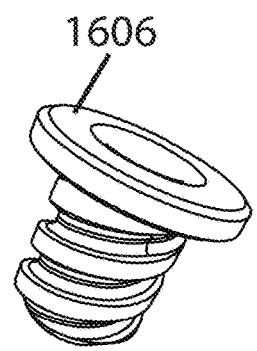
FIG. 65 is a schematic perspective view of a grommet.
Figure 95:
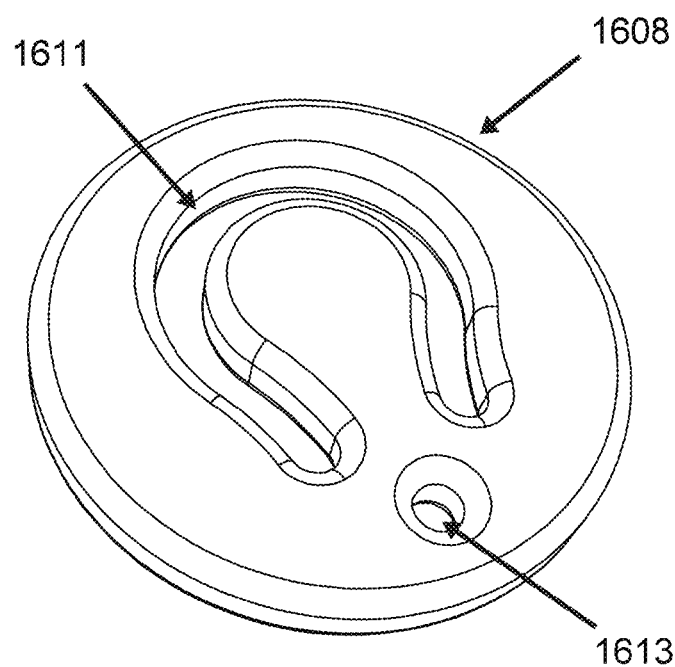
FIG. 95 is a schematic perspective view of an exemplary suture button.
Figure 96:
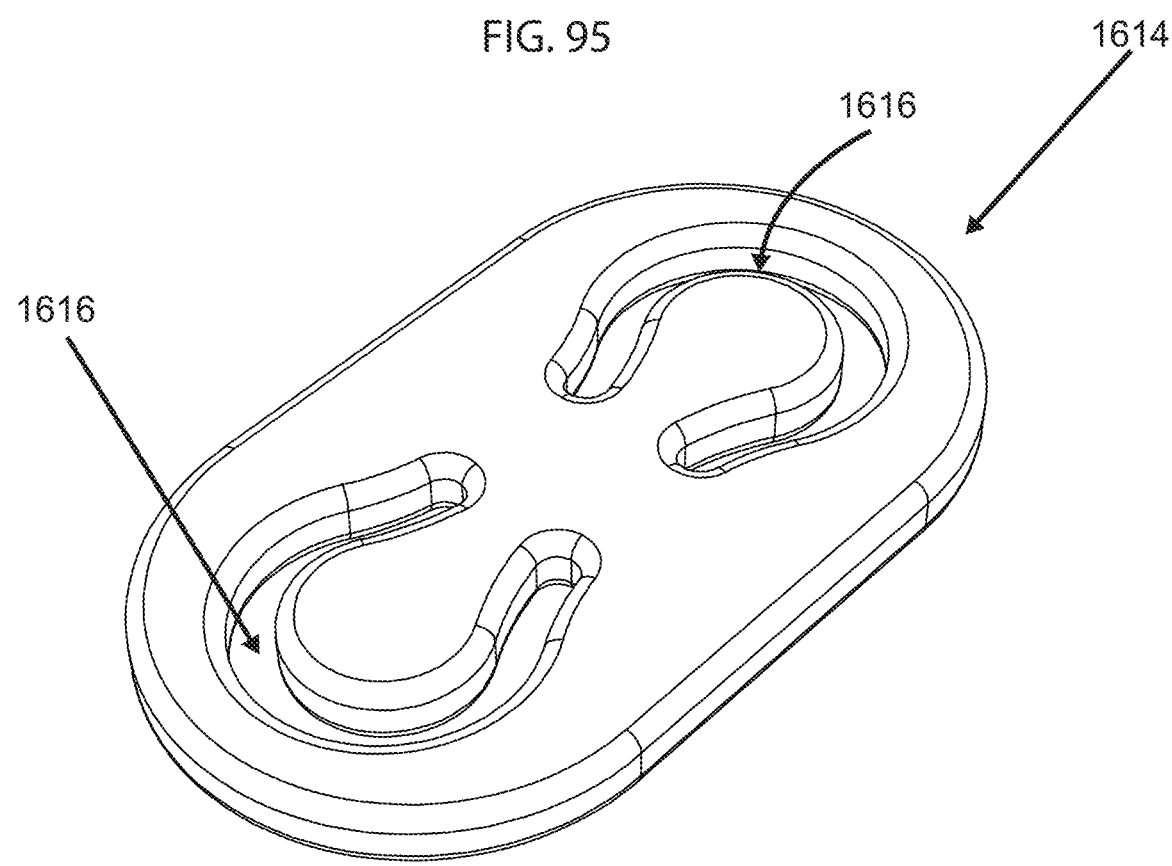
FIG. 96 is a schematic perspective view of another exemplary suture button.

Other anchoring devices may be used in conjunction with the various embodiments of anchors 12 described above in order to implant a tensile member 10. FIGS. 62-65, 95, and 96 illustrate examples of various anchoring devices. FIG. 62 illustrates a "button" 1600 to which a tensile member may be tied. FIG. 63 illustrates a screw-in suture anchor 1602. FIG. 64 illustrates a plate 1605 having a series of openings formed therein, each of which may receive an anchor. FIG. 65 illustrates a grommet 1606 which has a smooth interior surface to allow a tensile member to pass freely therethrough. The grommet 1606 may be formed from any biocompatible material. The grommet 1606 may be externally threaded as shown, or be sized for a press fit. If a flexible material is used, the grommet 1606 could extend through a complete bone passage. FIG. 95 illustrates another type of button or washer 1608 through which a tensile member may be tied or passed. The button 1608 includes a U-shaped slot 1611 as well as a hole 1613 which can accept a pin or wire to further increase stability and fixation. FIG. 96 illustrates another type of button or washer 1614 through which a tensile member may be tied or passed. The washer 1614 is generally racetrack-shaped in plan view and includes two opposed U-shaped slots 1616. The portion of the washer 1614 between the 2 slots 1616 may incorporate tapered sides giving it a "dog-bone" shape.

Figure 66:
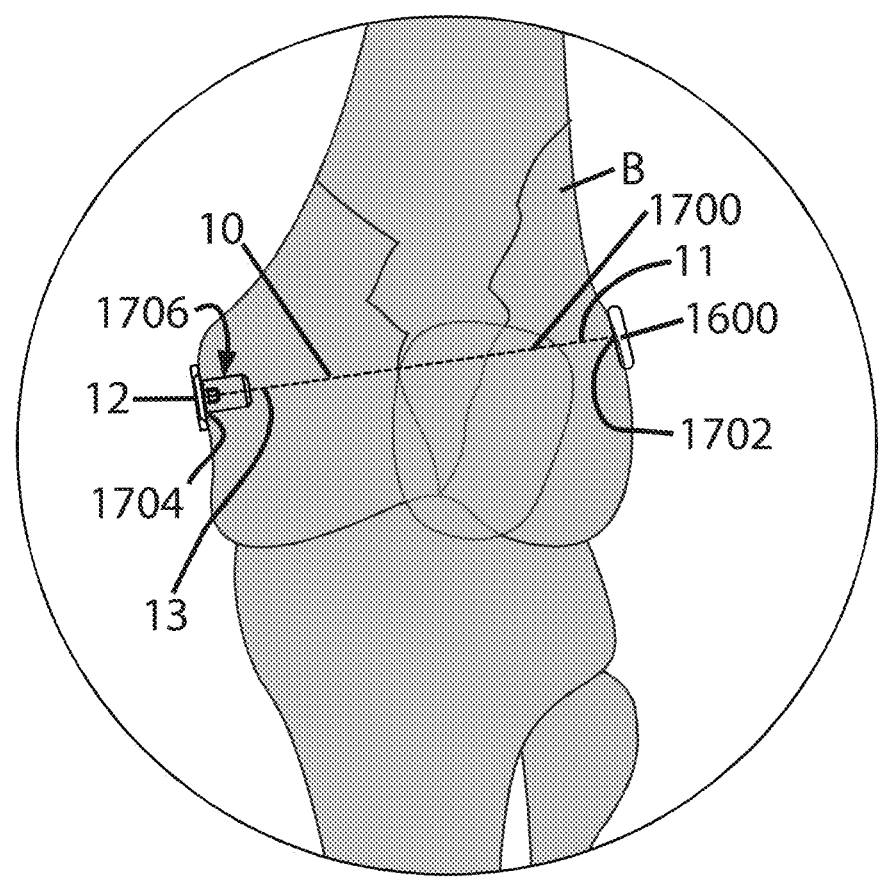
FIG. 66 is a schematic diagram of a tensile member implanted in a human femur.

The method of applying these principles for implantation and tensioning of a tensile member 10 will now be described in more detail with reference to FIGS. 2 and 66. This particular example illustrates the use of a tensile member 10 to stabilize a human femur. It will be understood that this is merely an example, and that the apparatus and methods described herein may be used to secure and tension a tensile member in any application.

Initially, a tensile member 10 is provided. An appropriate route through bone "B" or other tissue is determined, and a passage 1700 having first and second ends 1702, 1704 is drilled in the bone B. The second end 1704 of the passage 1700 is prepared to receive the anchor 12, for example by drilling an appropriately-sized bore 1706 communicating with the passage 1700.

A first end 11 of the tensile member 10 is secured in the first end of the passage 1700. This may be done using the anchor 12 as described above, or some other type of anchor. In the illustrated example, the first end 11 of the tensile member is secured to a button 1600 as described above. The tensile member 10 is threaded through the passage 1700 so that its second end 13 extends from the second end 1704 of the passage 1700.

An anchor 12 according to one of the embodiments described above is loaded into the installation instrument 1500 described above or another appropriate instrument. The second end 13 of the tensile member 10 is threaded through the anchor 12 and the installation instrument 1500 and optionally through the tensioner 1520.

The installation instrument 1500 is then used to seat to the anchor 12 into the bore 1706 formed in the bone B. The seating process may include methods such as simple axial driving, an adhesive bond, threading, screwing into the bone B with small screws through the flange, or counter-sinking into the bone surface.

With the anchor 12 seated, but the collet 16 not yet swaged, tension may be applied to the tensile member 10, for example using the tensioner 1520 described above. This is referred to as "provisional tensioning".

The properties of the anchor 12 and the installation instrument 1500 enables provisional and permanently stable tensioning of the tensile member 10, and allows the surgeon to load-cycle and re-tension the tensile member 10 before setting final tension. More specifically, With the insertion instrument 1500 abutted against the flange 32 of the anchor 12, tension can be added and removed. The ligament or joint being repaired can be load cycled by moving it through some or all of its range of motion before setting final tension. It is noted that the final tension of any of the tensile members described herein may be selected to suit a particular surgical application. More specifically, the final tension may be selected in concert with the material properties of the tensile member to result in a final construct which is "live", that is, which maintains a tensile load at a predetermined value or range of values post-implantation. This may be effected, for example, by selecting the tensile member final dimension or strain applied thereto such that the tensile member is in its elastic range. The desired tensile load (and thus the compressive load on the anatomical structure) is thus maintained even if a joint undergoes movement, shifting, swelling, or thermal expansion/contraction. This property may be referred to as "constant compression".

In addition to producing more accurate and repeatable suture tensions, provisional tensioning with a load-setting/load-reading instrument (especially when the suture crosses the axis of a joint, such as a medial collateral ligament (MCL) repair technique) allows the surgeon to visualize the increase/decrease in tension throughout the joint range of motion (max flexion to max extension). This allows the surgeon to ensure that the tension stays within an acceptable range—and this check is done after load cycling the ligament in question to ensure the settle-in period is complete.

Once the surgeon is satisfied with the tension established, the insertion instrument 1500 may be activated. The driving mechanism 1512 is used to force the pushrod 1510 towards the actuated position. This drives the sleeve 18 down over the collet 16, thus swaging the collet 16 around the second end 13 of the tensile member 10. This swaging action takes place with the collet 16 bottomed out at the first end 22 of the housing 14 of the anchor 12. Accordingly, the act of swaging causes little to no change in the tension applied to the tensile member 10.

As the sleeve 18 reaches the fully-actuated position, the sleeve retention features of the housing 14 and the sleeve 18 become mutually engaged. FIG. 2 shows an example in which the locking tabs 66 of the housing 14 engage the annular step 90 of the sleeve 18. This prevents retraction of the sleeve 18 and sets the tensile member 10 permanently in position, with the predetermined amount of tension. The tensile member 10 is thus secured to the bone B with a desired tension.

For any of the anchors and any of the procedures described herein, it may be desirable to cut off the tensile member 10 so that it does not protrude beyond the anchor once the swaging operation is completed. This avoids injury or irritation to the patient.

FIGS. 88-93 illustrate exemplary cutters which may be used to sever the tensile member 10 at a below-flush location relative to the anchor.

For example, referring to FIG. 88, a cutting instrument 4000 may include a body 4002 with the plurality of collapsible, tapered jaws 4004 which have a convex nose 4006. These are shaped so as to protrude into a recess 4008 which may be formed in the housing 14 of the anchor 12, or alternatively in the housing of any of the anchors described herein.

FIG. 89 shows the cutting instrument 4000 in use, where a tensile member 10 has been passed through the anchor 12 and secured in place with the collet 16 and swaged 18. The collapsible jaws 4004 are in an extended position in which they slide over the tensile member 10 and allow the nose 4006 to fit into the recess 4008. FIG. 90 shows a cutting instrument 4000 being actuated, with the collapsible tapered jaws being drawn into the body 4002, thus causing them to collapse inward and sever the tensile member 10. It will be noted that the cutting plane 4010 of the jaws 4004 is below flush of an outer surface of the housing 14.

Figures 91, 92:
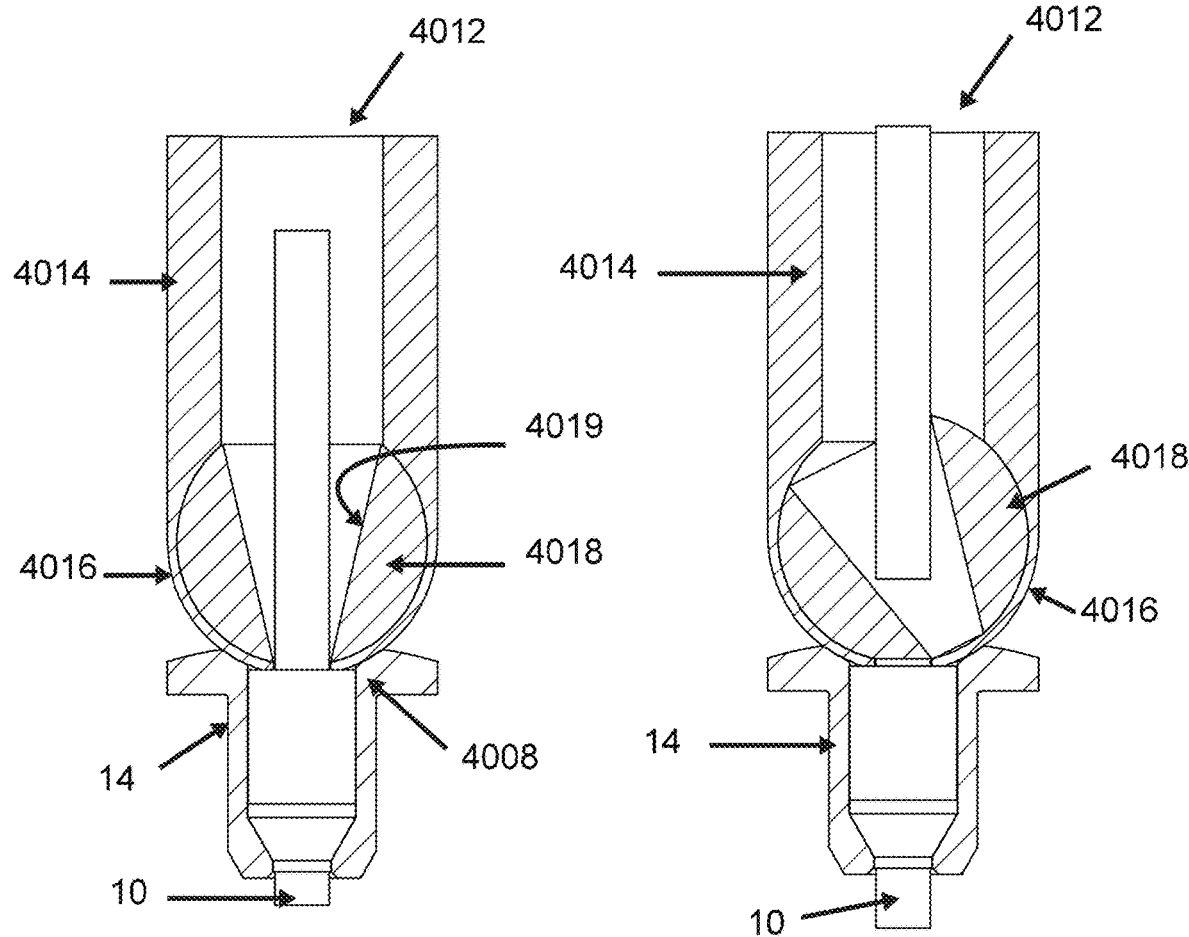
FIG. 91 is a cross-sectional view of a portion of an alternative cutting instrument in an open position.
FIG. 92 is a cross-sectional view of the cutting instrument of FIG. 91 in a closed position.

As another example, FIG. 91 illustrates a cutting instrument 4012 including a body 4014 with a convex nose 4016. Contained within the convex nose 4016 is a cylindrical or spherical jaw 4018 having a central bore 4019 sized to slide over the tensile member 10. Means (not shown) may be provided for rotating the jaw 4018 relative to the body 4014.

FIG. 91 shows the cutting instrument 4012 in position with the tensile member 10 passed through the jaw 4018 and the convex nose 4016 received in a recess 4008 of an anchor housing 14. FIG. 92 shows the cutting instrument 4012 being actuated, with the jaw 4018 being rotated, thus causing it to sever the tensile member 10. As with the cutting instrument 4000, it is noted that the cutting plane 4010 of the jaw 4016 is below flush of an outer surface of the house 14.

Figure 93:
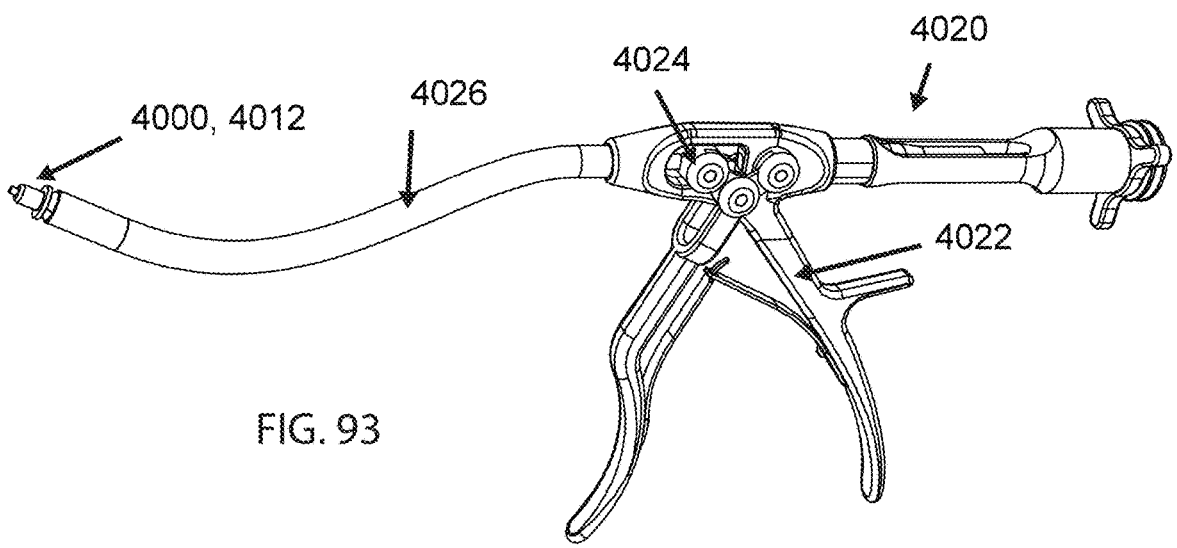
FIG. 93 is a schematic perspective view of an operating mechanism suitable for actuating the cutting instrument shown in FIGS. 89-92.

FIG. 93 shows an exemplary cutting instrument 4020 similar to the instrument 1500 described above, comprising a handle 4022 and a lever-actuated mechanism 4024 operable to operate the jaws 4004 or 4018 described above. The actuation mechanism 4020 may be coupled to the cutting instrument 4000 or 4012 with a neck 4026 which is rigid or flexible.

Figure 61:
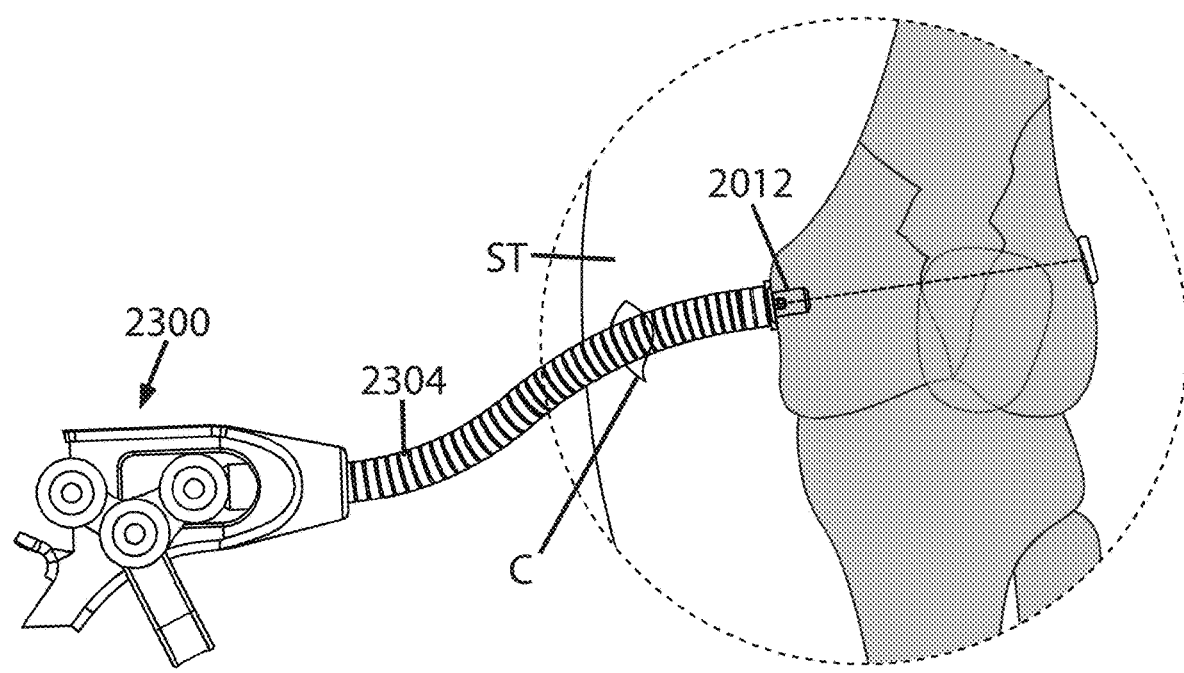
FIG. 61 is a schematic view showing the installation instrument of FIG. 60 being used to implant an anchor in a human need joint.

The procedure described above with reference to FIG. 66 may be performed as a conventional or "open" procedure or in an arthroscopic procedure. FIG. 61 illustrates how the alternative insertion instrument 2300 may further facilitate an arthroscopic procedure. The stem 2304 is shown as being flexed in a curved shape so that it can pass through a small closed incision "C" in the soft tissue "ST" surrounding the joint. The other steps in the procedure described above would be identical.

Figure 69:
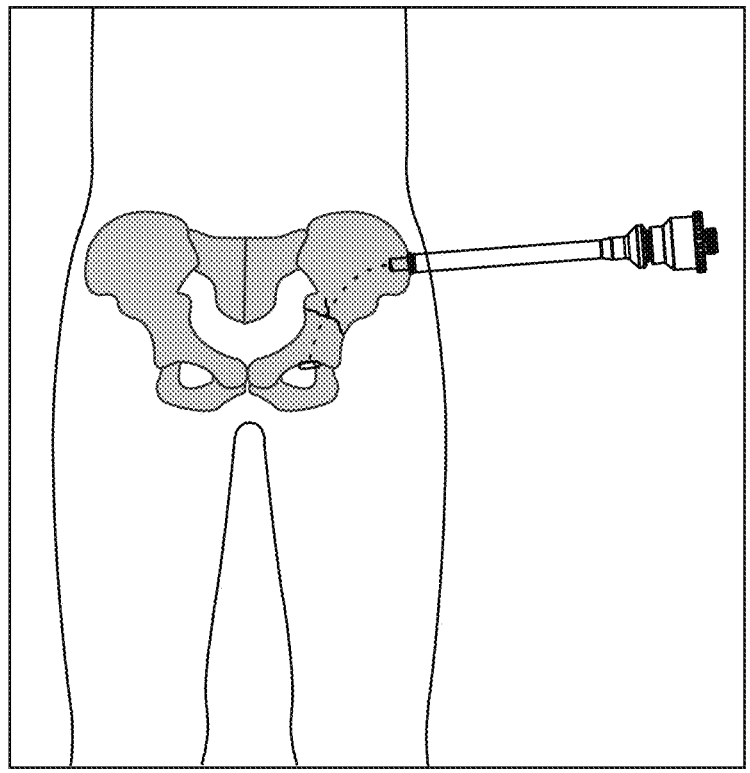
FIG. 69 is a schematic view showing an arthroscopic procedure in which a rigid stem is used to position an anchor in the pelvic region, close to the superficial surface of the skin.
Figure 70:
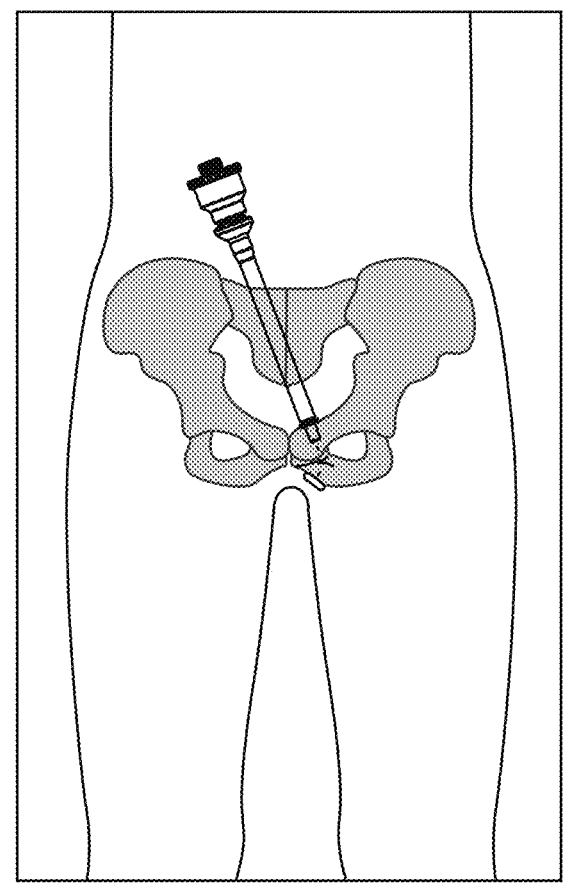
FIG. 70 is a schematic view showing an arthroscopic procedure in which a rigid stem is used to position an anchor in the pelvic region, far from the superficial surface of the skin.
Figure 71:
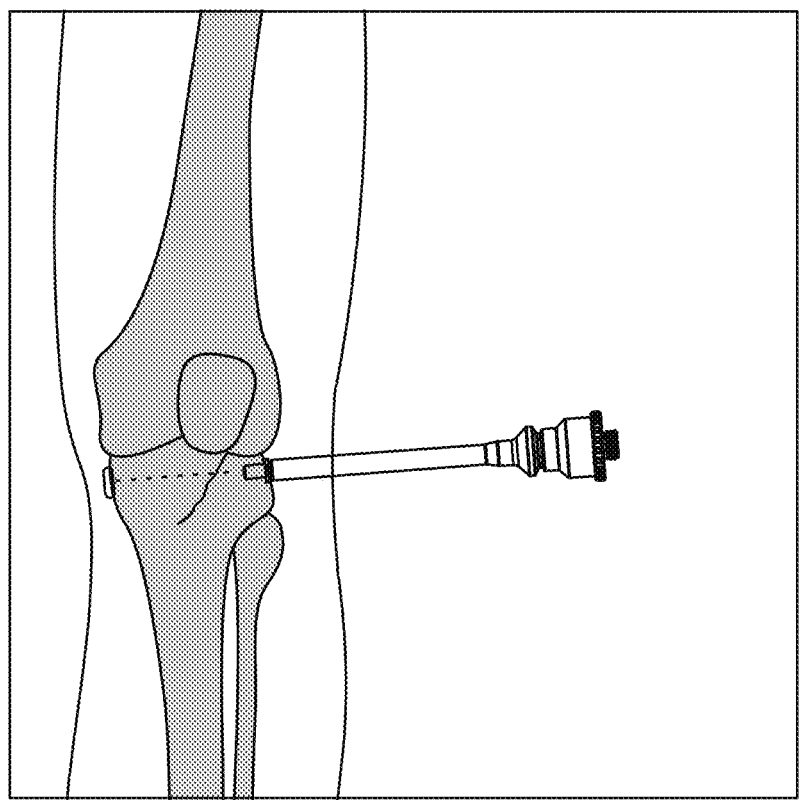
FIG. 71 illustrates an arthroscopic procedure in which a rigid stem is used to position an anchor in the knee region, close to the superficial surface of the skin.

FIG. 69 illustrates an arthroscopic procedure in which a rigid stem is used to position the anchor in the pelvic region, close to the superficial surface of the skin. 70 illustrates an arthroscopic procedure in which a rigid stem is used to position the anchor in the pelvic region, far from the superficial surface of the skin. 70 illustrates an arthroscopic procedure in which a rigid stem is used to position the anchor in the knee region, close to the superficial surface of the skin.

Figure 67:
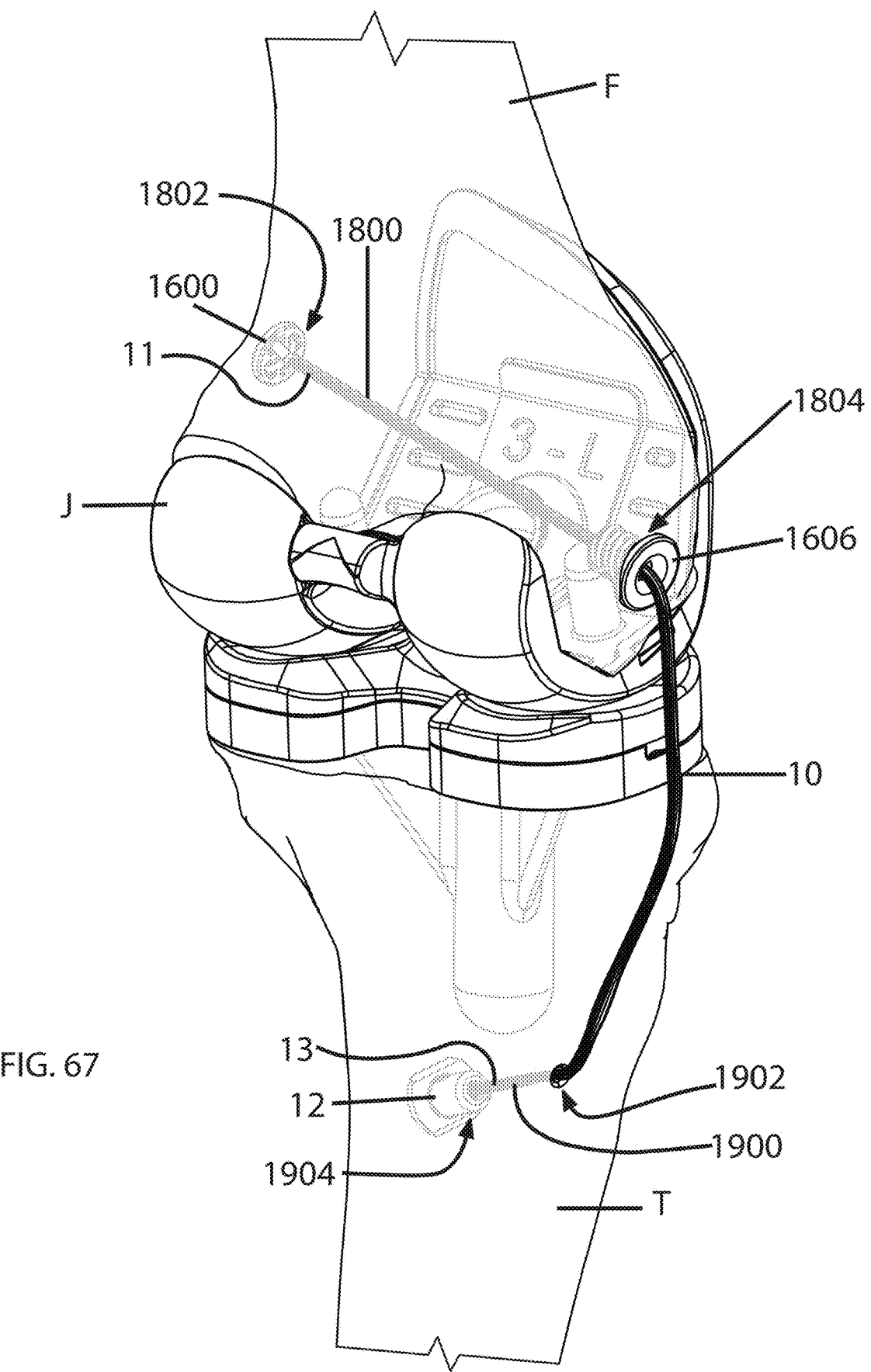
FIG. 67 is a schematic perspective view of a tensile member implanted in a human knee joint.

As noted above, apparatus and methods described above may be used to implant tensile members 10 for numerous different types of repairs and procedures. One specific example where the apparatus and methods are useful is to implant a tensile member in conjunction with a total knee replacement (TKR). This is referred to as a tension ligament augmentation (TLA) of the knee joint. FIG. 67 shows an example of a human knee joint comprising a portion of the "F" articulated with the tibia "T". The knee joint has implanted therein an artificial joint "J", the structure of which is outside the scope of the present invention.

A first passage 1800 having first and second ends 1802, 1804 extends through the femur F. A second passage 1900 having first and second ends 1902, 1904 extends through the tibia T. The second end 1904 of the second passage 1900 is prepared to receive the anchor 12.

A first end 11 of the tensile member 10 is secured in the first end 1802 of the first passage 1800 by an anchoring element such as a button 1600. A grommet 1606 is secured in the second end 1804 of the first passage 1800, and the tensile member 10 passes through the grommet 1606. The grommet 1606 protects the bone (especially if the bone is compromised) from rubbing and wear.

The tensile member 10 further extends around the lateral aspect of the knee joint J down along the upper portion of the tibia T and into the first end 1902 of the second passage 1900. The second end 13 of the tensile member 10 extends through the second passage, exiting at the second and 1904 of the second passage 1900.

An anchor 12 is described above is implanted in the second in 1902 of the second passage 1900. The second end 13 of the tensile member 10 extends through the anchor 12. The anchor 12 may be installed, and the tensile member 10 may be tensioned and swaged in place using the insertion tool 1500 and methods substantially as described above.

One type of repair is a fracture repair. Examples of fracture repairs are shown in FIGS. 97-102.

Figure 97:
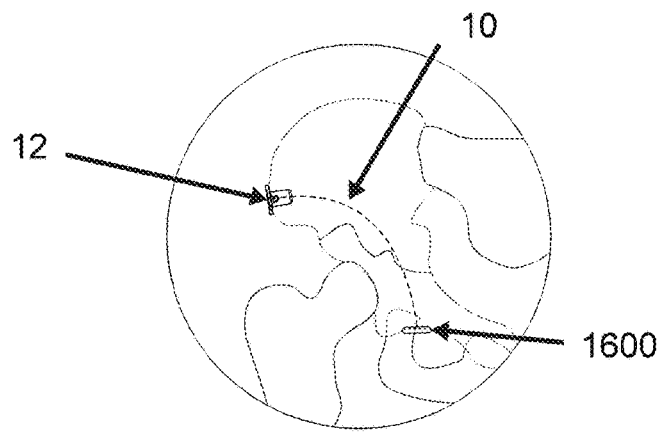
FIG. 97 is a schematic diagram showing reduction of a pelvic brim fracture.

FIG. 97 illustrates a pelvic brim fracture reduced with tension applied across the fracture site by means of a tensile member 10 is, extending through a passage formed in the bone and tensioned as described above, and secured at one end by an anchor (e.g. anchor 12 as described above) and at the other end by a button (e.g. button 1600 as shown in FIG. 62).

Figure 98:
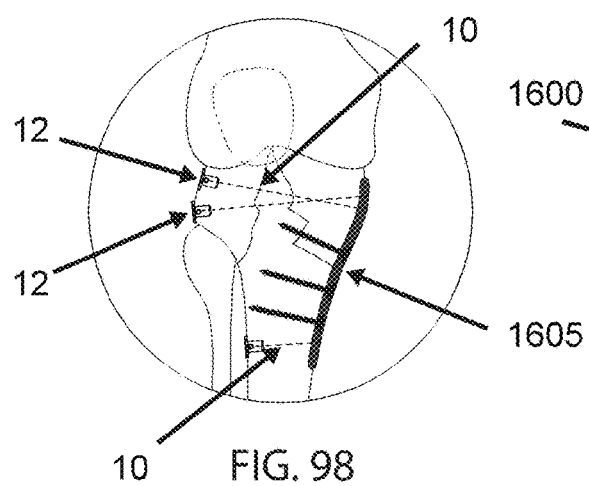
FIG. 98 is a schematic diagram showing reduction of a tibial epicondyle fracture.

FIG. 98 shows a tibial epicondyle fracture reduced with tension applied transversely by means of several tensile members 10 extending through passages formed in the bone and tensioned as described above. One end of each tensile member is secured by an anchor (e.g., anchor 12 as described above), and the opposite ends of the tensile members 10 are secured to a plate (e.g. plate 1605 shown in FIG. 64).

Figure 99:
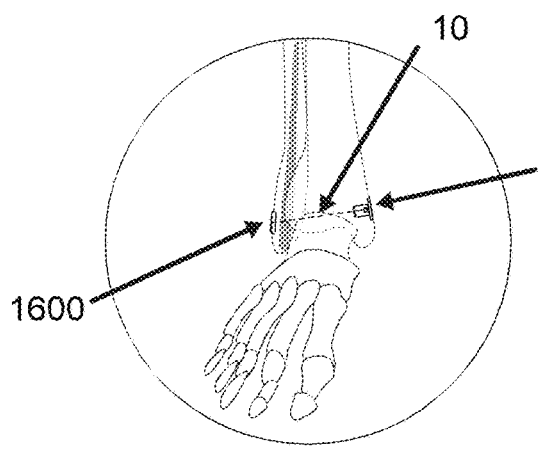
FIG. 99 is a schematic diagram showing reduction of a fibula fracture.

FIG. 99 shows a fibular fracture reduced longitudinally with a nail and transversely by means of a tensile member 10 extending through a passage formed in the bone and tensioned as described above. One end of the tensile member 10 is secured by an anchor (e.g., anchor 12 as described above), and the opposite end of the tensile member 10 is secured to a button (e.g., button 1600 as shown in FIG. 62).

Figure 100:
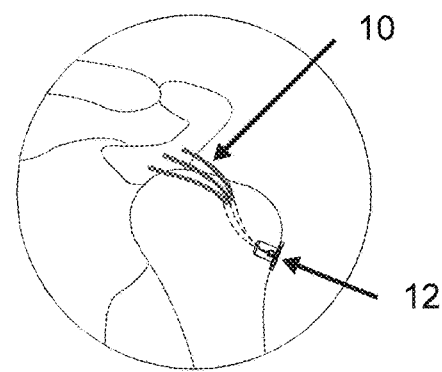
FIG. 100 is a schematic diagram showing tensioning of a rotator cuff against the proximal humerus.

FIG. 100 shows a rotator cuff tensioned down against the proximal humorous by means of a tensile member 10 looped through the rotator cuff, with its distal ends tensioned as described above and secured by an anchor (e.g., anchor 12 as described above).

Figure 101:
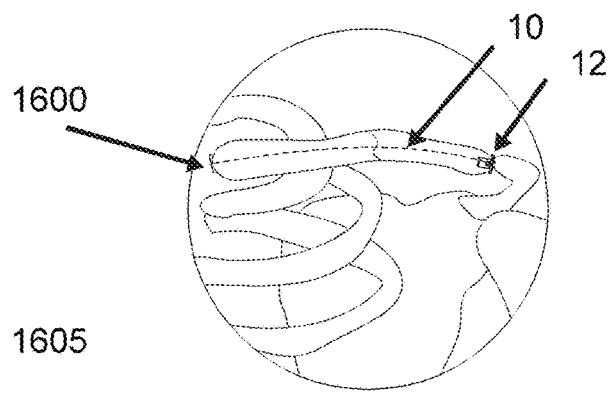
FIG. 101 is a schematic diagram showing reduction of a clavicle fracture.

FIG. 101 shows a clavicle fracture reduced with tension applied along the longitudinal axis by means of a tensile member 10 extending through a passage formed in the bone and tensioned as described above. One end of the tensile member 10 is secured by an anchor (e.g., anchor 12 as described above), and the opposite end of the tensile member 10 is secured to a button (e.g., button 1600 as shown in FIG. 62).

Figure 102:
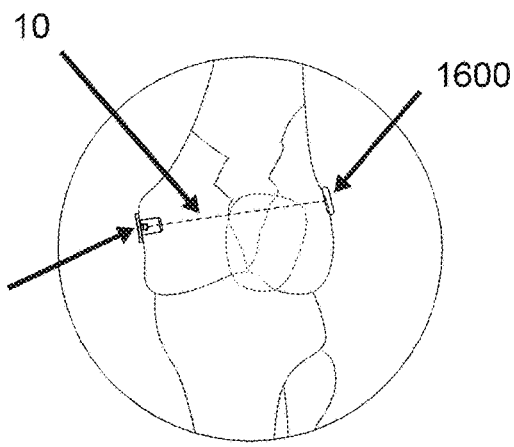
FIG. 102 is a schematic diagram showing reduction of a femoral epicondyle fracture.

FIG. 102 shows a for moral epicondyle fracture reduced attention applied transversely across by means of the tensile member 10 extending through a passage formed in the bone and tensioned as described above. One end of the tensile member 10 is secured by an anchor (e.g., anchor 12 as described above), and the opposite in the tensile member 10 is secured to a button (e.g., button 1600 as shown in FIG. 62).

The apparatus and methods described above herein may further be used for various methods for augmenting or replacing natural ligaments. Some examples of ligament augmentations are described with reference to FIGS. 103-110. These augmentations have in common the use of one or more tensile members 10 as described above having a first end anchored to a first bone, passing through a first passage in the first bone, spanning the gap to a second bone, spanning a second passage in the second bone, and having a second end anchored to the second bone.

In making these augmentations, the tensile members 10 may be implanted, tensioned, and anchored using any of the apparatus and methods described above. In some of the exemplary augmentations, a single tensile member 10 is used. This is referred to as a "single-strand" augmentation. It will be understood that a single strand of the tensile member may be made up of smaller individual fibers or sub-strands. In some of the exemplary augmentations, to tensile members 10 are used, where first ends of the two tensile members are anchored at a common first end point, and the two tensile members 10 diverge such that their individual second ends are anchored at disparate endpoints. This is referred to as a "double-bundle" augmentation.

Figures 103A, 103B, 103C:
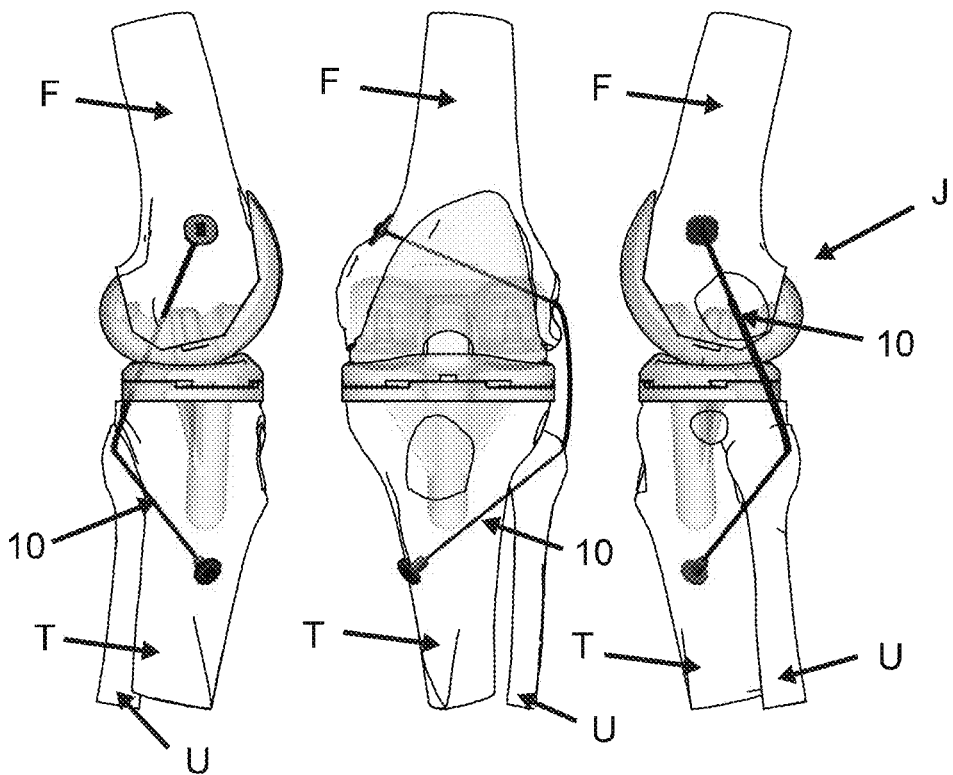
FIGS. 103A, 103B, and 103C are schematic views of the medial, anterior, and lateral aspects, respectively of a human knee joint, showing a single strand lateral cruciate ligament augmentation.

FIGS. 103A, 103B, and 103C show the human knee joint J having a single strand lateral cruciate ligament augmentation. A single tensile member 10 has a first end anchored in the tibia T, passes through the tibia T and the fibula U, spans the gap across the lateral aspect of the tibia T and femur F, passes through the femur F, and has its second end anchored in the femur F.

Figures 104A, 104B, 104C:
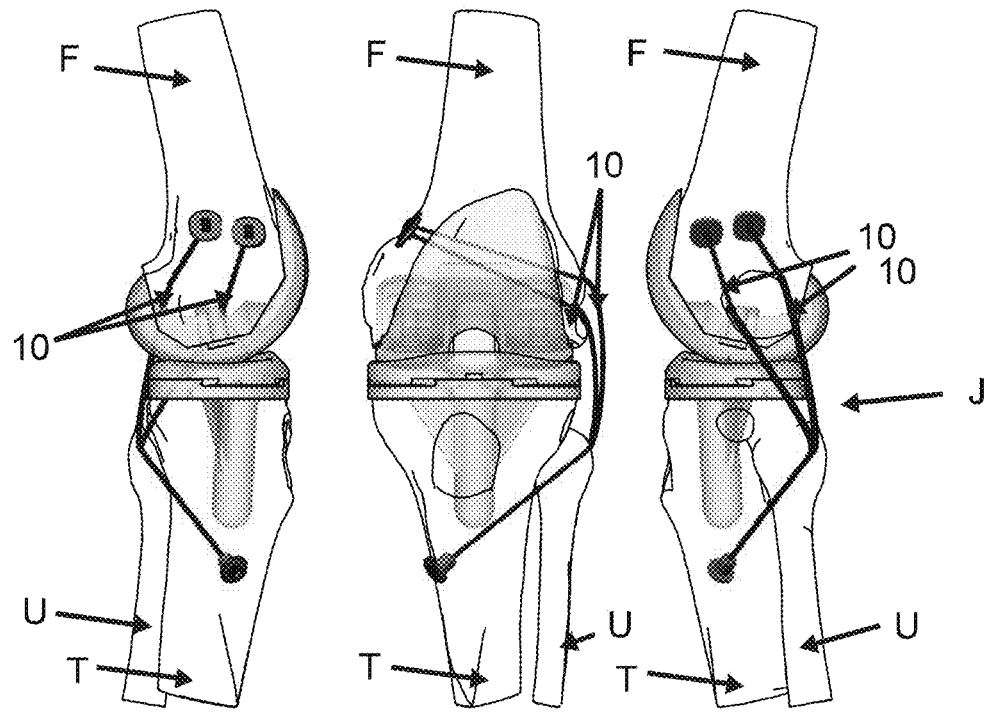
FIGS. 104A, 104B, and 104C are schematic views of the medial, anterior, and lateral aspects of a human knee joint, showing a double bundle lateral cruciate ligament augmentation.

FIGS. 104A, 104B, and 104C show the human knee joint J having a double bundle lateral cruciate ligament augmentation. A pair of tensile members 10 has their common first ends anchored in the tibia T, passes through the tibia T and the fibula U, diverge as they span the gap across the lateral aspect of the tibia T and femur F, pass through the femur F through two separate channels, and have their individual second ends anchored in the femur F.

Figures 105A, 105B, 105C:
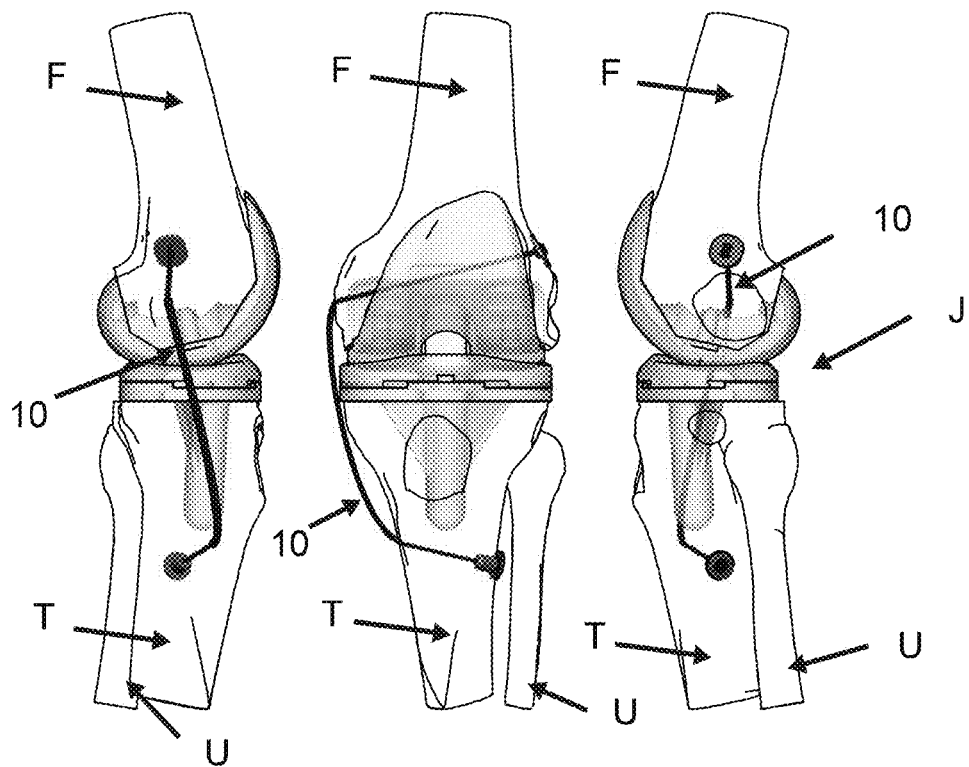
FIGS. 105A, 105B, and 105C are schematic views of the medial, interior, and lateral aspects, respectively, of a human knee joint, showing a single strand medial cruciate ligament augmentation.

FIGS. 105A, 105B, and 105C show the human knee joint J, having a single strand medial cruciate ligament augmentation. A single tensile member 10 has a first end anchored in the tibia T, passes through the tibia T, spans the gap across the medial aspect of the tibia T and femur F, passes through the femur F, and has its second end anchored in the femur F.

Figures 106A, 106B, 106C:
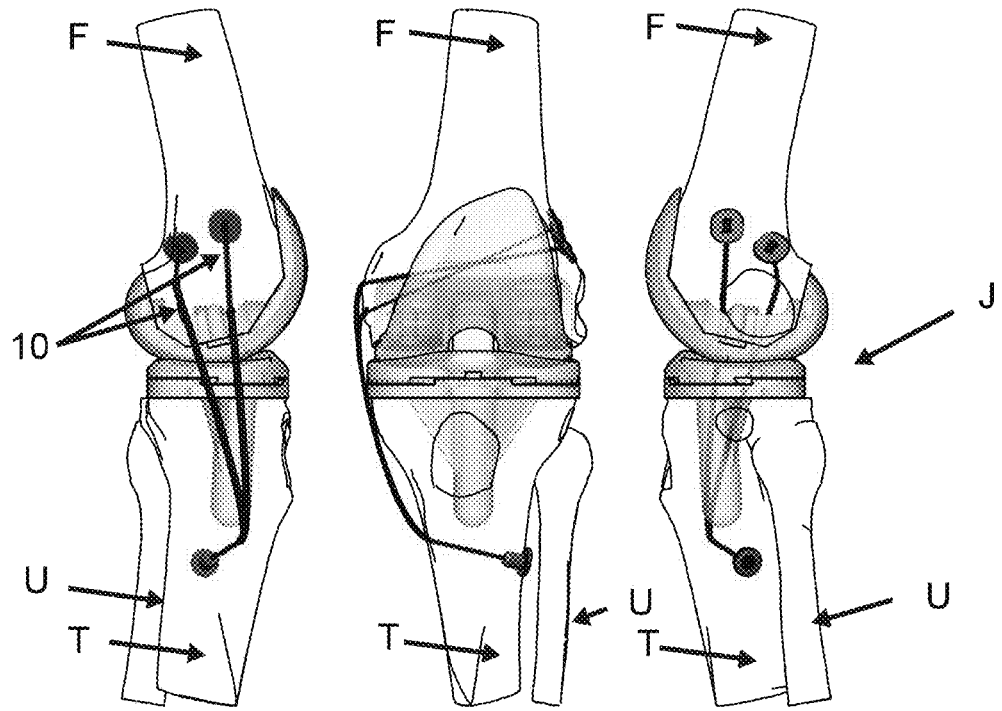
FIGS. 106A, 106B, and 106C are schematic views of the medial, anterior, and lateral aspects, respectively, of a human knee joint, showing a double bundle medial cruciate ligament augmentation.

FIGS. 106A, 106B, and 106C show a human knee joint J, having a double bundle medial cruciate ligament augmentation. A pair of tensile members 10 have their common first ends anchored in the tibia T, pass through the tibia T, diverge as they span the gap across the medial aspect of the tibia T and femur F, pass through the femur F through two separate channels, and have their individual second ends anchored in the femur F.

Figure 107A:
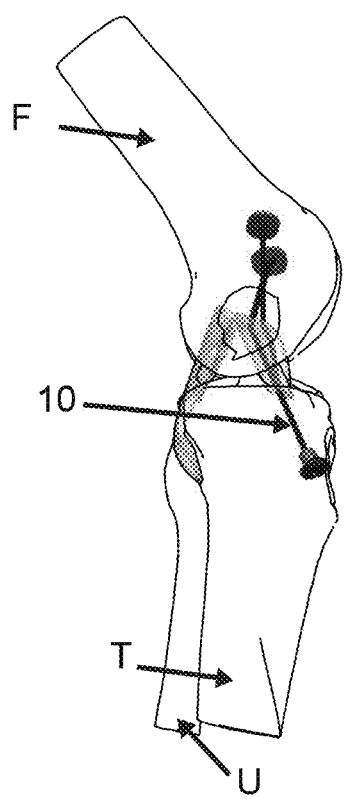
FIGS. 107A, 107B, and 107C are schematic views of the medial, anterior, and lateral aspects, respectively, of a human knee joint, showing a double bundle anterior cruciate ligament augmentation.
Figure 107B:
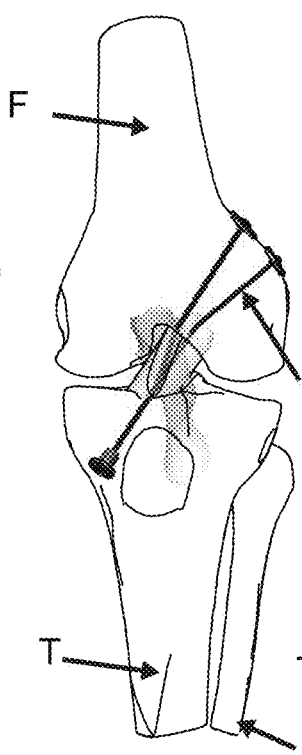
Figure 107C:
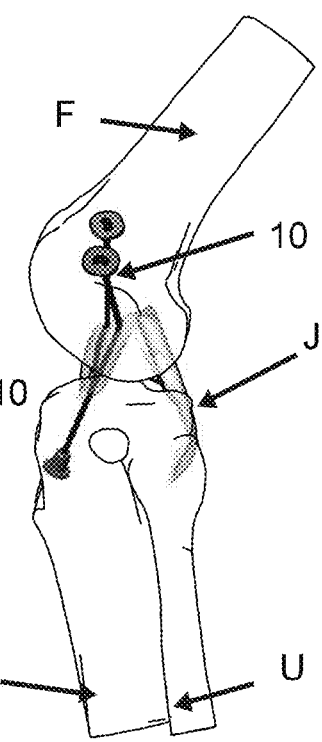

FIGS. 107A, 107B, and 107C show a human knee joint, having a double bundle anterior cruciate ligament augmentation. A pair of tensile members 10 have their common first ends anchored in the tibia T, pass through the tibia T, diverge as they span the gap between the tibia T and femur F, pass through the femur F through two separate channels, and have their individual second ends anchored in the femur F.

Figure 108A:
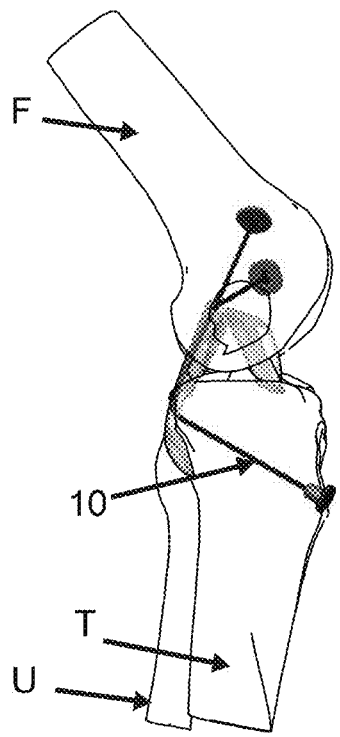
FIGS. 108A, 108B, and 108C are schematic views of the medial, anterior, and lateral aspects, respectively, of a human knee joint, showing a double bundle posterior cruciate ligament augmentation.
Figure 108B:
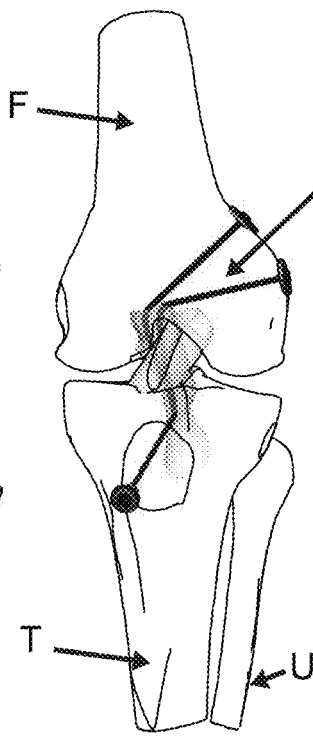
Figure 108C:
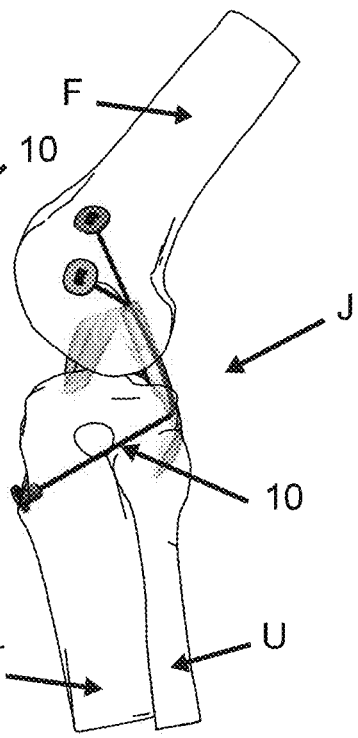

FIGS. 108A, 108B, and 108C show a human knee joint, having a double bundle posterior cruciate ligament augmentation. A pair of tensile members 10 have their common first ends anchored in the tibia T, pass through the tibia T, diverge as they span the gap between the tibia T and femur F, pass through the femur F through two separate channels, and have their individual second ends anchored in the femur F.

FIGS. 109A and 109B show a human foot having a double bundle ligament augmentation. A pair of tensile members 10 have their common first ends anchored in the tibia T, pass through the tibia T, diverge as they exit the tibia and wrap around the calcaneus C, pass through the calcaneus C through two separate channels, and have their individual second ends anchored in the calcaneus C.

Figure 110A:
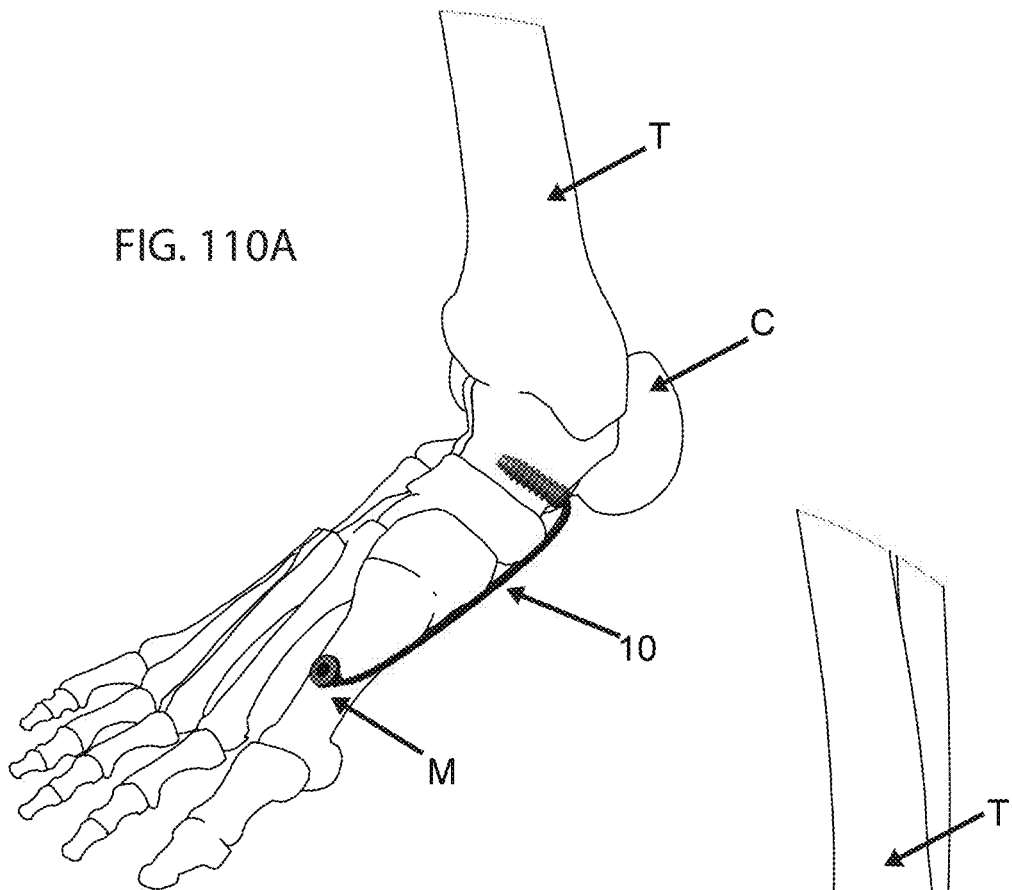
FIGS. 110A and 110B are schematic views of the lateral aspect of the human foot, showing a single strand forefoot correction.
Figure 110B:
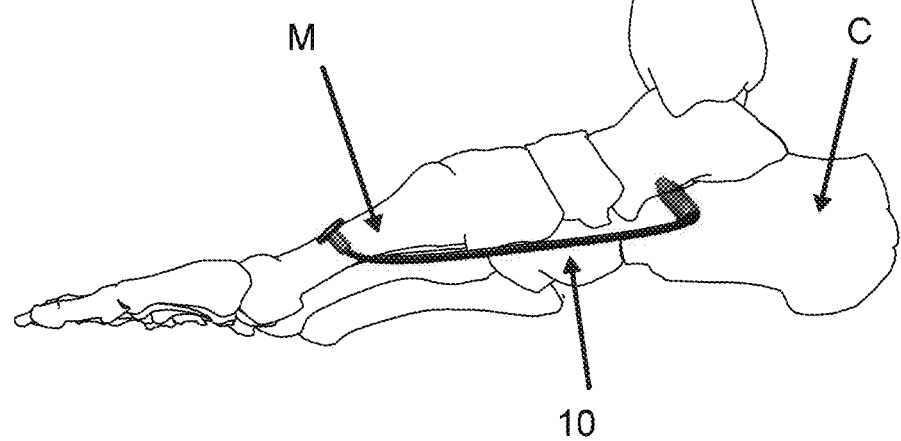

FIGS. 110A and 110B show a human foot having a double bundle ligament augmentation. A single tensile member 10 has its first end anchored in the calcaneus C, spans the gap between the calcaneus and one of the metatarsals M, passes through the metatarsal M, and has its second end anchored in the metatarsal M.

Figure 111A:
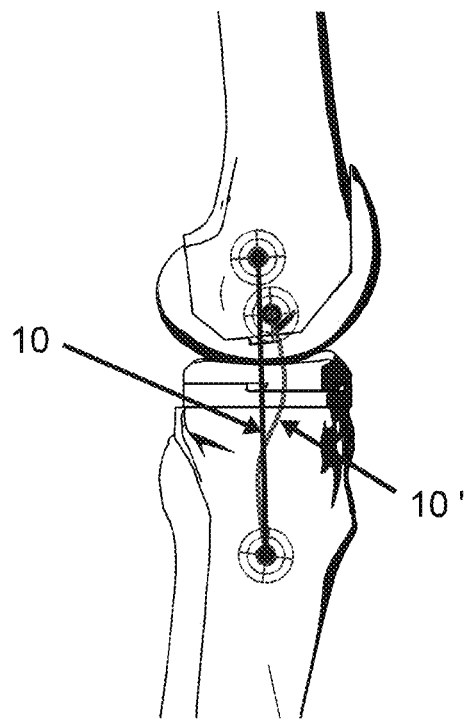
FIGS. 111A and 111B are schematic views of the medial aspect of the human knee joint, in extension and flexion, respectively, and having a double-bundle ligament augmentation.
Figure 112A:
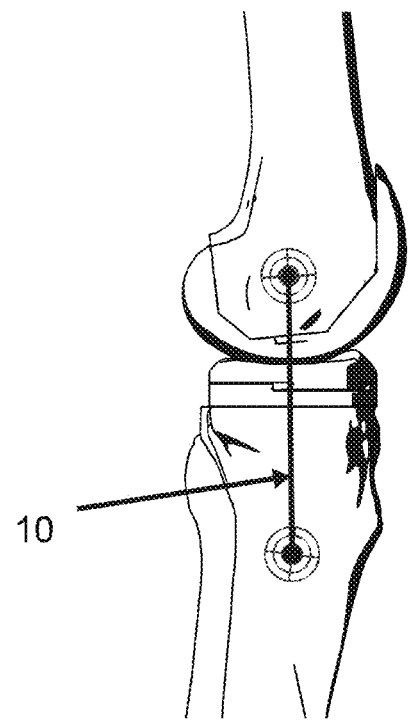
FIGS. 112A and 112B are schematic views of the medial aspect of the human knee joint, an extension and flexion, respectively and having a single-strand ligament augmentation.
Figure 111B:
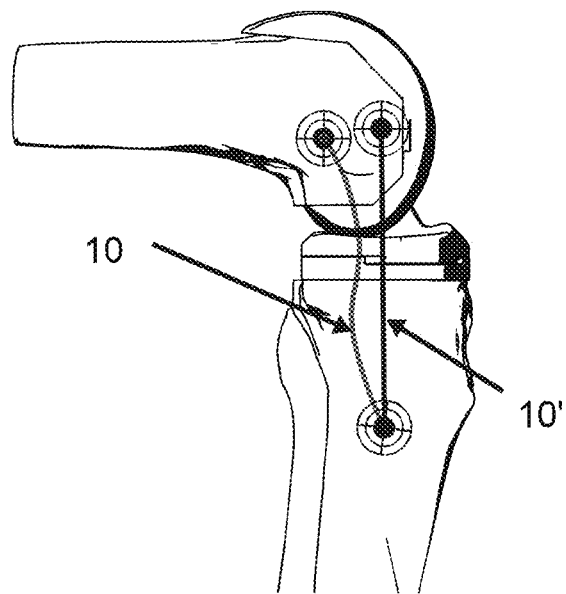
Figure 112B:
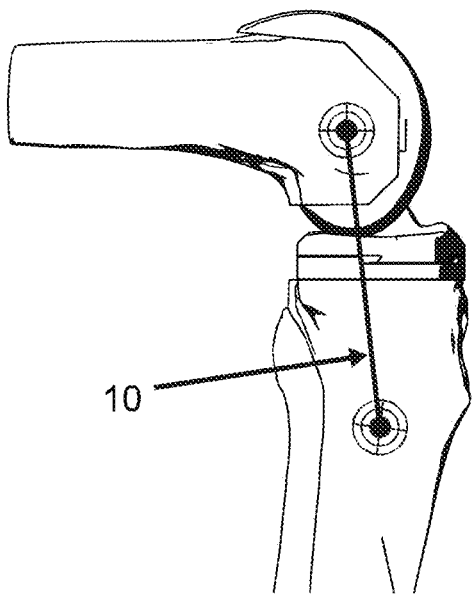

For any of the ligament augmentations described above, and especially for the augmentations of the ligaments of the knee, it is desirable to correctly clock the insertion and origin of the suture passage to replicate the native stability of healthy knee ligament. For example, FIGS. 111A and 111B are schematic views of the medial aspect of the human knee joint, in extension and flexion, respectively, and having a double-bundle ligament augmentation including first and second tensile members 10, 10'. It can be seen that the first tensile member 10 is under tension when the joint J is an extension, and the second tensile member 10 prime is under tension when the joint is in flexion. As another example, FIGS. 112A and 112B are schematic views of the medial aspect of the human knee joint, in extension and flexion, respectively and having a single-strand ligament augmentation. It can be seen that the single tensile member 10 is under appropriate tension in both extension and flexion.

Figure 113:
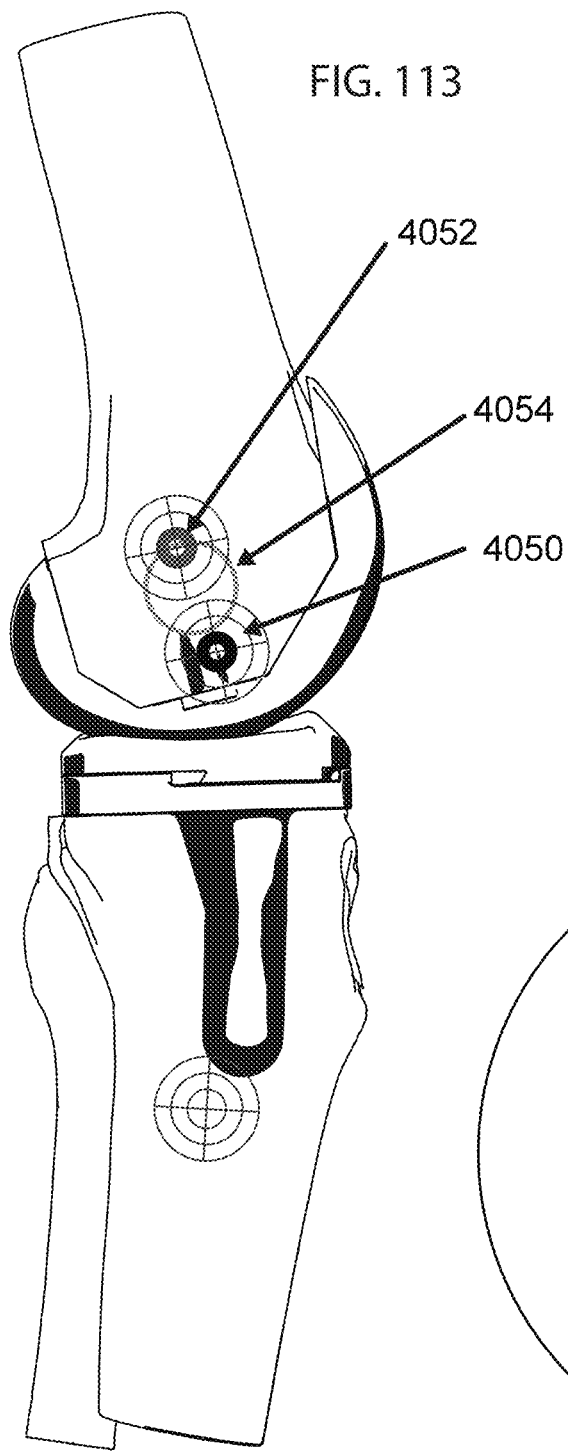
FIGS. 113 and 114 are schematic side views of the medial aspect of a human knee joint showing targets for ligament augmentation drill locations superimposed thereupon.
Figure 114:
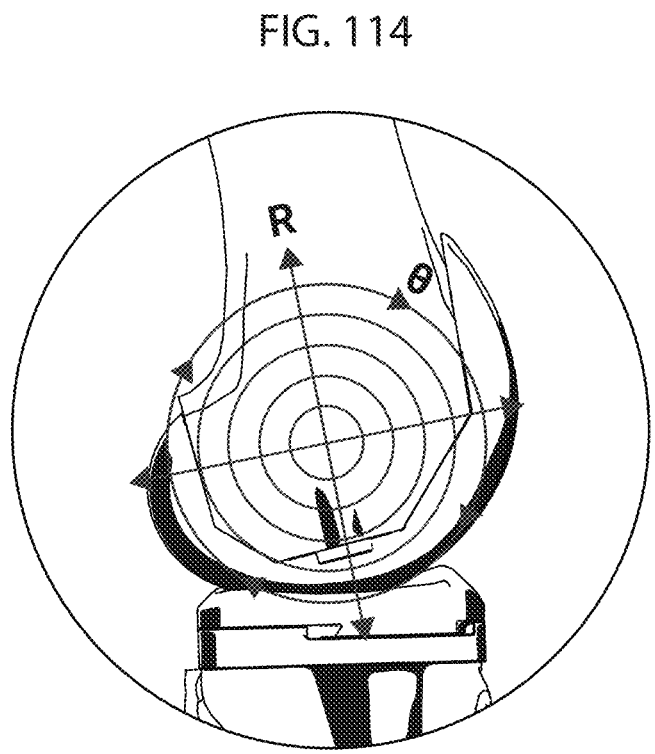

In order to determine accurate locations for drilling the bone passages to obtain the relationships described above, targets may be established on the epicondyle of the femur F or other bone structure. As shown in FIGS. 113 and 114, there would be a target 4050 for flexion augmentation and a target 4052 for an extension augmentation, both referenced relative to a landmark circle 4054. Location of the targets may be expressed in Cartesian coordinates or in polar coordinates (R, THETA) as shown in FIG. 114.

Figure 115:
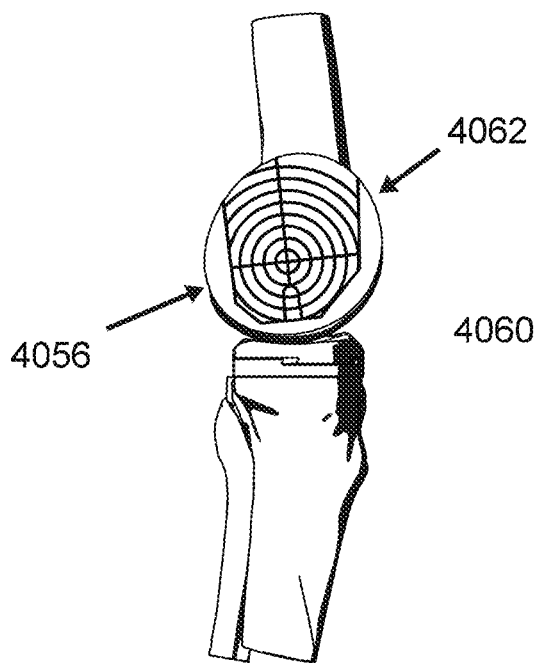
FIGS. 115-117 are schematic views of a human knee joint showing a drill guide attached thereto.
Figure 116:
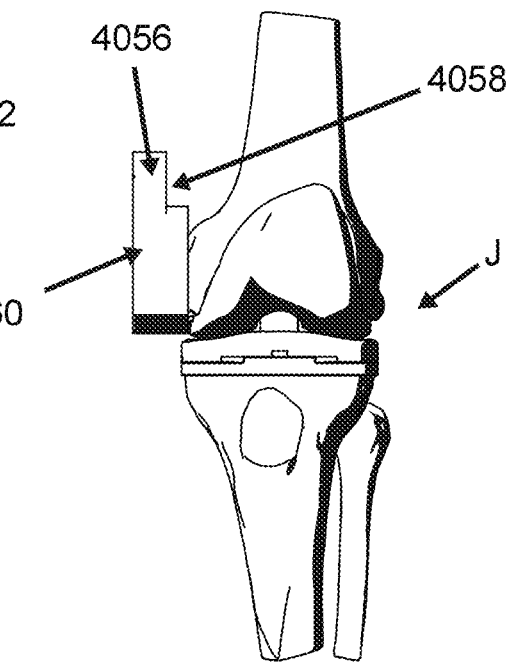
Figure 117:
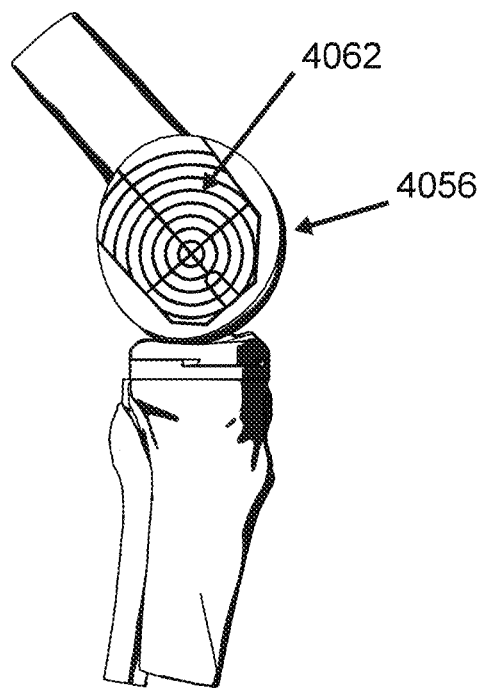
Figures 124, 125:
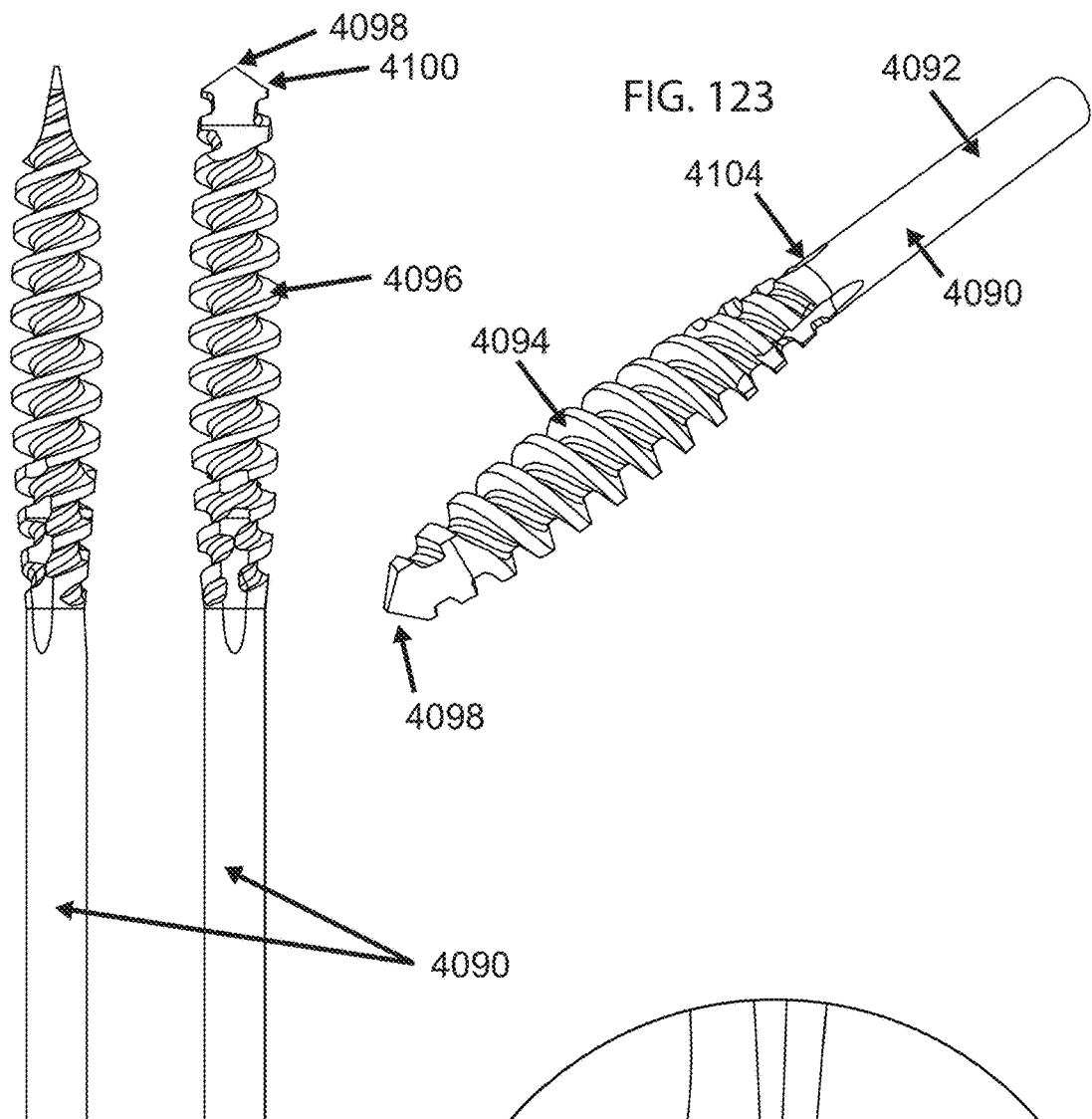
FIG. 124 is a front elevation view of the self-tracking reamer of FIG. 122.
FIG. 125 is a side elevation view of the self-tracking reamer of FIG. 122.
Figure 126:
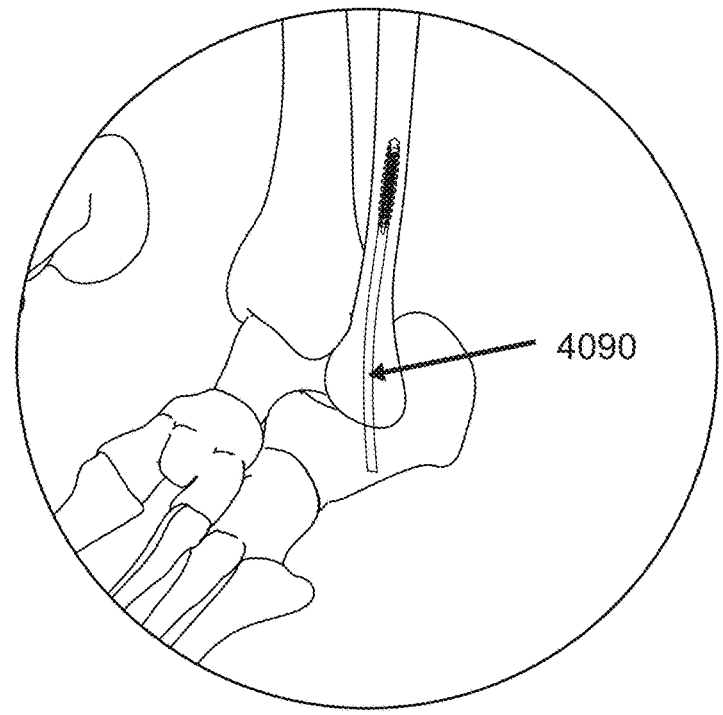
FIG. 126 is a schematic perspective view of the self-tracking of FIG. 122 being used to ream out the canal of a bone.

The location of the targets may be established and transferred to the epicondyle or other bone by use of a drill guide 4056 as seen in FIGS. 115-117. The drill guide 4056 is a solid body having a backside 4058 generally conformable to the epicondyle and a front side 4060 provided with appropriate gradations 4062 such as a Cartesian coordinate grid or polar coordinate grid. The drill guide 4056 is configured to rotate with the movement of the knee joint J through various positions from full flexion to full extension and provides an accurate visual reference of a drill target. The drill guide 4056 may be made of a freely-machine able material such as a biocompatible polymer, allowing the surgeon to drill through the drill guide 4056 into the bone.

Another type of repair that may be accommodated using the method and apparatus described herein as a "cerclage" in which a tensile member 10 is wrapped around a bone and then placed under tension to form a closed-loop structure.

FIGS. 118 and 119 illustrate an exemplary clamp 4060 that may be used to receive and anchor distal ends of a tensile member 10. The clamp 4060 has a body 4062 with open ends. Semi-cylindrical outer compression members 4064 are disposed inside the body 4062, flanking an inner compression member 4066. The inner and outer compression members 4066 and 4064 are mutually shaped to define two generally cylindrical channels, each of which receives an end of a tensile member 10. The inner compression member 4066 has a central slot 4068 which can receive a locking wedge 4070. In use, the ends of the tensile member 10 would be placed into the channels, the tensile member tensioned as described elsewhere herein, and then the locking wedge 4070 driven in to swaging compress the compression members 4064, 4066, thus anchoring the tensile member 10 and maintaining the desired tension.

FIGS. 120 and 121 illustrate another exemplary clamp 4080 which may be used to receive an anchor distal ends of one or more tensile members 10. The clamp 4080 includes a housing 4082, a collet 4084, and a sleeve 4086. The characteristics and configuration of the elements of the clamp 4080 may be substantially identical to corresponding elements of the anchor 3012 described above, and the clamp 4080 may be configured as a "breakaway" or "snap-off" device as described elsewhere herein. The clamp 4080 may include a channel 4088 in the housing 4082 to allow tensile member 10 to lie flat against it. The clamp 4080 may be implanted using any of the insertion instruments described herein.

FIG. 122 shows a cerclage applied to a human femur F using the clamp 4080 of FIGS. 120 and 121 in combination with a tensile member 10. The tensile member 10 is wrapped around the femur F or other bone, and is distal ends inserted through the clamp 4080. The methods described above are used to tension the tensile member and to force the sleeve 4086 down over the collet 4084 causing it to swage down onto and anchor the tensile member 10.

In the process of performing any of the repairs and/or augmentations described herein, there is sometimes a need to ream out a passage in the existing canal of a human bone. During such reaming process, it is desirable to follow the past of least resistance and to cut away only soft bone, leaving the exterior wall undisturbed.

FIGS. 123-126 illustrate a self-tracking reamer 4090 suitable for this purpose. The reamer 4090 includes a shaft 4092 and a head 4094. The shaft 4092 is suitably sized and shaped to be received in a manual or power drill or similar device. The head 4094 includes spiral flutes 4096 terminating at a cutting tip 4098 having suitable cutting surfaces 4100. The flutes 4096 may have a single or double lead. The shaft and head are made of a suitable material such as a stainless steel alloy and have dimensions selected so as to provide some flexibility in bending. The head 4094 is configured have a greater diameter in its central portion 4102 that at either its proximate end 4104 or the cutting tip 4098. The overall shape may be described as a "cobra head" shape.

In use, the reamer 4090 is effective to pull itself into and through the bone canal. Because of the increased diameter at the central portion 4102, and the shape of the cutting tip 4098 which principally cuts along the centerline, the reamer 4090 is able to bend and follow the path of least resistance, cutting only soft bone and not the outer wall. Once the reamer 4090 is driven to a desired distance, it can be driven backwards (e.g. counter-clockwise) to remove from the bone, or be pulled backwards with some force while driving clockwise to fully clear the bone canal.

Figure 130:
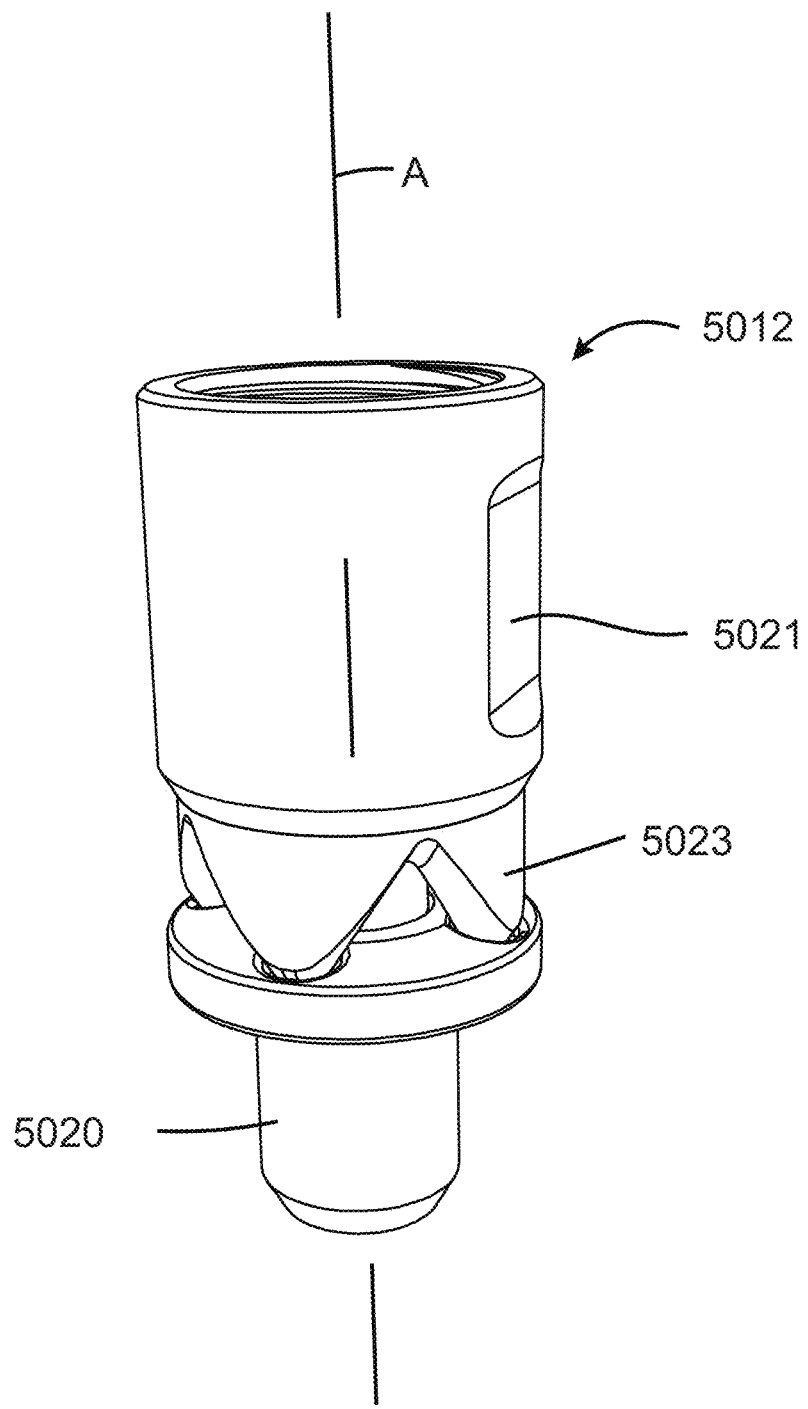
FIG. 130 is a perspective view of an exemplary embodiment of an anchor for use with a tensile member.
Figure 131:
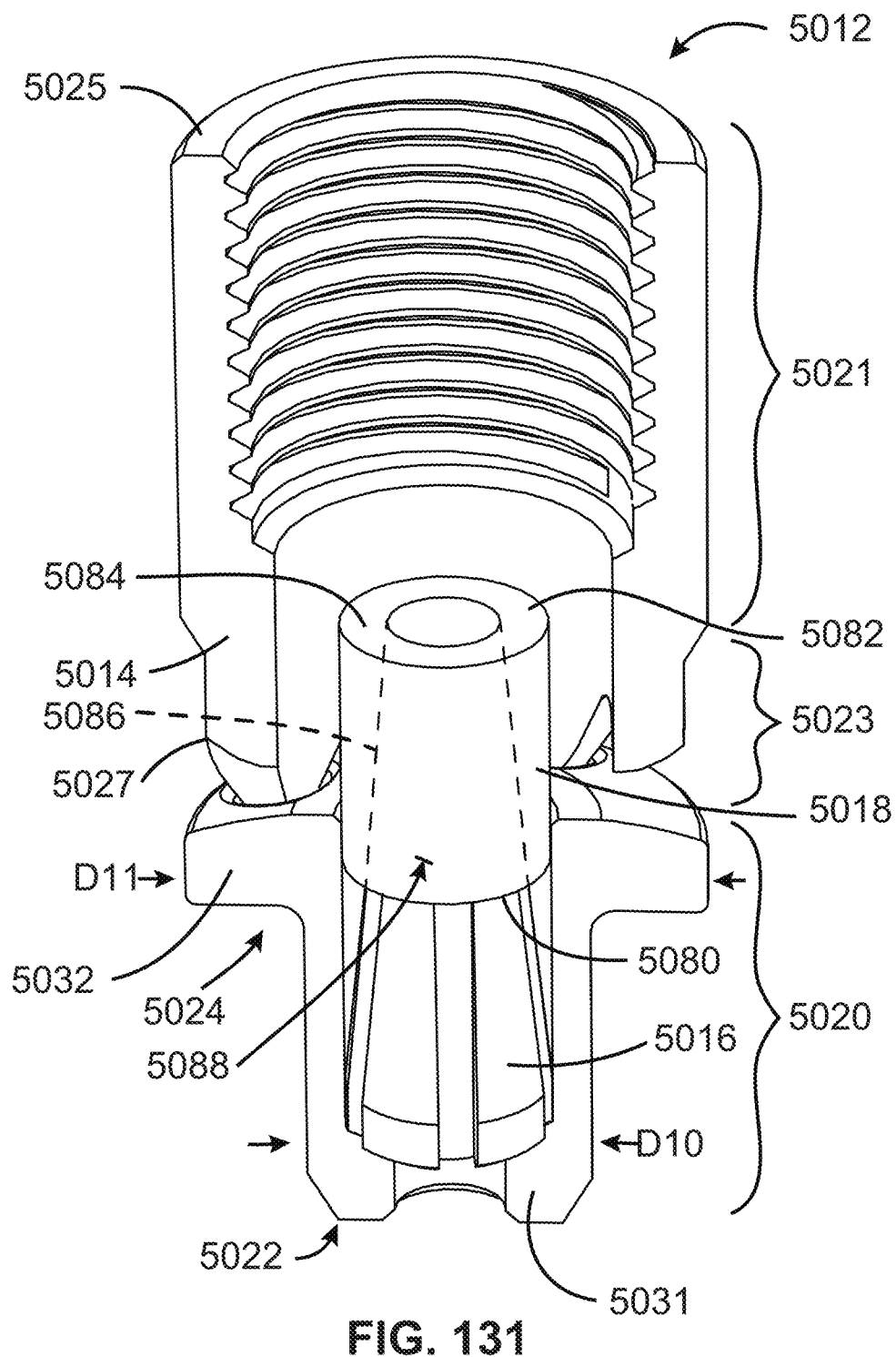
FIG. 131 is a partially cutaway perspective view of the anchor of FIG. 130.

FIGS. 130 and 131 illustrate another exemplary embodiment of an anchor 5012. The anchor 5012 includes three functional elements, namely a housing 5014 configured to be implanted into bone, a collet 5016 received in the housing 5014 and configured to be swaged around and against a tensile member 10 (FIG. 1) without moving axially relative to the housing 5014 or tensile member 10, and a sleeve 5018 received in the housing 5014 which is capable of moving axially within the housing 5014 so as to swage the collet 5016, thus retaining the tensile member 10. (Some minimal axial movement of the collet 5016 not significantly affecting tension may occur during swaging).

The housing 5014 has a body portion 5020 extending along a central axis "A" between first and second ends 5022, 5024. The body portion 5020 is defined by a peripheral wall having opposed interior and exterior surfaces, and defining a hollow interior. In the illustrated example, the body portion 5020 is generally cylindrical in shape. The first end 5022 has an internal flange 5031 which is sized to define a stop against axial motion of the collet 5016.

A generally annular flange 5032 is located at or near the second end 5024 and extends radially outwards from the body portion 5020. The anchor 5012 may have an overall size which is generally small enough to be implanted inside a human body. In one example the housing 5014 may be cylindrical in shape with an outside diameter "D10" of about 3 to 12 mm, and the flange 5032 may have an outside diameter "D11" about 5 to 20 mm.

Figure 132:
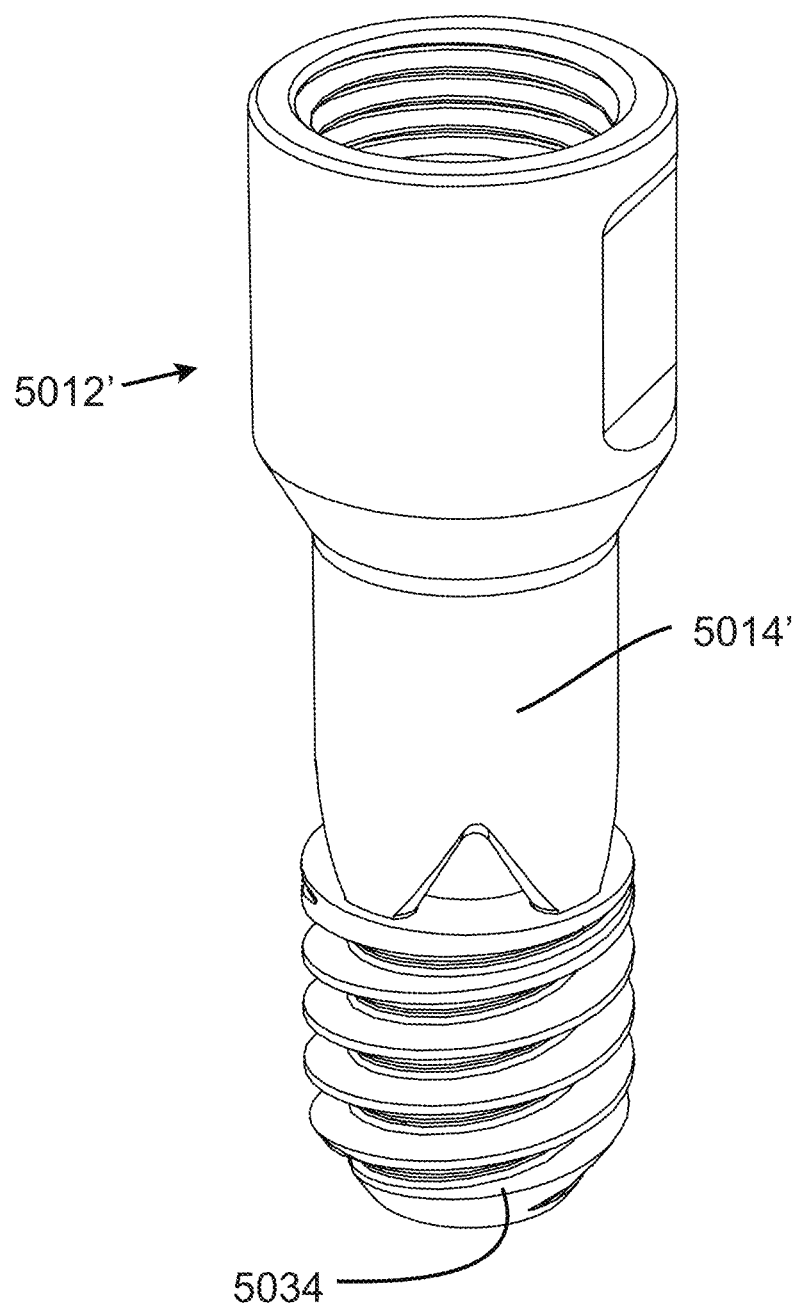
FIG. 132 is a perspective view of a variation of the anchor shown in FIG. 130.

Other means may be provided in order to permit the anchor 5012 to be implanted in various orientations. For example, FIG. 132 illustrates an alternative anchor 5012' having a housing 5014' which lacks a flange as depicted in other embodiments. An exterior surface of the body of the housing 5014' is formed into male threads 5034'. Stated another way, a maximum diameter of the housing 5014' is defined by an outer extent of the threads 5034. The lack of a flange extending beyond the outer extent of the threads 5034' permits the housing 5014' to be implanted flush or sub-flush relative to the bone surface. More importantly, it permits it to be installed in a bore or passage which is oriented at any arbitrary angle relative to the surface of the bone. In such situations, if a flange were used, a gap would be present between at least some portions of the flange and the bone. Stated another way, the bore or passage in the bone can extend along an axis which is oblique to the surface of the bone.

Referring back to FIGS. 130 and 131, the housing 5014 includes an extension portion 5021 extending away from the second end 5024 of the body portion 5020. The extension portion 5021 is coupled to the body portion 5020 by a breakaway structure 5023. As manufactured and prior to use, the entire housing 5014 forms a single unitary, integral, or monolithic structure including the body portion 5020, extension portion 5021, and breakaway structure 5023 that provides a "breakaway" or "snap-off" connection between the body portion 5020 and the extension portion 5021.

The extension portion 5021 extends between a first end 5025 and a second end 5027. The second end 5027 is interconnected to the breakaway structure 5023. The first end 5025 may be provided with a mechanical connector for being connected to an insertion instrument which is described in more detail below. In the illustrated example, the first end 5025 is provided with a connector 5029 in the form of screw threads. As described in more detail below, this permits a secure, releasable connection to an instrument used for insertion or manipulation of the anchor 5012.

The breakaway structure 5023 is configured in terms of its shape, dimensions, and material properties such that it will retain its structural integrity and interconnected the body portion 5020 and the extension portion 5021 when subjected to tensile loads up to a first magnitude sufficient to complete a swaging process of the anchor 5012 as described below. This is referred to herein as a "first predetermined tensile load". The breakaway structure 5023 is further configured in terms of its shape, dimensions, and material properties such that it will fail and permit separation of the body portion 5020 and the extension portion 5021 when subjected to tensile loads equal to or greater than a second magnitude, referred to herein as a "second predetermined tensile load". The second tensile load is greater than the first tensile load. The second tensile load may be selected to be sufficiently greater than the first predetermined tensile load such that failure of the breakaway structure 5023 is unlikely to occur during the swaging process. Stated another way, the second predetermined tensile load may have a safety margin over the first predetermined tensile load. In one example, the second predetermined tensile load may be selected to be at least 50% to 100% greater than the first predetermined tensile load.

In general, the breakaway structure 5023 may include one or more stress-concentrating columns which present a known cross-sectional area, thus permitting reliable computation of the tensile stresses in the breakaway structure 5023 for a given applied load.

Figure 133:
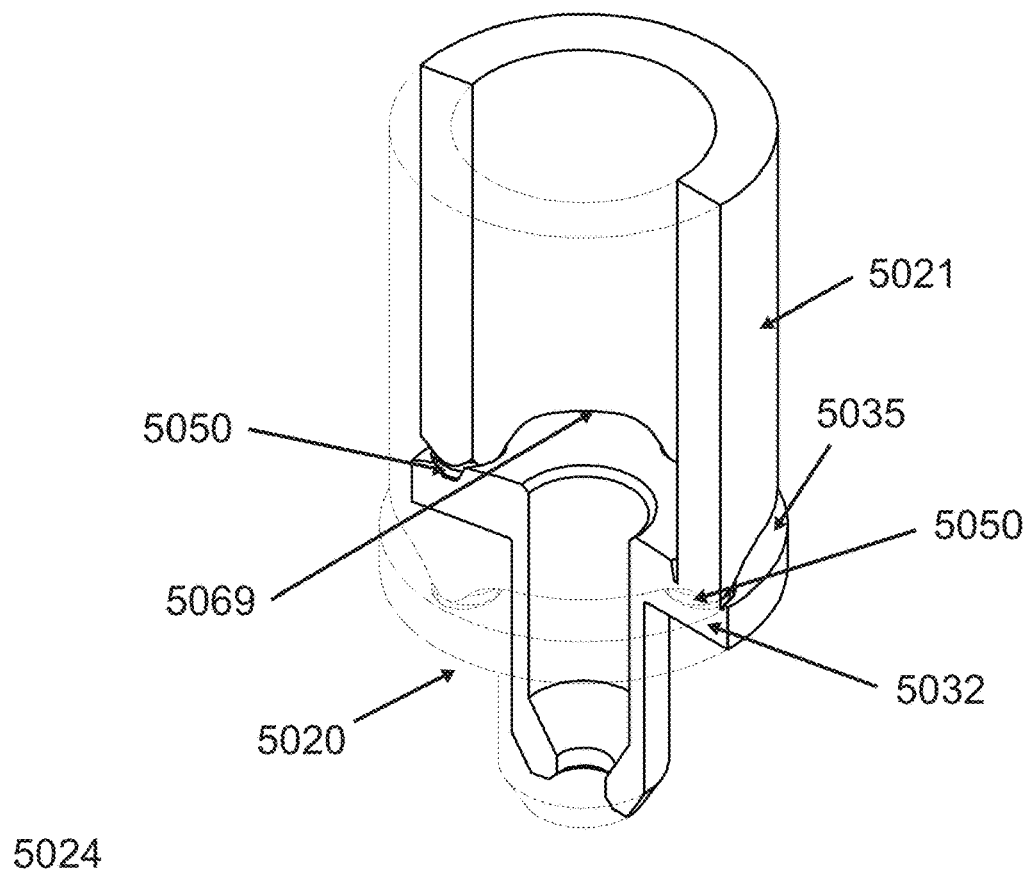
Figure 134:
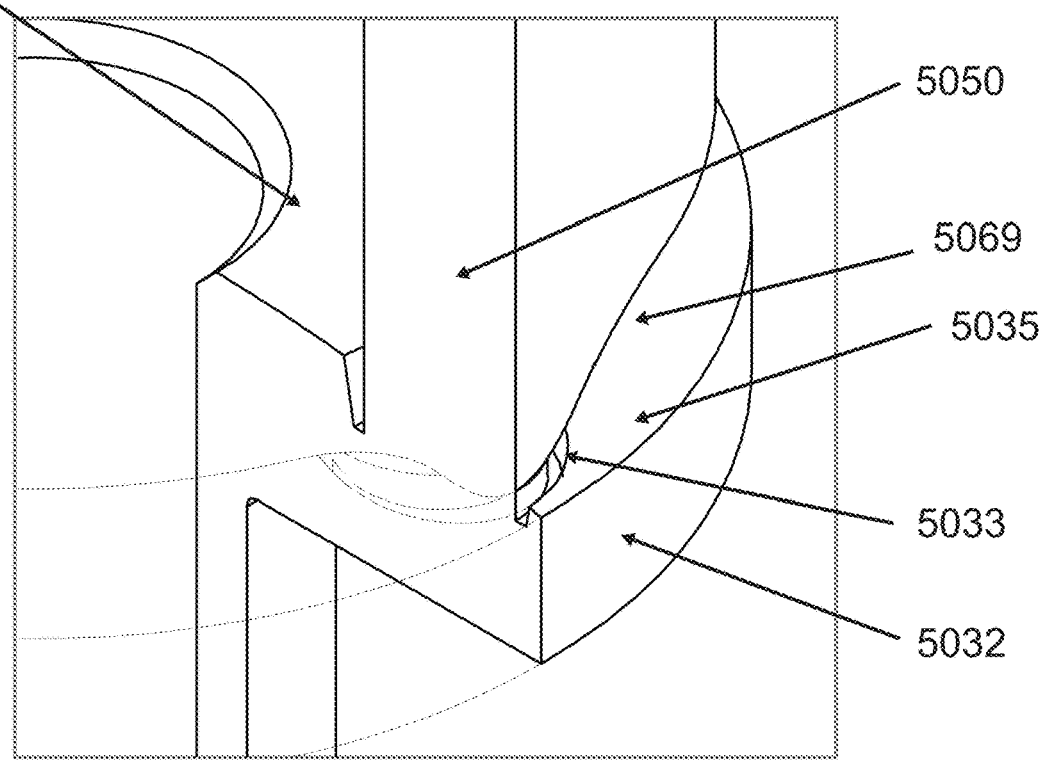
Figure 139:
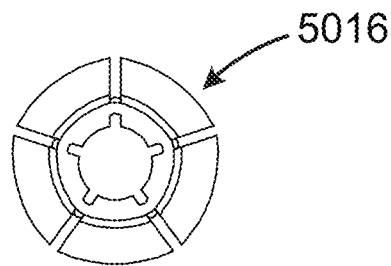
Figure 140:
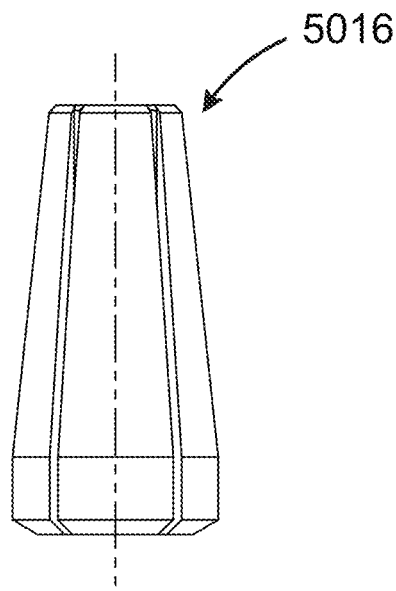
Figure 142:
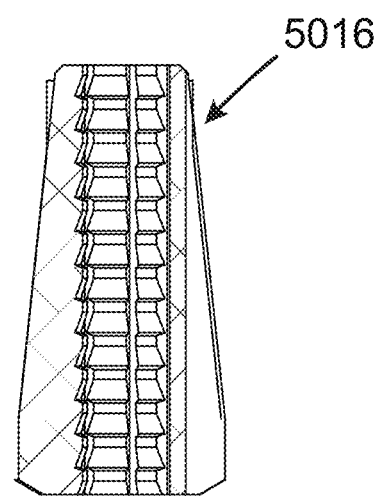
Figure 141:
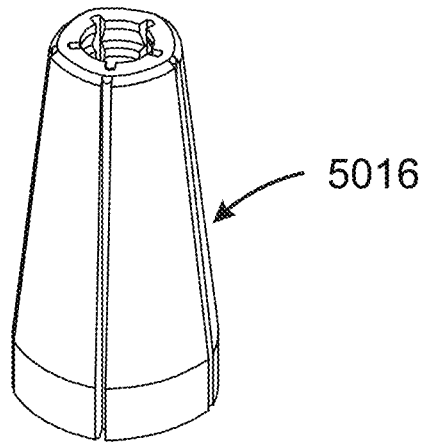
Figure 143:
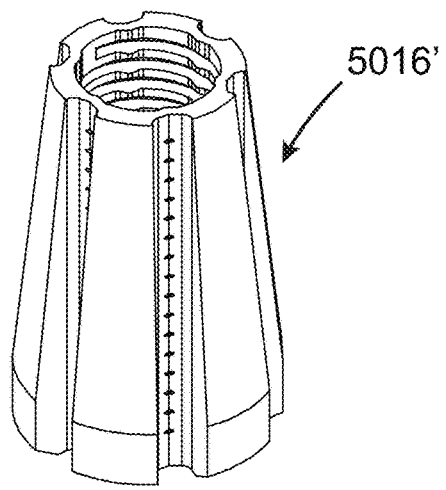
Figure 144:
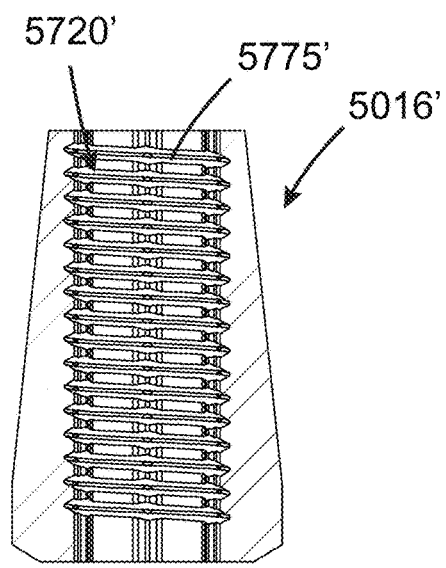

In the illustrated example, best seen in FIGS. 133 and 134, the breakaway structure 5023 includes a plurality of stress-concentrating columns 5050 arrayed around the periphery of the flange 5032, which have a circular cross-sectional shape adjacent to and/or or at the flange 5032. The stress-concentrating columns 5050 are separated by openings 5069. It will be understood that other column cross-sectional shapes providing a predictable cross-sectional area may be used, and that the cross-sectional shape may vary over the length of the column.

Optionally, the stress-concentrating columns 5050 may intersect the flange 5032 at the bottom of recesses 5033 formed in the flange 5032. In use, this permits the stress-concentrating columns 5050 to separate along the fracture plane which is "below" a top surface 5035, or stated another way it is sub-flush to, or recessed from, the top surface 5035.

The collet 5016 (FIGS. 135-138) is a hollow member with first and second ends 5064, 5068 and defined by a sidewall 5718 having an exterior surface 5070. The collet 5016 has a central bore 5720 which is sized to receive the tensile member 10 described above. For example, the central bore 5720 may be cylindrical, with a minimum inside diameter or characteristic dimension "D12" which is initially slightly larger than a diameter D1 of the tensile member 10. The central bore 5720 need not have a circular cross-section; the cross-section may be a polygon shape (e.g. triangular, square) or it may be a lobed shape (e.g., triangular with radiused corners).

The collet 5016 is configured so as to readily permit it to be swaged, i.e. shaped in such a manner to reduce its cross-section and the size of the central bore 5072 so that it firmly engages the tensile member 10 and allows a tensile force to be applied thereto. The act of swaging may involve the collet 5016 being deformed, crushed, collapsed, or compressed. The collet 5016 is configured, e.g., sized and shaped, such that when subjected to pressure from the sleeve 5018, it will abut the internal flange 5031 of the body 5020, thus stopping its further axial movement, and permitting the swaging action to take place without axial movement of the collet 5016 relative to the tensile member 10 or housing 5014.

The exterior surface 5070 has a shape adapted to interact with the interior surface of the sleeve 5018 described below so as to produce a radially inwardly directed force on the collet 5016 in response to the axial movement of the sleeve 5018. Fundamentally, at least one of the exterior surface 5070 of the collet 5016 and the interior surface of the sleeve 5018 incorporates a taper i.e., a diameter or lateral dimension which is larger near one end and smaller near the opposite end of the respective element. In the example shown in FIGS. 135-138, the exterior surface 5070 has a cylindrical section 5071 and a generally frustoconical section 5073. The exterior dimensions and shape of the exterior surface 5070 are selected so as to provide a predetermined fit with the sleeve 5018 both before and after a compression process.

In this embodiment, the collet 5016 incorporates a geometry having sections of removed material or "negative space" which are configured to facilitate collapse of the collet 5016. An array of longitudinal grooves 5722 are formed in the outer surface 5070 of the sidewall 5718. Each of the grooves 5722 defines a thin neck 5724 or web (see FIG. 135). The grooves 5722 may have square internal corners as depicted. The longitudinal grooves may incorporate some curve or spiral.

FIGS. 139-142 show the collet 5016 after swaging. Post-swaging, the grooves 5722 may be collapsed. When swaged as described herein, the sidewall 5718 tends to collapse in a manner such that the neck or web 5724 folds into a U-shape.

Figure 147:
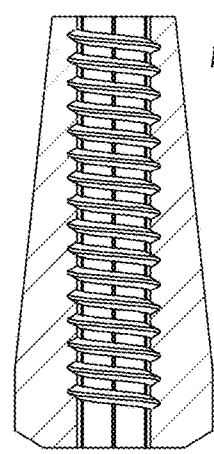
Figure 145:
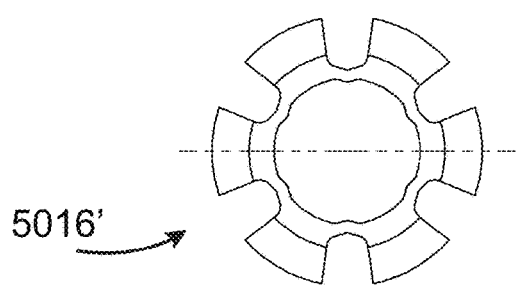
Figure 146:
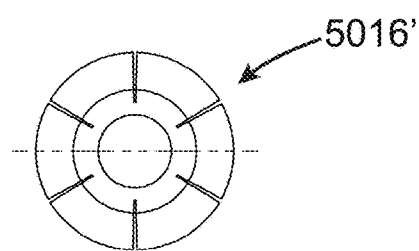

The central bore 5720 may include a surface texture which serves to enhance grip on a tensile member 10. Nonlimiting examples of surface texture structures include teeth, ribs, grooves, dimples, recesses, bumps, pins, ridges, knurling, checkering, and threads. In the example shown in FIGS. 135-138 this takes the form of longitudinal rows of ramped-shaped teeth 5775. FIGS. 143-146 illustrate an alternative collet 5016' which has a central bore 5720' with internal threads 5775' that serve the same purpose. This collet 5016' is shown in the pre-use condition in FIGS. 143-145 and in a swaged condition in FIGS. 146 and 147.

The sleeve 5018 (FIG. 131) is a hollow member with open first and second ends 5080, 5082. The sleeve 5018 is sized is such that the tensile member 10 described above can pass through the first and second ends 5080, 5082. The sleeve 5018 is defined by a peripheral wall having interior and exterior surfaces 5086, 5088, respectively. In the illustrated example, the sleeve 5018 is generally cylindrical in shape.

The interior surface 5086 has a shape adapted to interact with the exterior surface 5070 of the collet 5016 described above so as to produce a radially inwardly directed force on the collet 5016 in response to the axial movement of the sleeve 5018. As noted above, at least one of the exterior surface 5070 of the collet 5016 and the interior surface 5086 of the sleeve 5018 incorporates a taper i.e., a diameter or lateral dimension which is larger near the first end and smaller near the second end of the respective element. In the example shown in FIG. 131, the interior surface 5086 is tapered, defining a shape like a frustum of a cone, with a larger diameter at the first end 5080.

The anchor 5012 and its components may be made from any material which is biocompatible and which will engage the other elements so as to transfer tensile force thereto. As used herein, the term "biocompatible" refers to a material which is not harmful to living tissue. Nonlimiting examples of suitable materials for the housing 14 include polymers and metal alloys. Nonlimiting example of suitable metal alloys include stainless steel alloys and titanium alloys. The anchor 5012 or its components may be fabricated by a technique such as machining, forging, casting, sintering, or additive manufacturing (e.g., "3D printing"). The anchor 5012 or its components may be treated with known coating such as titanium nitride, chrome plating, carbon thin films, and/or diamond-like carbon coatings.

Figures 148, 150:
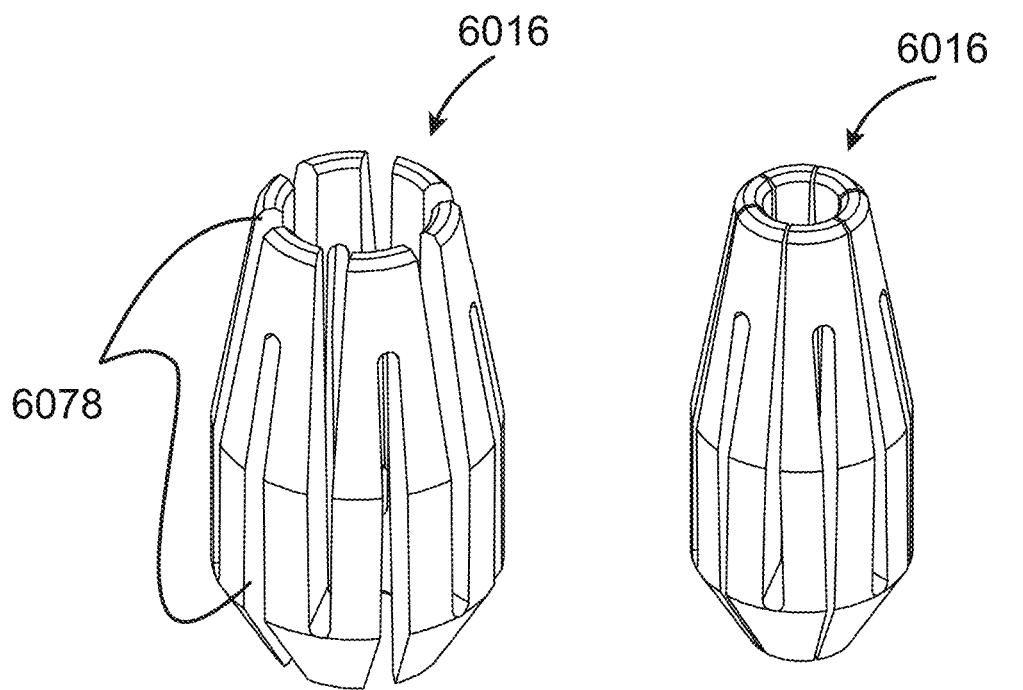
Figures 149, 151:
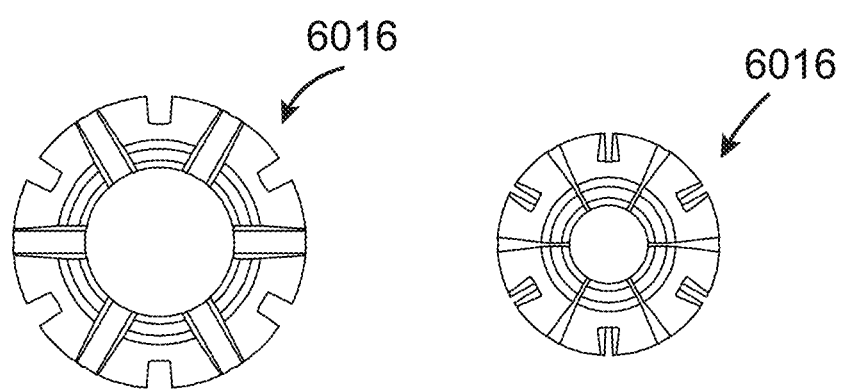

FIGS. 148-151 illustrate an alternative collet 6016 which may be substituted for collet 5016. Collet 6016 incorporates a geometry having sections of removed material or "negative space" which is configured to facilitate collapse of the collet 6016. In this example, the collet 6016 has a plurality of longitudinal through slots 6078 formed in the wall thereof, each slot 6078 being open to at least one end and extending less than the full length of the collet 6016. The through slots 6078 are arranged to define a spring-like structure. FIGS. 148 and 149 show the collet 6016 in a pre-use condition and FIGS. 150 and 151 show the collet 6016 in a swaged condition.

Figures 152, 153, 154:
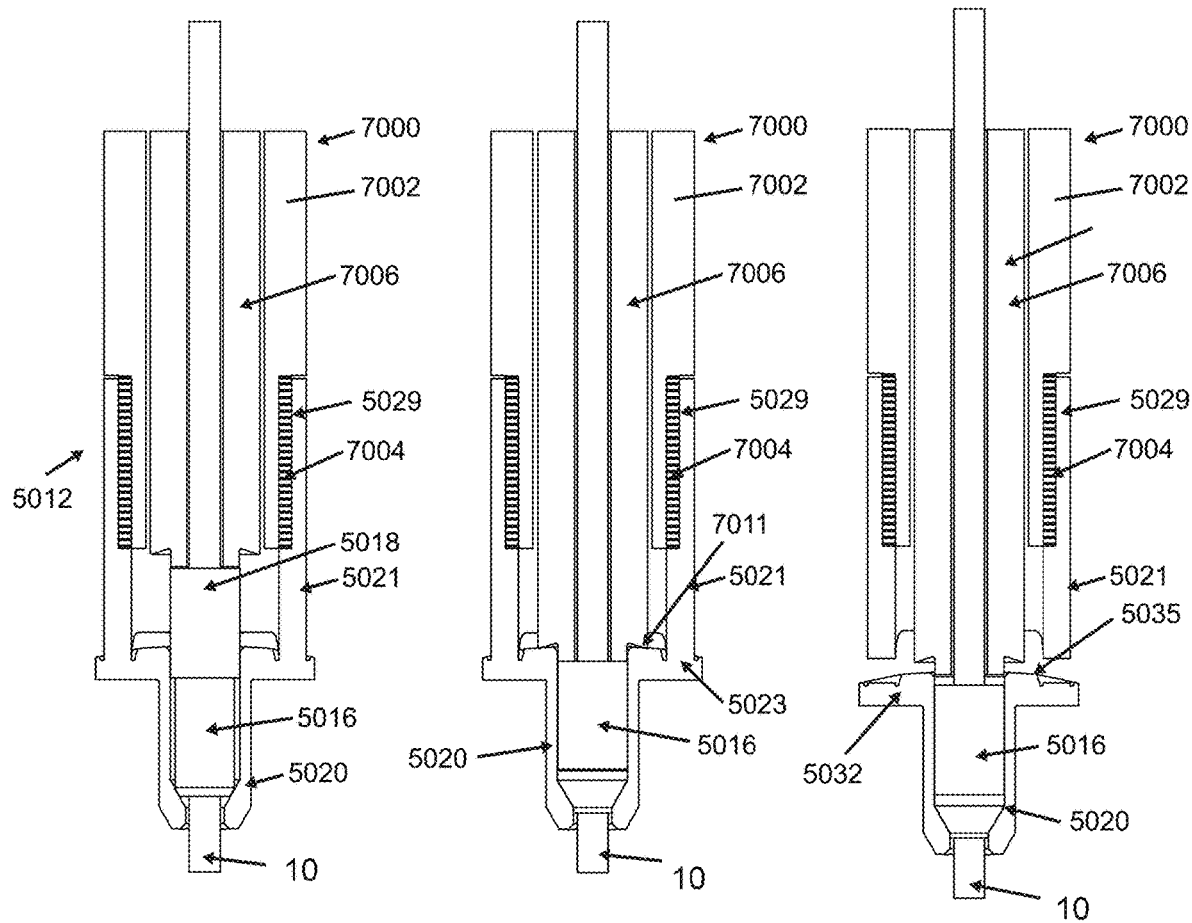

FIG. 152 illustrates an exemplary insertion instrument 7000 which may be used to insert, tension, and activate the anchors described above. The insertion instrument 7000 includes a stem 7002 having male threads 7004 formed on a distal end thereof, which engage threads 5029 of anchor housing 5014. A hollow pushrod 7006 extends through the stem 7002 and is slidably movable between retracted and extended positions. The pushrod 7006 is connected to a driving mechanism (not shown) for moving the pushrod 7006 between retracted and extended positions. This construction provides a highly rigid interconnection between the housing 5014 and the stem 7002 in order to maximize the surgeon's control and ability to manipulate the anchor 12. The hollow pushrod 7006 is mounted inside the stem and operates to swage the collet 5016 when desired.

The operation of the insertion instrument 7000 to implant anchor 5012 may be better understood with reference to FIGS. 152-154. As shown in FIG. 152, the anchor 5012 may be coupled to the instrument 7000 using their mutual connectors 7004, 5029. The pushrod 7006 initially rests against an end surface of the sleeve 5018 with essentially no load applied. A tensile member 10 passes through the collet 5016, the sleeve 5018, and the hollow pushrod 7006.

Prior to any swaging operation, the tensile member 10 may be tensioned. Once desired tension has been established, the instrument 7000 is actuated. More specifically, the pushrod 7006 extends outward. This applies a compressive load to the sleeve 5018, causing it to interact with the body portion 5020, collet 5016, or both in order to swage the collet 5016 around the tensile member 10, thus retaining the tensile member 10 in-place with the desired amount of tension. As the swage cycle is completed, a shoulder 7011 of the pushrod 7006 makes physical contact with the flange 5032 of the housing 5014 (FIG. 153).

It will be understood that the extension housing 5021 is mechanically coupled to the stem 7002 of the instrument 7000. Accordingly, extension of the pushrod 7006 results in a tensile load being applied to the breakaway structure 5023 described above. This load is transferred through some combination of force between the sleeve 5018 and/or physical contact between the shoulder 7011 and the flange 5032. As described above, the step of swaging is accomplished using a first predetermined tensile load.

Once the swaging procedure is completed, the pushrod 7006 is further actuated as shown in FIG. 154 to apply a tensile load sufficient to fracture the breakaway structure 5023 and separate the housing body portion 5020 from the extension portion 5021. This is accomplished using a second predetermined tensile force greater than the first predetermined tensile load. Once accomplished, the instrument 7000 with the housing extension portion 5021 still attached may be withdrawn, leaving the housing body portion 5020 in-place with the tensile member 10 secured with the desired amount of tension. Any remaining portion of the breakaway structure 5023 is below flush from the outer surface 5035 of the flange 5032. It thus does not protrude to irritate or injure the patient or the surgeon, and no additional trimming operation is required.

FIGS. 155-170 illustrate another exemplary clamp 6012 which may be used to receive and anchor distal ends of one or more tensile members 10 in order to apply a cerclage as described above. The clamp 6012 includes a housing 6014, a collet 6016, and a sleeve 6018. The characteristics and configuration of the elements of the clamp 6012, in particular the collet 6016 and sleeve 6018, may be substantially similar to corresponding elements of the anchor 5012 described above, and the clamp 6012 may be configured as a "breakaway" or "snap-off" device as described elsewhere herein. The clamp 6012 may be implanted using any of the insertion instruments described herein.

The housing 6014 includes an extension portion 6021 coupled to a body portion 6020 by a breakaway structure 6023. As manufactured and prior to use, the entire housing 6014 forms a single unitary, integral, or monolithic structure including the body portion 6020, extension portion 6021, and breakaway structure 6023 that provides a "breakaway" or "snap-off" connection between the body portion 6020 and the extension portion 6021.

The extension portion 6021 extends between a first end 6025 and a second end 6027. The second end 6027 is interconnected to the breakaway structure 6023. The first end 6025 may be provided with a mechanical connector (such as threads, not shown) for being connected to an insertion and tensioning instrument such as instrument 7000 described above.

The breakaway structure 6023 is configured in terms of its shape, dimensions, and material properties such that it will retain its structural integrity and interconnected the body portion 6020 and the extension portion 6021 when subjected to tensile loads up to a first magnitude sufficient to complete a swaging process of the anchor 6012 as described below. This is referred to herein as a "first predetermined tensile load". The breakaway structure 6023 is further configured in terms of its shape, dimensions, and material properties such that it will fail and permit separation of the body portion 6020 and the extension portion 6021 when subjected to tensile loads equal to or greater than a second magnitude, referred to herein as a "second predetermined tensile load". The second tensile load is greater than the first tensile load. The second tensile load may be selected to be sufficiently greater than the first predetermined tensile load such that failure of the breakaway structure 6023 is unlikely to occur during the swaging process. Stated another way, the second predetermined tensile load may have a safety margin over the first predetermined tensile load. In one example, the second predetermined tensile load may be selected to be at least 50% to 100% greater than the first predetermined tensile load.

In general, the breakaway structure 6023 may include one or more stress-concentrating columns which present a known cross-sectional area, thus permitting reliable computation of the tensile stresses in the breakaway structure 6023 for a given applied load.

In the illustrated example, best seen in FIGS. 155 and 160, the breakaway structure 6023 includes a pair of stress-concentrating columns 6050 disposed on opposite sides of the body portion 6020, which have a circular cross-sectional shape. It will be understood that other column cross-sectional shapes providing a predictable cross-sectional area may be used, and that the cross-sectional shape may vary over the length of the column.

The body portion 6020 includes a base 6060 which is curved or contoured and includes a top surface 6062 and an opposed bottom surface 6064. A roughly cylindrical boss 6066 extends from the top surface 6062. The boss 6066 encloses the collet 6016 and sleeve 6018 and may be substantially similar in internal construction to the body portion 5020 described above. A central rib 6068 protrudes from the top surface 6062 and includes a concave channel 6070 which communicates with a central opening 6072 in the boss 6066. One or more anchor brackets 6074 extends from the top surface 6062. The bottom surface 6064 is generally smooth and curved in one plane.

FIG. 161 shows the clamp 6012 in position against a human femur F in preparation for applying a cerclage using the tensile member 10 wrapped around the femur F or other bone, with its distal ends inserted through the clamp 6012. The methods described above are used to tension the tensile member 10 and to force the sleeve 6018 down over the collet 6016 causing it to swage down onto and anchor the tensile member 10.

FIG. 162 shows the completed cerclage applied to a human femur F using the clamp 6012 of FIG. 155 in combination with a tensile member 10. The body portion 6020 of the housing 6014 remains in place, holding the tensile member 10 under the desired final tension, while the extension portion 6021 of the housing 6014 is removed. One end or portion of the tensile member 10 is connected to the anchor bracket 6074, while another end or portion is received in the collet 6016.

FIGS. 163 and 164 illustrate another exemplary clamp 8012 which may be used to receive an anchor distal ends of one or more tensile members 10 in order to apply a cerclage as described above. The clamp 8012 is a variation of the clamp 6012 described above. The clamp 8012 includes a housing 8014 that encloses a collet and a sleeve (not shown). The characteristics and configuration of the elements of the clamp 8012, in particular the collet and sleeve, may be substantially similar to corresponding elements of the anchor 6012 described above. The clamp 8012 may be implanted using any of the insertion instruments described herein.

The housing 8014 includes an extension portion 8021 coupled to a body portion 8020 by a breakaway structure 8023. The extension portion 8021 and breakaway structure 8023 are substantially identical to the corresponding structures of the claim 6012.

The body portion 8020 includes a base 8060 which is curved or contoured and includes a top surface 8062 and an opposed bottom surface 8064. A roughly cylindrical boss 8066 extends from the top surface 8062. The boss 8066 encloses the collet and sleeve (not visible) and may be substantially similar in internal construction to the body portions 5020 or 6020 described above. A central rib 8068 protrudes from the top surface 8062 and includes a pair of side-by-side concave channels 8070 and 8071. The first channel 8070 communicates with a central opening 8072 in the boss 8066. The second channel 8071 extends axially a short distance and terminates at a protruding, convex bearing surface 8073. First and second anchor brackets 8074, 8075 respectively extend from the top surface 8062, flanking the central rib 8068. The bottom surface 8064 is generally smooth and curved in one plane.

FIG. 165 shows the clamp 8012 in position in preparation for applying a cerclage using two or more tensile members 10, designated 10A and 10B for reference purposes.

The first tensile member 10A has a first end which is secured to the first anchor bracket 8074. The body of the first tensile member 10A is wrapped in a first direction (e.g. clockwise) to form a first loop 8076, and a second end thereof is passed through the concave channel 8070 and through the central opening 8072 so as to pass through the collet in order to be tensioned and swaged in the manner described above.

The second tensile member 10B has a first end which is secured to the second anchor bracket 8075. The body of the second tensile member 10B is wrapped in a second direction (e.g. counterclockwise) to form a second loop 8078, and a second end thereof is passed over the channel 8071 and around the bearing surface 8073, reversing direction to pass through the central opening 8072 so as to pass through the collet in order to be tensioned and swaged in the manner described above.

It will be understood that in use, the first and second loops 8076, 8078 would pass around a bone or other anatomical structure is described for the cerclages above. When tensioned, the first and second loops 8076, 8078 tend to move in opposite directions as their circumferences are shortened. As the displacements and forces on the first and second loops 8076, 8078 are equal and opposite, this will have the effect of minimizing or eliminating any tendency of the tensioning process to cause the clamp 8012 to "walk" around the bone or other anatomical structure.

FIGS. 166-170 illustrate an exemplary tensioner 9000 having a hollow housing 9002 which may be connected to any of the insertion instruments described above. The tensioner 9000 is one example of how tension may be applied through incremental compression of the spring element and may be substituted for any of the tensioning devices described above. The housing 9002 has a front end 9004 and a rear end 9006. The front end 9004 includes a nose 9008 configured to be attached to the tensioner. A shuttle assembly 9010 comprising an adjustment knob 9012 with fixed, externally-threaded tube 9014 and a hollow, internally-threaded tube 9016 is received inside the housing 9002. As best seen in FIG. 168, a compression spring 9018 is captured between the shuttle 9016 and the front end 9004 of the housing 9002. A retention pin 9020 is fixed in the housing 9002 and engages a longitudinal slot 9022 of the shuttle 9016. This assembled, the shuttle 9016 can translate forward and aft relative to the housing 9002, to a limited degree.

A hollow inner shaft 9024 passes through the threaded tube 9014, shuttle 9016, and housing 9002. The inner shaft 9024 includes an oversized boss 9026 which prevents the inner shaft 9024 from being withdrawn out the rear and 9006 of the housing 9002. A grooved spool 9028 is fixed to the inner shaft 9024 opposite the boss 9026 prevents the inner shaft 9024 from being withdrawn out the front end 9004 of the housing 9002. The inner shaft 9024 and shuttle 9016 may include complementary features to prevent relative rotation. For example, the inner shaft 9024 may include one or more flats that engage complementary flats of the shuttle 9016.

The operation of the tensioner 9000 may be best understood with reference to FIGS. 168-170. FIG. 168 shows the tensioner 9000 prior to the removal of slack in a tensile member 10 (not shown) or to the application of tension. It will be understood that in use, the tensioner 9000 abuts an insertion instrument or other structure providing a reaction force towards the rear end 9006 of the housing 9002, as shown by the schematic connection to a ground structure. It will further be understood that in use, a first end of a tensile member 10 passes through the hollow interior of the inner shaft 9024 and is secured to the spool 9028, and that an opposite end of the tensile member 10 would be fixed to prevent movement, e.g. by being engaged with an anchor as described above. This is shown by the schematic connection to a ground structure in FIG. 169.

In FIG. 168, the spring 9018 is in a generally uncompressed position and the shuttle assembly 9010 is in a collapsed or shortened condition. The tensile member 10 exhibits slack or is otherwise in a condition to be further extended without the application of significant additional force. This "slack" condition is shown in exaggerated form in FIG. 169. The tensioner 9000 have an overall length "L1" measured from the front end 9004 of the housing 9002 to the spool 9028.

FIG. 169 shows a condition in which slack is removed from the tensile member 10 without the application of a substantial amount of tension by rotating the adjustment knob 9012 to extend the shuttle assembly 9010. An overall length "L2" which is increased relative to overall length L1.

FIG. 170 shows a condition in which all slack is removed and the shuttle assembly has been further extended by additional rotation of the adjustment knob 9012. Because the slack has been removed from the tensile member 10, this further extension of the shuttle assembly 9010 causes the shuttle 9016 to compress the spring 9018. The tension applied to the tensile member by the spring 9018 acting through the shuttle assembly and spool 9028 is proportional to the compression of the spring 9018 and may be adjusted as desired by incremental movement of the knob 9012. Overall length "L3" of the tensioner 9000 is approximately the same as overall length L2.

FIGS. 171-173 illustrate another exemplary clamp 10012 which may be used to receive and anchor distal ends of one or more tensile members 10 in order to apply a cerclage as described above. The clamp 10012 includes collet 10016, and a sleeve 10018 (see FIG. 176). The characteristics and configuration of the elements of the collet 10016 and sleeve 10018 may be substantially similar to corresponding elements of the anchor 5012 described above. The clamp 10012 differs from the clamps described above in that it does not include its own housing. Instead, when fully swaged, the collet 10016 is retained in the swaged condition by the surrounding sleeve 10018, as best seen in FIG. 177.

The clamp 10012 may be implanted using an insertion instrument 10010, only a portion of which is shown in FIGS. 171-173. It includes a housing 10014 formed by two or more jaws 10011 which are moveable between an open position and a closed position. They could be moveable by pivoting between open and closed positions as shown in FIGS. 171 and 172, or by translation, or by being assembled and disassembled. Each jaw 10011 defines a portion of an internal surface 10028 similar to internal surface 28 described above, and may include internal flange 10031 similar to internal flange 31 described above. In the open position (FIG. 172), a clamp 10012 may be inserted between the jaws 10011 which would then be closed around the clamp 10012, forming the complete housing 10014. The insertion instrument 10010 further includes a hollow pushrod 10013 extending through the housing 10014 that is slidably movable between retracted and extended positions. The pushrod 10013 is connected to a driving mechanism as described above (not shown) for moving the pushrod 10013 between retracted and extended positions. The swaging action is as described above. The insertion instrument 10010 may be used in conjunction with any of the tensioners described herein.

FIG. 174 shows the clamp 10012 in position against a human femur F in preparation for applying a cerclage using the tensile member 10 wrapped around the femur F or other bone, with its distal ends inserted through the clamp 10012. The methods described above are used to tension the tensile member 10 and to force the sleeve 10018 down over the collet 10016 causing it to swage down onto and anchor the tensile member 10.

FIG. 175 shows the completed cerclage applied to a human femur F using the clamp 10012 of FIG. 171 in combination with a tensile member 10. The collet 10016 and sleeve 10018 remain in place, holding the tensile member 10 under the desired final tension, while the housing 10014 is part of the instrument 10010 and is removed.

Alternatively, the clamp 10012 may be implanted using an insertion instrument 11010, a portion of which is shown in FIG. 178. The insertion instrument 11010 is substantially similar in overall construction to the instrument 10010 described above. Aspects of the insertion instrument 11010 not specifically described may be taken to be identical to corresponding aspects of the insertion instrument 10010. The insertion instrument 11010 includes a housing 11014 formed by two or more jaws 11011 which are moveable between an open position and a closed position. They could be moveable by pivoting between open and closed positions as shown, or by translation, or by being assembled and disassembled. Each jaw 11011 defines a portion of an internal surface 11028 similar to internal surface 28 described above, and may include internal flange 10031 similar to internal flange 31 described above. In the open position (FIG. 179), a clamp 10012 may be inserted between the jaws 11011 which would then be closed around the clamp 10012, forming the complete housing 11014.

The instrument 11010 includes at least one tensile member anchor point. In the illustrated example, one of the jaws 11011 extends axially beyond the end of the adjacent jaw 11011 and defines a horn 11015 including a notch 11017. It further includes a ramp 11019 communicating with the internal surface 11028 and extending laterally outward to the outer surface of the jaws 11011. The insertion instrument 11010 further includes a hollow pushrod (not separately illustrated for this embodiment; see FIG. 172) extending through the housing 10014 that is slidably movable between retracted and extended positions. The swaging action is as described above. The insertion instrument 11010 may be used in conjunction with any of the tensioners described herein.

The instrument 11010 is particularly suited for applying a clamp 10012 described above which retains two or more tensile members 10, or two or more side-by-side passes of a single tensile member 10, for example in cerclage or in-line applications. FIG. 180-182 illustrate a cerclage application in more detail.

In FIG. 180, tensile member 10 is shown threaded through instrument 11010 in preparation for tensioning. The jaws 11011 are in the closed position and it will be understood that a clamp 10012 as described above is positioned between the jaws 11011 (not visible in FIG. 180).

A first portion 11020 of the tensile member 10 is looped or wrapped around the horn 11015. This results in substantial friction between the tensile member 10 and the instrument 11010, resisting tension applied to the tensile member 10. An adjacent portion 11021 of the tensile member 10 passes through the clamp 10012. Another portion 11022 adjacent portion 11021 passes through the ramp 11019 and exits the instrument 11010. Another portion 11023 adjacent portion 11022 is formed in the loop of sufficient size to encircle a bone or other anatomical structure that is to be clamped. Another portion 11024 adjacent portion 11023 is passed back through the clamp 10012. A final portion 11025 adjacent portion 11024 passes through the instrument 11010 where it may be engaged with a tensioner as described above (not shown). It will be understood that so configured, two separate strands of tensile member 10 are passing through the clamp 10012, one end or portion 11020 of the tensile member 10 is anchored to the horn 11015, and an opposite end or portion 11025 of the tensile member 10 extends out the instrument 11010 opposite the end or portion 11020. Moving the end or portion 11025 by applying tension thereto in the direction of the arrow in FIG. 180 while maintaining the instrument 11010 in place will thus close the loop portion of the tensile member 10, shrinking the loop and/or applying clamping force (i.e. hoop stress) to the tensile member 10.

FIG. 181 shows the process of using instrument 11010 to apply tensile member 10 as a cerclage around a human femur F. Once so placed and properly tensioned, the instrument 11010 may be actuated to swage the clamp 10012 substantially as described above, securing the tensile member 10 and retaining the selected tensile stress (tension) applied thereto. Other bones could be clamped with a cerclage, for example the sternum (not shown). In FIG. 181, the insertion instrument 11010 is shown as extending in-line or axially relative to the long axis of the clamp 10012. It will be understood that the instrument 11010 could have a different physical configuration so long as it is capable of applying the swaging force to the clamp 10012. For example, in other nine illustrated embodiments, the instrument 11010 could extend perpendicular to the long axis of the clamp 10012, or at some other convenient angle.

Subsequently, as shown in FIG. 182, the jaws 11011 may be opened so that the instrument 11010 can be removed, leaving the clamp 10012 securing the tensile member 10 in place. The clamp 10012, lacking a separate housing, occupies a minimal volume.

FIGS. 183 and 184 illustrate an in-line application in more detail. In FIG. 183, first and second tensile members 10, 10' are shown threaded through instrument 11010 in preparation for tensioning. The jaws 11011 are in the closed position and it will be understood that a clamp 10012 as described above is positioned between the jaws 11011.

A first portion 11026 of the first tensile member 10 is looped or wrapped around the horn 11015. This results in substantial friction between the first tensile member 10 and the instrument 11010, resisting tension applied to the first tensile member 10. An adjacent portion 11027 of the first tensile member 10 passes through the clamp 10012. Another portion 11028 adjacent portion 11027 passes through the ramp 11019 and exits the instrument 11010. Another portion 11029 adjacent portion 11028 is anchored or affixed to an anatomical structure in such a manner so as to resist tensile forces. The anchoring may use an anchor or clamp as described elsewhere herein or more conventional means such as a washer, bone anchor, or tying off. In the illustrated example (FIG. 184), the portion 11029 is anchored in the calcaneus bone C.

A portion 11030 of the second tensile member 10' is anchored or affixed to an anatomical structure in such a manner so as to resist tensile forces. The anchoring may use an anchor or clamped as described elsewhere herein or more conventional means such as a washer, bone anchor, or tying off. In the illustrated example (FIG. 184), the portion 11030 is anchored in a metatarsal M.

A portion 11031 of the second tensile member 10' adjacent the portion 11030 passes through the clamp 10012 (i.e. side-by-side to the first tensile member 10). A portion 11032 adjacent portion 11031 passes through the instrument 11010 where it may be engaged with a tensioner as described above (not shown). It will be understood that so configured, two separate tensile member strands, each of which is a portion of the respective tensile member 10, 10', are passing through the clamp 10012, the first tensile member 10 is anchored between the horn 11015 and a first anatomical structure, and the second tensile member 10' is anchored between a second anatomical structure and the instrument 11010. Moving the end or portion 11032 by applying tension thereto in the direction of the arrow in FIG. 183 while maintaining the instrument 11010 in place will thus apply tension to both tensile members 10, 10', applying tension to the two anatomical structures (in this example the metatarsal M and the calcaneus bone C).

Once so placed and properly tensioned, the instrument 11010 may be actuated to swage the clamp 10012 substantially as described above, securing the tensile members 10, 10' and retaining the selected tensile stress (tension) applied thereto.

Subsequently, the jaws 11011 may be opened so that the instrument 11010 can be removed, leaving the clamp 10012 securing the tensile members 10, 10' in place. The clamp 10012, lacking a separate housing, occupies a minimal volume.

The clamp 10012 may be applied in various configurations in addition to the cerclage and in-line configurations already described above. FIG. 185 illustrates an example in which a first tensile member 10 passes through the clamp 10012 and has opposite ends anchored or connected on opposite sides of the clamp 10012. A second tensile member 10' passes through the clamp 10012, is doubled over on itself, and has both of its ends anchored or connected on the same side of the clamp 10012. FIG. 186 shows the FIG. 185 configuration applied as a cerclage.

FIG. 187 illustrates an example in which to tensile members 10, 10' passed through a clamp 10012 which is placed in tandem with and abutting a second clamp 10012. The two clamps 10012 are shown oriented in opposite directions relative to the tensile members 10, 10'. FIG. 188 shows the FIG. 187 configuration applied as a cerclage.

The apparatus and method described herein has numerous benefits compared to the prior art. It provides a modular device and implant system and method that enables provisional and permanently stable tensioning of the tensile member, with minimally-invasive access to and limited visualization of the bone surface, using a device that is small and low-profile to prevent stress-shielding and soft tissue hang-up, implanted by simple and intuitive instrumentation that optimizes workflow and can be accomplished by one person.

The device and method described above may be used for procedures such as tensioning ligaments and tendons, augmenting ligaments and tendons, repairing and/or replacing ligaments and tendons, and reducing and fixate bone fractures.

The foregoing has described apparatus and methods for medical implants. All of the features disclosed in this specification, and/or all of the steps of any method or process so disclosed, may be combined in any combination, except combinations where at least some of such features and/or steps are mutually exclusive.

Each feature disclosed in this specification may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends, or to any novel one, or any novel combination, of the steps of any method or process so disclosed.

What is claimed is:

1. An apparatus for attaching a clamp for anchoring one or more tensile members, comprising:
 a clamp, including:
  a collet having a peripheral wall defining a central bore for accepting one or more tensile members therethrough and an exterior surface, wherein the collet is configured to be swaged around and against the one or more tensile members;
  a sleeve having a peripheral wall defining opposed interior and exterior surfaces, the sleeve positioned generally axially adjacent to the collet, so as to be movable parallel to a mutual central axis of the sleeve and the collet, between first and second positions; and
  wherein at least one of the exterior surface of the collet and the interior surface of the sleeve is tapered and the sleeve and the collet are arranged such that movement of the sleeve from the first position to the second position will cause the interior surface of the sleeve to bear against the exterior surface of the collet, causing the collet to swage radially inwards around and against the one or more tensile members; and
 an insertion instrument including:
  two or more moveable jaws cooperatively defining a housing extending along a central axis between open first and second ends, and having a hollow interior sized to receive the clamp; and
  a driving mechanism operable to move the sleeve from the first position towards the second position.

2. The apparatus of claim 1 wherein the collet includes an array of longitudinal grooves having a U-shape formed in an outer surface of the peripheral wall, each groove defining a neck configured to collapse inward and protrude into the central bore.

3. The apparatus of claim 1 wherein the collet includes an array of longitudinal grooves formed in an outer surface of the peripheral wall, each groove defining a web configured to collapse inward in response to external compressive force.

4. The apparatus of claim 1 further comprising a surface texture configured to enhance grip on a tensile member formed in the central bore.

5. The apparatus of claim 1 wherein at least one of the jaws includes an anchor point for securing a tensile member thereto.

6. The apparatus of claim 5 wherein the anchor point includes a horn including a groove.

7. The apparatus of claim 1 further comprising first and second tensile member strands received in the central bore of the collet.

* * * * *